(12) United States Patent
Zilla et al.

(10) Patent No.: US 8,906,082 B2
(45) Date of Patent: *Dec. 9, 2014

(54) GRAFT APPARATUS

(71) Applicant: Kips Bay Medical, Inc., Minneapolis, MN (US)

(72) Inventors: Peter P. Zilla, Cape Town (ZA); Nasser Rafiee, Andover, MA (US); Deon Bezuidenhout, Cape Town (ZA); Thomas Franz, Devils Peak (ZA); Mark Yeoman, East Sussex (GB); Hellmut C Bowles, Bloubergrant (ZA); Nareak Douk, Lowell, MA (US); Michael F Wolf, Golden Valley, MN (US); Paul Human, Cape Town (ZA)

(73) Assignee: Kips Bay Medical, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/048,864

(22) Filed: Oct. 8, 2013

(65) Prior Publication Data

US 2014/0039352 A1  Feb. 6, 2014

Related U.S. Application Data

(60) Division of application No. 13/745,999, filed on Jan. 21, 2013, which is a continuation of application No.

(Continued)

(51) Int. Cl.
*A61F 2/06* (2013.01)
*A61F 2/82* (2013.01)

(Continued)

(52) U.S. Cl.
CPC ... *A61F 2/07* (2013.01); *A61F 2/06* (2013.01); *A61B 5/1076* (2013.01); *A61F 2/90* (2013.01); *A61F 2/95* (2013.01); *A61F 2/82* (2013.01)
USPC .......................................... 623/1.13; 806/108

(58) Field of Classification Search
CPC ...................................... A61F 2/97; A61F 2/07
USPC .................................. 623/1.13, 1.15; 606/108
See application file for complete search history.

(56) References Cited

U.S. PATENT DOCUMENTS

| | | | |
|---|---|---|---|
| 3,337,673 A | 8/1967 | Jeckel | |
| 3,626,947 A | 12/1971 | Sparks | |

(Continued)

FOREIGN PATENT DOCUMENTS

| | | |
|---|---|---|
| DE | 19910340 | 9/2000 |
| RU | 2102016 | 1/1998 |

(Continued)

OTHER PUBLICATIONS

Biocompound Shunt, Application set for the repair of aneurysm in arterio-venous shunts. 2005, article from site: www.alpha-research.com: 8 pages.

(Continued)

*Primary Examiner* — Jason-Dennis Stewart
(74) *Attorney, Agent, or Firm* — Haugen Law Firm PLLP

(57) ABSTRACT

Stents and methods of using stents are provided. Stents of the invention provide external support structure for a blood vessel segment disposed within, wherein the stents are capable of resilient radial expansion in a manner mimicking the compliance properties of an artery. The stent may be formed of a knitted or braided mesh formed so as to provide the needed compliance properties. A venous graft with the stent and a vein segment disposed within is provided, wherein graft is capable of mimicking the compliance properties of an artery. Methods of selecting stents for downsizing and methods of using the stents of the invention in downsizing and smoothening are provided. Methods of replacing a section of an artery with a venous graft including a stent of the invention are provided. Methods of reducing intimal hyperplasia in implanted vein segment in a venous graft using stents of the invention are provided.

3 Claims, 21 Drawing Sheets

Related U.S. Application Data

13/209,517, filed on Aug. 15, 2011, now Pat. No. 8,382,814, which is a continuation-in-part of application No. 11/797,648, filed on May 4, 2007, now Pat. No. 7,998,188, which is a continuation-in-part of application No. 10/987,313, filed on Nov. 12, 2004, now abandoned, which is a continuation-in-part of application No. 10/834,360, filed on Apr. 28, 2004, now Pat. No. 8,057,537.

(60) Provisional application No. 60/466,226, filed on Apr. 28, 2003.

(51) Int. Cl.
 A61F 11/00 (2006.01)
 A61B 5/107 (2006.01)
 A61F 2/95 (2013.01)
 A61F 2/07 (2013.01)
 A61F 2/90 (2013.01)

(56) References Cited

U.S. PATENT DOCUMENTS

| | | |
|---|---|---|
| 3,797,485 A | 3/1974 | Urquhart |
| 3,974,526 A | 8/1976 | Dardik |
| 4,173,689 A | 11/1979 | Lyman et al. |
| 4,652,264 A | 3/1987 | Dumican |
| 4,725,273 A | 2/1988 | Kira |
| 4,743,251 A | 5/1988 | Barra |
| 4,921,495 A | 5/1990 | Kira |
| 4,922,905 A | 5/1990 | Strecker |
| 4,956,178 A | 9/1990 | Badylak et al. |
| 4,969,896 A | 11/1990 | Shors |
| 5,234,755 A | 8/1993 | Okamura |
| 5,320,100 A | 6/1994 | Herweck et al. |
| 5,366,504 A | 11/1994 | Andersen et al. |
| 5,413,598 A | 5/1995 | Moreland |
| 5,478,349 A | 12/1995 | Nicholas |
| 5,556,414 A | 9/1996 | Turi |
| 5,584,876 A | 12/1996 | Bruchman et al. |
| 5,645,581 A | 7/1997 | Zurbrugg |
| 5,662,713 A | 9/1997 | Andersen et al. |
| 5,674,276 A | 10/1997 | Andersen et al. |
| 5,681,645 A | 10/1997 | Strack et al. |
| 5,697,970 A | 12/1997 | Schmitt et al. |
| 5,700,287 A | 12/1997 | Myers et al. |
| 5,716,395 A | 2/1998 | Myers et al. |
| 5,725,570 A | 3/1998 | Heath |
| 5,728,150 A | 3/1998 | McDonald et al. |
| 5,733,327 A | 3/1998 | Igaki et al. |
| 5,755,659 A | 5/1998 | Zurbrugg |
| 5,769,884 A | 6/1998 | Solovay |
| 5,817,100 A | 10/1998 | Igaki |
| 5,824,047 A | 10/1998 | Moreland |
| 5,900,433 A | 5/1999 | Igo et al. |
| 5,910,168 A | 6/1999 | Myers et al. |
| 5,913,894 A | 6/1999 | Schmitt |
| 5,921,995 A | 7/1999 | Kleshinski |
| 5,989,287 A | 11/1999 | Yang |
| 5,997,573 A | 12/1999 | Quijano |
| 6,036,723 A | 3/2000 | Anidjar et al. |
| 6,053,943 A | 4/2000 | Edwin et al. |
| 6,071,306 A | 6/2000 | Angelini |
| 6,077,298 A | 6/2000 | Tu et al. |
| 6,113,612 A | 9/2000 | Swanson et al. |
| 6,117,166 A | 9/2000 | Winston et al. |
| 6,117,535 A | 9/2000 | Szycher |
| 6,123,115 A | 9/2000 | Greenhalgh |
| 6,159,239 A | 12/2000 | Greenhalgh |
| 6,161,399 A | 12/2000 | Jayaraman |
| 6,164,339 A | 12/2000 | Greenhalgh |
| 6,187,038 B1 | 2/2001 | Sullivan et al. |
| 6,192,944 B1 | 2/2001 | Greenhalgh |
| 6,217,609 B1 | 4/2001 | Haverkost |
| 6,221,099 B1 | 4/2001 | Andersen et al. |
| 6,264,684 B1 | 7/2001 | Banas et al. |
| 6,290,721 B1 | 9/2001 | Heath |
| 6,293,965 B1 | 9/2001 | Berg et al. |
| 6,319,279 B1 | 11/2001 | Shannon et al. |
| 6,331,191 B1 | 12/2001 | Chobotov |
| 6,358,275 B1 | 3/2002 | McIlroy et al. |
| 6,364,895 B1 | 4/2002 | Greenhalgh |
| 6,371,981 B1 | 4/2002 | Yang |
| 6,375,670 B1 | 4/2002 | Greenhalgh |
| 6,391,037 B1 | 5/2002 | Greenhalgh |
| 6,444,228 B1 | 9/2002 | Baugh |
| 6,485,513 B1 | 11/2002 | Fan |
| 6,494,909 B2 | 12/2002 | Greenhalgh |
| 6,551,352 B2 | 4/2003 | Clerc et al. |
| 6,554,856 B1 | 4/2003 | Doorly |
| 6,572,650 B1 | 6/2003 | Abraham |
| 6,596,180 B2 | 7/2003 | Baugh |
| 6,652,543 B2 | 11/2003 | Spence et al. |
| 6,656,217 B1 | 12/2003 | Herzog et al. |
| 6,709,455 B1 | 3/2004 | Chouinard |
| 6,792,979 B2 | 9/2004 | Konya et al. |
| 6,916,336 B2 | 7/2005 | Patel et al. |
| 7,011,676 B2 | 3/2006 | Dong |
| 7,041,131 B2 | 5/2006 | Abraham |
| 7,060,022 B2 | 6/2006 | Chen |
| 7,264,631 B2 | 9/2007 | DiCarlo |
| 7,335,214 B2 | 2/2008 | Lane |
| RE40,404 E | 6/2008 | Schmitt et al. |
| 7,387,604 B2 | 6/2008 | Case et al. |
| 7,452,374 B2 | 11/2008 | Hain et al. |
| 7,481,836 B2 | 1/2009 | Greenan |
| 7,575,592 B2 | 8/2009 | Woo |
| 7,666,222 B2 | 2/2010 | Wright et al. |
| 2002/0058992 A1 | 5/2002 | Greenhalgh |
| 2002/0083820 A1 | 7/2002 | Greenhalgh |
| 2003/0167088 A1 | 9/2003 | Abraham et al. |
| 2003/0204249 A1 | 10/2003 | Letort |
| 2004/0030348 A1 | 2/2004 | Peterson et al. |
| 2004/0215309 A1 | 10/2004 | Moritz |
| 2005/0004654 A1 | 1/2005 | Khosravi et al. |
| 2005/0131520 A1 | 6/2005 | Zilla et al. |
| 2005/0177224 A1 | 8/2005 | Fogarty et al. |
| 2006/0052866 A1 | 3/2006 | Gilles et al. |
| 2006/0069426 A1 | 3/2006 | Weinberger |
| 2006/0149348 A1 | 7/2006 | Vogel et al. |
| 2007/0055345 A1 | 3/2007 | Arbefeuille |
| 2007/0198079 A1 | 8/2007 | Casey et al. |
| 2008/0082160 A1 | 4/2008 | Boyden et al. |
| 2009/0171436 A1 | 7/2009 | Casanova et al. |

FOREIGN PATENT DOCUMENTS

| | | |
|---|---|---|
| WO | 9638090 | 12/1996 |
| WO | 2004096095 | 11/2004 |
| WO | 2007035791 | 3/2007 |
| WO | 2008118132 | 10/2008 |

OTHER PUBLICATIONS

Biocompound Graft, Application set for making and implanting the highly flexible biocompound graft, vascular prosthesis. 2001, article from site: www.alpha-research.com: 12 pages.

Angelini, G.D., et al., "An External, Oversized, Porous Polyester Stent Reduces Vein Graft Neointima Formulation [. . . ] in Cholorsetorol-fed Pigs", Journal of Thoracic and Cardiovascular Surgery, 124(5):950-956, Nov. 2002.

Angelini, G.D., et al., "External Stenting Reduces Early medial and Neointimal Thickening in a Pig Model of Arteriovenous Bypass Grafting", J. Thoracic Cardiovascular Surgery, 112(1): 79-84, Jul. 1996.

Angelini, G.D., et al., "Toweards the Treatment of Saphenous Vein Bypass Graft Failure—a Perspective of the Bristol Heart Institute", Bioheology, 39(3-4)L 491-499, 2002.

Bambang, L.S., et al., "External Biodegradable Supporting Conduit Protects Endothelioum in Vein Graft in Arterial Interposition", International Journal of Artifical Organs, 20(7): 397-406, 1997.

(56) References Cited

OTHER PUBLICATIONS

Barnes, R.W., et al., "Mesoaortic Compression of the Left Renal Vein (the so called Nutcracker Syndrome): Repair by a New Stenting Procedure", J. Vascurlar Surgery, 8 (4):415-421, Oct. 1988.

Barra, J.A., et al. "Constrcitive Perivenous Mesh Prosthesis for Preservation of Vein Integrity", J. Thoracic Cardiovascular Surgery, 92:330-336, 1986.

Batellier, J., et al., "Protection from Atherosclerosis in Vein Grafts by a Rigid External Support," Arteriosclerosis and Thrombosis, 13(3): 379-384, Mar. 1993.

Beattie, D.K., et al., "The Effects of Potassium Channel Openers on Saphenous Vein Exposed to Arterial Flow", Eur. J. Vascular Endovasc. Surg., 15(3): 224-249, 1998.

Berkowitz., H.D., et al., "Renovascular Hypertension in Children: Surgical Repair with Special Reference to the Use of Reinforce Vein Grafts", J. Vascular Surg., 9(1): 46-55, Jan. 1989.

Bourassa, M.G., "Long-Term Vein Graft Patency", Current Opinion in Cardiology, 9(6): 685-691, 1994.

Caggiati, A., et al., "Tee Long Saphenous Vein Compartment", Phlebology, 12: 107-111, 1997.

Campeau, L., et al., "Atherosclerosis and Late Closure of Aortocoronary Saphenous Vein Grafts: Sequential Angiographic Studies at 2 weeks, 1 year, 5 to 7 years, and 10 to 12 years after Surgery", Circulation, 68 (Supp. II): 1-7, Sep. 1983.

Dashwood, M.R., et al., "Nitric Oxide (NO) Release and NO Synthase in Porcine Venous-Arterial Grafts: Effect of External Stenging", Journal of Molecular and Cellular Cardiology, 29(6): A214 Abstract 237, 1997.

Dashwood, M.R., et al., "Does External Stenting Reduce Porcine Vein-Graft Occlusion via an Action on Vascular Nerves?". Journal Cardiac Surgery, 19(6): 556-560, 2002.

Deng, X., et al. "Effcency of an External Support to Reduce Lipid Infiltration into Venous Grafts: In Vitro Evaluation", Artificial Organs, 20(11)L 1208-1214, 1996.

Deng, X., et al., "Alternative Blood Conduits: Assessment of Whether the Porosity of Synthetic Prostheses is the Key to Long-Term Biofunctionality", Medical & Biological Engineering & Computing, 38(2): 219-225, 2000.

Dobrin, P.B., et al. "Mechanical and Histologic Changes in Canine Vein Grafts", J. Surg., Res., 44(3): 259-265, 1988.

Ferko, A., et al., "Autologous vein Stent-Graft: Feasibility Study", Journal of Vascular and Interventional Radiology, 11(1): 111-114, Jan. 2008.

George, S.J., et al.,"Macro-Porosity is Necessary for the Reduction of Neointimal and Medical Thickening by External Stenting of Porcine Saphenous Vein Bypass Grafts", Atherosclerosis: 155(2): 329-336, 2001.

George, S.J., et al., "An Essential Role for Platelet-Derived Growth Factor in Neointima Formation in Human Saphenous Vein in Vitro", Atherosclerosis, 120: 227-240, 1996.

Golledge, J., et al., "Circumferential Deformation and Shear Stress Induce Differential Responses in Saphenous Vein Endotheluim Exposed to Arterial Flow", J. Clin. Invest., 99(11): 2719-2726, Jun. 1997.

Golledge, J. et al., "Development of an in Vitro Model to Study the Response of Saphenous Vein Endothelium to Pulsatile Arterial Flow and Circumferential Deformation", Eur. J. Vascular Endovascular Surgery, 13: 605-612, 1997.

Grega, G.J., et al., "Effects of Dopamine (DA) and SKF-82526, a Selective DA1 Receptor Agonist on Vascular Resistances in the Canine Forelimb", Journal of Pharacology and Experimental Therapeutics, 22(3): 756-762.

Guldner, M.W., et al., "Fluid Dynamics of Autologous Vein Segment Valves with and without Cylindric External Stents", International J. Artifical Organs, 26(7): 659 Abstract P152, 2003.

Hodgson, D.E., et al., "Shape Memory Alloys", Metals Handbook (18th ed.) 2: 897-902, 1990.

Hofer, M., et al., "Numerical Study of Wall Mechanics and Fluid Dynamics in End-to-Side Anastomoses and Correlation to Intimal Hyperplasia", Journal Biomechanics, 29(10): 1297-1308, 1996.

Holzapfel, G.A., et al., "A Constitutive Framework of the Inelastic Mechanical Behavior or Arteries", Proceedings of 2001 ASME International Mechanical Engineering Congress and Exposition, Bioengineering Division (BED), 51: 325-236, '01.

Huynh, Tam T. T., et al., "External Support Modulates G Protein Expression and Receptor Coupling in Experimental Vein Grafts", Surgery 126(2): 127-134, 1999.

Huynh, Tam T. T., et al., "Alterations in Wall Tension and Shear Stress Module Tyrosine Kinase Signaling and Wall Remodeling in Experimental Vein Grafts", Journal Vascular Surgery, 29(2):334-344, 1999.

Izzat, M.B., et al., "Influence of External Stent Size on Early Medial and Neointima Thickening in a Pig Model of Saphenous Vein Bypass Grafting", Circulation, 94(7): 1741-1745, 1996.

Jeremy, J.Y., et al., "The Influence of External Stent Porosity on Early Neointima Formulation and Medial Wall Thickening in a Pig Model of Saphenous Vein Bypass Grafting", European Heart Journal, 20: 274 Abstract P1533, Aug. 1999.

Jeremy, J.Y., et al., "Nitric Oxide, Prostacyclin, and Cyclic Nucleotide Formation in Externally Stented Porcine Vein Grafts", Atherosclerosis 141(2): 297-305, 1998.

Jeremy, J.Y., et al., "A Bioabsorbable (Polyglactin), Nonrestrictive, External Sheath Inhibits Porcine Saphenous Vein Graft Thickening", Journal of Thoracic and Cardiovascular Surgery, 127(6): 1766-1772, Jun. 2004.

Karayannacos, P.E., et al. "Potential Role of Velocity and Wall Tension in Vein Graft Failure", J. Cardiovascular Surgery, 21:171-178, 1980.

Kilmek, W., et al., "In Vitro Intravascular Ultrasound Imaging of Biocompound Vein Grafts: Comparison to Histology", European Heart Journal, 20: 405 Abstract P2142, Aug. 1999.

Kohler, T., et al., "The Effect of Rigid External Support o Vein Graft Adaptation to the Arterial Circulation", J. Vasc. Surg., 9(2):277-285, 1989.

Krejca, M., et al., "Effects of External Stenting on the Durability of Vein Grafts", Kardiologia Polska, 57(8): 125-130, 2002.

Kus, J., "Przeszczepy Zyine Wzmocnione Porowat a Poliestrow A", Polski Tygodnik Lekarski, 19: 704-704, 1964 (English Language Title Only).

Lardenoye, J. H. P., et al., "Inhibition of Accelerated Atherosclerosis in Vein Grafts by Placement of External Stent in ApoE*3-Leidne Transgenic Mice", Arteriosclerosis Thromb. Vas. Biol., 22(9): 1433-1438, 2002.

Lendlein, A., et al., "AB Polymer Networks Based on Oligo (caprolactone) segments Showing Shape-Memory Properties", proc. Natl. Academy Sci., 98(3): 842-847, 2001.

Liu, S.Q., et al., "A Possible Role of Initial Cell Death Due to Mechanical Stretch in the Regulation of Subsequent Cell Proliferation in Experimental Vein Grafts", Biomechan. Model Mechanobiol., 1:17-27, 2002.

Liu, S.Q.,et al., "Partial Prevention of Conocyte and Granuloctre Activation in Experimental Vein Grafts by Using a Biomechanical Engineering Approach", Journal of Biomechanics, 32(11):1165-1175, 1999.

McGregor, W., et a., "Circumferential Stretching of Sapheous Vein Smooth Muscle Enhances Vasoconstrictor Responses by Rho Kinase-Dependent Pathways", Cardiovascular Research, 53(1):219-226, 2002.

Meguro, T., et al., "Effect of External Stenting and Systemic Hypertension on Intimal Hyperplasia in Rat Vein Grafts", Neurosurgery, 46(3):963-970, Apr. 2002.

Liu, S.Q., et al., "Prevention of Mechanical Stretch-Induced Endothelial and Smooth Muscle Cell Injury in Experimental Vein Grafts", Journal of Biomechanical Engineering, 122(1): 31-38, 2000.

Mechta, D., et al., "External Stenting Reduces Long-term Medial and Neointimal Thickening and Platelet Derived Growth Factor Expression in a Pig Model of Arteriovenous Bypass Grafting", Nature Medicine, 4(2):235-239, Feb. 1998.

Mechta, D., et al., "Protacyclin, Nitric Oxide and Cyclic Nucleotide Synthesis in Stented and Unstented Porcine Vein Grafts", British Journal of Pharmacology, 119: Abstract 132P, 1996.

Moritz, A., et al., "Use of Varicose Veins as Arterial Bypass Grafts", Vardiovasc. Surg., 1(5): 508-513, 1993.

(56) References Cited

OTHER PUBLICATIONS

Moritz, A., et al., "A Method for Constricting Large Veins for use in Arterial Vascular Reconstruction", Artificial Organs, 14(5): 394-398, 1990.
Moritz, A., et al., "The Use of Mesh-Tube-Constricted Dilated or Varicose Veins as Arterial Bypass Conduit", Thorac. Cardiovasc. Surg., 40(6): 356-360, 1992.
Moritz, A., et al., "Mesh Constricted Varicose and Dilated Veins Used as Arterial Bypass Grafts", International Journal Artificial Organs, 14(7): 345-440, 1991.
Moritz, A., et al., "Mesh Tube-Calibrated Varicose Veins for Coronary Artery Bypass Grafting", Ann. Thorac. Surg., 57:240-242, 1994.
Moritz, A., et al., Mesh Tube-Constricted Varicose Veins used as Bypass Grafts for Infrainguinal Arterial Reconstruction, Arch. Surg. 217(4): 416-420, 1992.
Moritz, A., et al., "Ummantelte Dilaierte oder Varikose Venen als Arterielles Bypasstransplantat: Experimentelle and Erste Klinishe Ergebnisse", Vasa, 20(3): 222-229, 1991 (English Language Summary on p. 228).
Neufang, A., et al., "External Reinforcement of Varicose Veins with PTFE Prosthesis in Infrainguinal Bypass Surgery", Thoracic Cardiovascular Surgery, 52(2): 62-66, 2003.
Panneton, J.M., et al., "Superior Vena Cava Syndrome: Relief with a Modified Saphenojugular Bypass Graft", Journal Vascular Surgery, 34(2): 360-363, 2001.
Papadopoulos, N.J., "A Fascial Canal for the Great Saphenous Vein: Gross and Micoanatomical Observations", Journal of Anatomy, 132(2): 321-329, May 1981.
Pillet, J., "Our Clinical Experience with . . . Loss of Arterial Substance. Application of the Procedure to Treatment of Aneurysmal Dilation of Femoral Venous Graft, Memories", Adadecie de Chirugie, 95(1): 64-67, 1969 (English Language Abstract Only).
Powell, J.T. et al., "Molecular and Cellular Changes in Vein Grafts: Influence of Pulsatile Stretch", Current Opinion in Cardiology, 13(6): 453-458. 1998.
Pshenisnov, K.P., et al. "Comparative Analysis of Structural Change in a Free Autovenous Graft and in a Transplant with Spiral Reinforcement after Correction of Experimental Arterial Defects", Cor Vasa, 30(3): 218-224, 1988.
Shimizu, K., et al., "Shape Memory Effect: Mechanism", Shape Memory Alloys (Funakubo, H., Ed.) Gordon and Breach CScience (Pub.) 1:1-60, 1987.
Shore, J.M., et al., "A Comparative Study of Canine Venous Autografts", Journal of Cardiovascular Surgery, 17: 67-75, 1964.
Soury, P., et al., "Prosthetic Reinforcement of Varicose Saphenous Vein Grafts for Infrainguinal Bypass", Ann. Vascular Surgery, 13(3): 290-293, 1999.
Sparks, C.H., et al. "Carotid Artery Replacement with Reinforced Autogenous Vein Grafts", Angiology, 14: 541-551, Nov. 1963.
Stocker, W., et al., "Pervenous Support Reduces Early Changes in Human Vein Grafts: Studies in Whole Blood Perfused Human Vein Segments", J. Thoracic Gardiovascular Surg., 121(2): 212-217, 2002.
Stocker, W., et al., "Surgical Sealing in the Prevention of Early Vein Graft Injury in an Ex Vivo Model", Cardiovascular Pathology, 12(4): 202-203, 2003.
Stocker, W., et al., "Perivenous Application of Fibrin Glue Reduces Early INjury in an Ex Vivo Model", European Journal of Cardio-Thoracic Surgery, 21(2): 212-217, 2002.
Stooker, W., et al., "Pressure-Diameter Relationship in the Human Greater Saphenous Vein", Ann. Thoracic Surg., 76(5): 1533-1538, 2003.
Tanabe, T., et al., "Wall Reinforcement with Highly Porous Draco Mesh in Aortic Surgery", Ann. Surg., 191(4): 452-455, 1980.
Tedugi, A., et al., "External Stenting and Atherosclerosis", Nature Medicine, 4(6): 645, Jun. 1998.
Trubel, W., et al., "Compliance Mismatch and Formation of Distal Anastomic Intimal Hyperplasia in Externally Stiffened and Lumen Adapted Venous Grafts", Eur. J. Vasc. Endovasc. Surg., 10(4): 415-423, 1995.
Trubel, W., et al., "Compliance and Formation of Distal Anastomic Intimal Hyperplasia in Dracon Mesh Tube Constricted Veins used as Aortal Bypass Grafts", ASAIO Journal, 40(3): M273-279, 1994.
Vijayan, V., et al., "External Supports and the Prevention of Neointima Formation in Vein Grafts", European Journal Vascular Endovascular Surg., 24(1): 13-22, 2002.
Yang, B., et al., "Effect of the Biodegradable Chitosan External Stent on the Early Changes in the Rabbit Vein Grafts", Chinese Journal of Surgery, 40(9): 688-690, Sep. 2003. (English Language Abstract).
Zhao, L., et al., "Results of Autogenous Vein Grafts in Repair of Major Arterial Injuries to the Upper and Lower Extremities with Reference to Wall Shear Stress", International Journal of Angiology, 6(2): 99-103, 1997.
Zidi, M., et al., "Mechinical Analysis of a Prototype of Small Diameter Vascular Prosthesis: Numerical Simulations", Computers in Biology and Medicine, 33:35-75, 2003.
Vijayan, V., et al., "Long-Term Reduction of Medial and Intimal Thickening in Porcine Saphenous Vein Grafts with a Polyglactin Biodegradable External Sheath", Journal Vascular Surgery, 40(5): 1011-1019, 2004.
Zurbrugg, H.R., et al., "The Biocompound Method in Coronary Artery Bypass Operations: Surgery Technique and 3-year Patency", Ann Thoracic Surg, 70:1536-1540, 2000.
Zurbrugg, H.R., et al., "Prevention of Venous Graft Sclerosis with Clopidogrel and Aspirin Combined with a Mesh Tubing in a Dog Model of Arteriovenous Bypass Grafting", European Journal Vascular Endovascular Surgery, 22(4): 337-341, 2001.
Zurbrugg, H.R., et al., "Reduction of Intimal and Medial Thickening in sheathed Vein Grafts", Ann. Thoracic Surg., 68(1): 79-83, 1999.
Zurbrugg, H.R., et al., "The Use of Biocompound-Grafts Together With Varicose Veins", Journal Cardiovascular Surgery, 37 (Suppl. 1 to No. 143-143, 1993.
Zurbrugg, H.R., et al., "Improvement of the Flow Provile in Bypass Surgery: First Clinical Experience with the Ultraflexible Biocompound-Graft", Swiss Surgery, Suppl. 1:8-12, 1996 (English Language Abstract on p. 9).
Zwolak, R.M., "Kinetics of Vein Graft Hyperplasia: Association with Tangential Stress", J. Vasc. Surg. 5(1): 126-136, 1987.

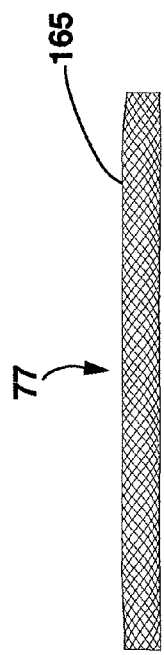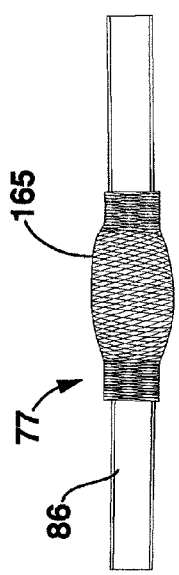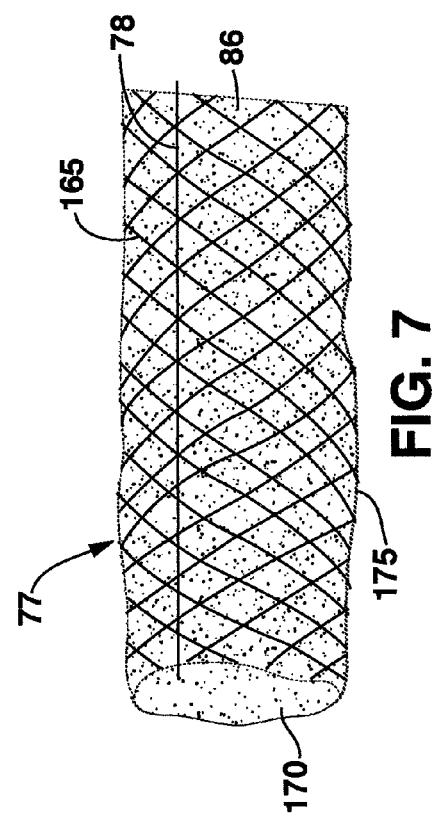

FIG. 8
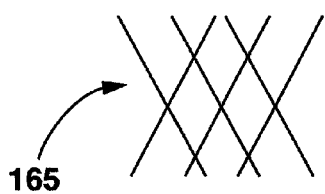
FIG. 9
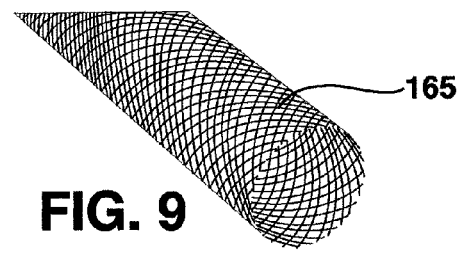
FIG. 10
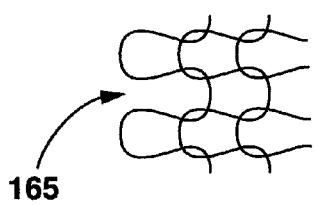
FIG. 11
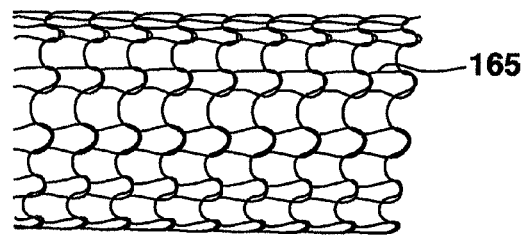
FIG. 12    FIG. 14    FIG. 15    FIG. 16
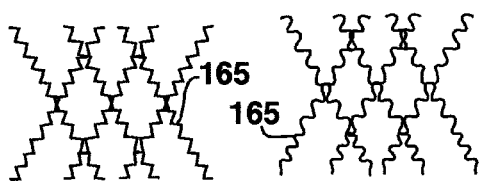
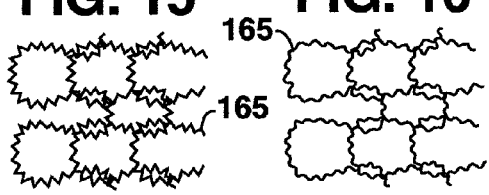
FIG. 13
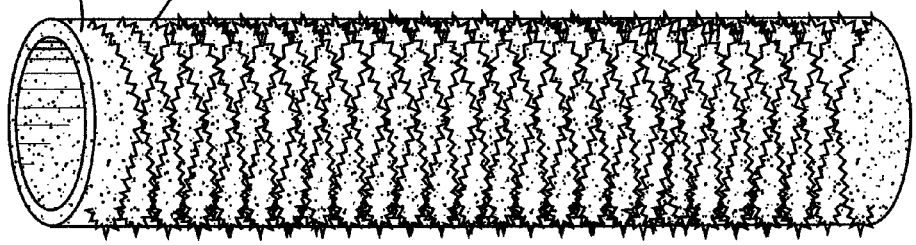

Knit 1

| | L1 | N1 | H1 | L2 | N2 | H2 | Ls | R1a | R1b | R2a | R2b | R1 | R2 |
|---|---|---|---|---|---|---|---|---|---|---|---|---|---|
| Average Meas | 0.95 | 0.82 | 1.06 | 0.92 | 0.19 | 0.43 | 1.23 | 0.24 | 0.14 | 0.15 | 0.17 | 0.19 | 0.16 |
| STDEV Meas | 0.05 | 0.01 | 0.03 | 0.05 | 0.03 | 0.01 | 0.05 | 0.02 | 0.00 | 0.02 | 0.01 | 0.01 | 0.01 |
| Average Corr | 0.95 | 0.84 | 1.10 | 0.92 | 0.19 | 0.43 | 1.23 | 0.24 | 0.14 | 0.15 | 0.17 | 0.19 | 0.16 |
| STDEV Corr | 0.05 | 0.00 | 0.03 | 0.05 | 0.02 | 0.01 | 0.05 | 0.02 | 0.00 | 0.02 | 0.01 | 0.01 | 0.01 |
| SEM corr | 0.03 | 0.00 | 0.02 | 0.03 | 0.01 | 0.00 | 0.03 | 0.01 | 0.00 | 0.01 | 0.00 | 0.00 | 0.00 |

Knit 2

| | L1 | N1 | H1 | L2 | N2 | H2 | Ls | R1a | R1b | R2a | R2b | R1 | R2 |
|---|---|---|---|---|---|---|---|---|---|---|---|---|---|
| Average Meas | 1.27 | 0.69 | 0.95 | 1.26 | 0.42 | 0.66 | 1.63 | 0.20 | 0.17 | 0.16 | 0.16 | 0.19 | 0.16 |
| STDEV Meas | 0.05 | 0.05 | 0.01 | 0.04 | 0.05 | 0.04 | 0.03 | 0.02 | 0.01 | 0.01 | 0.01 | 0.01 | 0.01 |
| Average Corr | 1.27 | 0.73 | 1.00 | 1.26 | 0.42 | 0.67 | 1.63 | 0.20 | 0.17 | 0.16 | 0.16 | 0.19 | 0.16 |
| STDEV Corr | 0.05 | 0.05 | 0.01 | 0.04 | 0.05 | 0.04 | 0.03 | 0.02 | 0.01 | 0.01 | 0.01 | 0.01 | 0.01 |
| SEM corr | 0.03 | 0.03 | 0.00 | 0.02 | 0.03 | 0.02 | 0.02 | 0.01 | 0.00 | 0.00 | 0.01 | 0.00 | 0.00 |

Knit 3

| | L1 | N1 | H1 | L2 | N2 | H2 | Ls | R1a | R1b | R2a | R2b | R1 | R2 |
|---|---|---|---|---|---|---|---|---|---|---|---|---|---|
| Average Meas | 1.13 | 0.55 | 0.84 | 1.13 | 0.56 | 0.84 | 1.66 | 0.27 | 0.34 | 0.31 | 0.33 | 0.31 | 0.32 |
| STDEV Meas | 0.03 | 0.00 | 0.03 | 0.01 | 0.01 | 0.02 | 0.01 | 0.03 | 0.05 | 0.02 | 0.02 | 0.04 | 0.02 |
| Average Corr | 1.13 | 0.55 | 0.84 | 1.13 | 0.59 | 0.90 | 1.66 | 0.27 | 0.34 | 0.31 | 0.33 | 0.31 | 0.32 |
| STDEV Corr | 0.03 | 0.00 | 0.03 | 0.01 | 0.00 | 0.02 | 0.01 | 0.03 | 0.05 | 0.02 | 0.02 | 0.04 | 0.02 |
| SEM corr | 0.02 | 0.00 | 0.02 | 0.01 | 0.00 | 0.01 | 0.01 | 0.01 | 0.03 | 0.01 | 0.01 | 0.02 | 0.01 |

Knit 4

| | L1 | N1 | H1 | L2 | N2 | H2 | Ls | R1a | R1b | R2a | R2b | R1 | R2 |
|---|---|---|---|---|---|---|---|---|---|---|---|---|---|
| Average Meas | 1.74 | 0.71 | 1.03 | 1.71 | 0.33 | 0.63 | 2.25 | 0.32 | 0.34 | 0.28 | 0.27 | 0.33 | 0.27 |
| STDEV Meas | 0.01 | 0.03 | 0.01 | 0.03 | 0.03 | 0.01 | 0.01 | 0.02 | 0.02 | 0.02 | 0.01 | 0.02 | 0.01 |
| Average Corr | 1.74 | 0.72 | 1.05 | 1.71 | 0.37 | 0.72 | 2.25 | 0.32 | 0.34 | 0.28 | 0.27 | 0.33 | 0.27 |
| STDEV Corr | 0.01 | 0.03 | 0.01 | 0.03 | 0.03 | 0.01 | 0.01 | 0.02 | 0.02 | 0.02 | 0.01 | 0.02 | 0.01 |
| SEM corr | 0.01 | 0.02 | 0.01 | 0.02 | 0.02 | 0.01 | 0.01 | 0.01 | 0.01 | 0.01 | 0.01 | 0.01 | 0.00 |

FIG. 39

GRAFT APPARATUS

CROSS-REFERENCE TO RELATED APPLICATIONS

The present application is a divisional of pending U.S. patent application Ser. No. 13/745,999, filed on Jan. 21, 2013, which is a continuation of pending U.S. patent application Ser. No. 13/209,517, filed on Aug. 15, 2011, which is a continuation of U.S. patent application Ser. No. 11/797,648, filed on May 4, 2007, and now issued as U.S. Pat. No. 7,998,188, which is a continuation-in-part of U.S. patent application Ser. No. 10/987,313, filed on Nov. 12, 2004 and now abandoned, which is a continuation-in-part of U.S. patent application Ser. No. 10/834,360, filed on Apr. 28, 2004 and issued as U.S. Pat. No. 8,057,537, which claims the benefit of priority from U.S. Provisional Patent Application Ser. No. 60/466,226, filed on Apr. 28, 2003, the contents of which are all incorporated herein by reference in their entireties.

BACKGROUND OF THE INVENTION

1. Field of the Invention

The present invention is generally related to a graft involving a blood vessel segment and a supportive sheath chosen to provide the graft with mechanical compliance properties which resemble those of a healthy native artery, and a method for sizing such a graft.

2. Description of Related Art

Various types of vascular prostheses are known or available. Commercially available synthetic vascular grafts in use are commonly made from expanded polytetrafluoroethylene (e-PTFE), or woven, knitted, or velour design polyethylene terephthalate (PET) or Dacron®. These prosthetic vascular grafts may have various drawbacks. When used for repairing or replacing smaller diameter arteries, these grafts may fail due to occlusion by thrombosis or kinking, or due to an anastomotic or neointimal hyperplasia (exuberant cell growth at the interface between artery and graft). Another problem may involve expansion and contraction mismatches between the host artery and the synthetic vascular prosthesis, which may result in anastomotic rupture, stimulated exuberant cell responses, and disturbed flow patterns and increased stresses leading to graft failure.

Problems also exist with the use of autologous saphenous vein grafts in these applications. Use of autologous saphenous vein grafts to bypass blockages in coronary arteries has become a well-established procedure. However, their success in the long term has been limited. In the coronary position, the literature reports a low (45-63%) patency of vein grafts after 10-12 years. It is believed that these failures result from remodeling of the implanted vein in response to greatly increased internal pressure, that is, as the vein is required to function as an artery. In general, arteries have substantial musculature and, although able to expand diametrically in response to increased internal pressure, are capable of withstanding normal arterial pressure variances. Veins, on the other hand, are not required to withstand arterial pressure variances and are relatively incapable of withstanding the higher arterial pressures without substantial bulging. In this regard, the nominal venous diameter seen under nominal venous pressure is seen to approximately double upon exposure to arterial pressure.

Increases in lumenal diameter of these magnitudes in vein segment implants are accompanied by increases in tangential stress. Tangential stress has been shown to be proportional to the lumenal radius-wall thickness ratio. In healthy arteries, this ratio remains constant across multiple species. However, this does not occur in veins. It is believed that a vein's smooth muscle cells increase their growth rate and secrete extracellular matrix components in response to such increases in tangential stress. This becomes a remodeling response, and is likely an attempt by the vein to reduce the lumenal radius-wall thickness ratio, and consequently the tangential stress. However, it appears that these reactions overcompensate in the veins, resulting in the phenomenon of neointimal hyperplasia yielding grossly thickened and stiff graft walls. As the dilation of the vein segment continues, the resulting mismatch between the vein and artery diameters may lead to disturbance of flow patterns, which may also favor the formation of thrombi.

Problems also exist when tubular prostheses are used as exteriorly accessible shunts to facilitate access to the circulatory system for, e.g., the administration of medicines and nourishment and for dialysis procedures.

For several decades saphenous vein grafts have been the most widely used arterial bypass conduits. As much as there is an increasing trend towards the use of arterial grafts such as the internal thoracic-, radial- or gastroepiploic artery, the saphenous vein will remain an indispensable conduit for large numbers of patients. This is particularly true for lower limb reconstructions where artery grafts are not available.

Although the overall patency of saphenous vein grafts is distinctly better than that of synthetic conduits, the failure rate of vein grafts is still sobering when compared with artery grafts. The main reason for the failure of vein grafts is the development of intimal hyperplasia. Since late vein graft failure due to arteriosclerotic degeneration also develops on the bed of intimal hyperplasia, this subintimal tissue development holds the master-key to poor vein graft performance. The consequences of this shortcoming are dramatically illustrated by the fact that one third of all peripheral vascular operations are revisions and at 5 years 50% of all peripheral grafts needing revision for failure led to an amputation.

It is well recognized that there are two major forms of intimal hyperplasia: a diffuse and a focal one. While diffuse intimal hyperplasia often regresses, focal intimal hyperplasia tends to progress, leading to a significantly higher occlusion rate. The overall triggers for both forms of intimal hyperplasia are low shear stress at the blood interface and high circumferential wall stress—both related to the significantly larger cross sectional area of the vein graft than the target artery and exposure to arterial pressure. The aggravating factors in focal narrowings, however, are areas of particularly low fluid shear stress and increased shear gradients. Eddy flow as a consequence of uneven lumenal dimensions was shown to be the reason behind these haemodynamic conditions causing focal intima hyperplasia. Independently, wall irregularities were shown to be the main predisposing condition for focal intimal hyperplasia.

As early as in the 1960s attempts were made to restrict the expansion of vein grafts in the arterial circulation and eliminate uneven lumenal dimensions through external mesh-support with diameter reduction. Since then, many investigators have researched this field but the translation into clinical practice was limited to last-resort measures in varicose veins.

BRIEF SUMMARY OF THE INVENTION

It has now been found that a blood vessel segment such as a vein segment, if externally supported by an appropriate, flexible, radially-resiliently tubular support, can provide a valuable tubular prosthesis. A vein segment so supported can function in much the same fashion as the artery that is to be replaced. That is, it functions without undue bulging or aggravated mismatching phenomena leading to graft failure. Unless otherwise indicated, the term "compliance" means the ratio of the diameter change of a vessel as it expands in the radial direction in response to a given change in vessel pressure, and the values for compliance referred to below result from dynamic, in vitro testing. The terms "venous graft" and "vein graft" are used interchangeably herein. As described in greater detail below, the compliance of venous graft (vein graft) is largely dependent upon the compliance of the external, radially resilient support.

The invention in one embodiment, accordingly, relates to a flexible, resilient, generally tubular external support within which may be supported a blood vessel segment such as a vein segment to form a graft. The tubular support is capable of resilient radial expansion in a manner mimicking the compliance properties of an artery, and compliance figures in the range of 3 to 30%/100 mm Hg are appropriate. The tubular support may be formed of a knitted or woven mesh that is so formed as to exhibit the needed compliance properties.

The invention in certain embodiments provides a venous graft (vein graft) for replacement of a section of an artery. The graft comprises a flexible, resilient, generally tubular external support and a vein segment carried within and having an ablumenal surface in contact with and supported by the tubular support, the venous graft being capable of resilient radial expansion in a manner mimicking the compliance properties of an artery. Compliance figures in the range of 3 to 30%/100 mm Hg are appropriate, although compliance values ranging up to 50%/100 mm Hg may be desired in some instances. The tubular support may take the form of a fiber mesh, such as a knitted, braided or woven mesh, the fibers of which may, if desired, be appropriately crimped to provide the required resiliency and compliance. The fiber mesh may be made of an alloy or a polymer material as further described in the application.

The invention in certain embodiments provides a venous graft (vein graft) for replacement of a section of an artery, where the graft comprises a flexible, resilient, generally tubular external support having a loosely knitted ("loose-knit") mesh structure, and a vein segment carried within and having an ablumenal surface in contact with and supported by the tubular support, the venous graft being capable of resilient radial expansion in a manner mimicking the compliance properties of an artery. The tubular support having a loosely knitted mesh structure having the required resiliency and compliance may further provide smoothening of irregularities, e.g., by reducing or eliminating differences between the outer diameter of a section of the stented vein segment and adjacent vein sections to provide a vein with an outer diameter substantially the same along its length. In certain embodiments, the tubular support having a loosely knitted mesh structure may exhibit limited shrinkage after graft implantation, providing further smoothening by post-implantation downsizing of the graft diameter. The loosely knitted mesh for use in the tubular support may be made of an alloy or a polymer material as further described in the application.

In other embodiments, the invention relates to a method for producing a venous graft (vein graft) for use, for example, in replacing a section of an artery. A segment of a vessel is provided, and is sheathed in a generally tubular support in supportive contact with the ablumenal surface of the vein segment. The support is sufficiently flexible and radially resilient as to provide the resulting graft with compliance properties mimicking the compliance properties of the artery to be replaced. Sheathing of the vessel segment within the tubular support may be accomplished by supporting the generally tubular support upon an exterior surface of an applicator having an internal passage within which is positioned the vessel segment, and removing the applicator to permit the tubular support to come into supportive contact with the ablumenal surface of the vessel segment. Axial dimensional changes in the tubular support may be controlled as necessary to provide the graft with the desired compliance properties mimicking arterial compliance properties. The tubular support may take the form of a fiber mesh as described herein, made of an alloy or a polymer material, chosen to optimize the compliance properties of the graft so that the stented graft is evenly compliant across variations in structure of the harvested vein segment.

Other embodiments of the invention relate to vessel grafts that include a flexible, resilient, generally tubular external support formed of a shape memory alloy, and a vessel segment carried within and having an ablumenal surface in contact with and supported by the tubular support. The shape memory support may be placed around a vessel segment when the shape memory material is in a first enlarged configuration. The tubular support comes into supportive contact with the ablumenal surface of the vessel when the support is transformed, as by a temperature increase or upon removal of an introducer tube over which the tubular support is supported, into a second configuration different from the first configuration. The shape memory support in its second configuration may exhibit superelastic properties and in any event is sufficiently flexible and resilient as to provide the venous graft with compliance properties mimicking the compliance properties of, for example, an artery. Compliance figures in the range of 3 to 30%/100 mm Hg are appropriate. The tubular support may take the form of a wire mesh made of shape memory alloy, such as a knitted or woven mesh, the wires of which may, if desired, be appropriately crimped to provide the required resiliency and compliance.

The invention is described hereafter primarily with respect to grafts that utilize veins that are received within a tubular support and that can function as replacements for arterial segments in, for example, coronary by-pass procedures, but the grafts of the invention may also utilize other vessels such as arteries, including treated vein and artery segments from donor animals such as vessels of porcine and bovine origin.

In certain embodiments, the invention relates to a method for selecting a stent for a venous graft, by measuring a minimum diameter and a maximum diameter of a vein, selecting a maximum amount of downsizing for the vein and a minimum amount of downsizing for the vein, calculating a range of diameters of stents that provide the an amount of downsizing between the selected maximum amount and the selected minimum amount, and selecting a single stent having a diameter that falls within the calculated range. The method can further include calculating a degree of downsizing for smoothening the vein, by altering an outside diameter of at least one part of the vein to be substantially the same as another part of the vein. In certain embodiments, the single stent selected by this method is the smallest possible stent within the range, resulting in maximum downsizing. In other embodiments, the single stent selected by this method is the largest possible stent within the range, resulting in minimum downsizing. In certain embodiments, the single stent selected by this method has a diameter of between about 2.7 mm and about 4.0 mm, more particularly between about 3.0 mm and 4.0 mm. In accordance with an aspect of the invention, the maximum amount of downsizing for the vein is the degree of downsizing for substantially smoothening the vein, where substantially smoothening the vein can include smoothening irregularities in the vein.

The invention in certain embodiments provides a stent including a generally tubular member constructed and arranged to receive a harvested vein segment, the generally tubular member being compliant so as to contract and expand with the vein, the tubular member having an inner diameter between about 2.7 mm and about 4.0 mm, or between about 3.0 mm and about 4.0 mm. In various non-limiting embodiments, the generally tubular member can be a knitted structure, where the knitted structure can be a metal wire, or a polymeric material, in particular an elastomeric polymer. In accordance with one aspect of the invention, the knitted structure can be configured to be shrinkable after receiving the harvested vein segment. In certain embodiments, the stent can include a plurality of connected rings, optionally interconnected rings, optionally wherein the rings are connected on outside surfaces of the rings.

In another embodiment, the invention provides a stent delivery device including a stent constructed and arranged to receive a vein segment, where the stent is compliant so as to contract and expand with the vein segment, and a delivery tube comprising a coating configured to impart slip properties to the tube to reduce traumatic introduction of the stent to an outside surface of the vein.

In another embodiment, the invention relates to a method of stabilizing a vein segment in a venous graft, the method by providing the vein segment, disposing the vein segment within a lumen of a stent constructed and arranged to contract and expand with the vein segment, where the stent has an inner diameter between about 2.7 mm and about 4.0 mm. In various non-limiting embodiments, the stent can have a knitted structure, where the knitted structure can be made of metal wire, or a polymeric material. In accordance with one aspect of the invention, the knitted structure can be configured to be shrinkable after receiving the harvested vein segment.

In one embodiment, the invention relates to a method for replacing a section of an artery in a patient with a venous graft capable of resilient radial expansion in a manner mimicking the compliance properties of a healthy artery in a patient. In accordance with this aspect, steps of the method can include, but are not limited to, restricting blood flow through the section of artery to be replaced, excising the section of artery to be replaced, leaving a first available artery end and a second available artery end in the patient, providing a vein segment having a first vein segment end and a second vein segment end, joining the first vein segment end to the first available artery end, providing a flexible, resilient, generally tubular external support stent capable of resilient radial expansion in a manner providing compliance in the range of 3 to 30%/100 mm Hg, sheathing the vein segment with the stent by introducing the second vein segment end into the stent and sliding the stent over the ablumenal surface of said vein segment until substantially all of said vein segment is carried within said stent; and joining the second vein segment end to the second available artery end provide said venous graft, wherein said venous graft is capable of resilient radial expansion in a manner mimicking the compliance properties of a healthy artery when blood flow is restored to said artery. In accordance with this aspect, the stent can be capable of said resilient radial expansion without significant axial dimensional changes. In accordance with another aspect, the stent can include a generally tubular fiber mesh capable of expanding in diameter through resilient movement of fibers of the mesh to accommodate radial expansion of the vein segment supported in it sufficient to provide the venous graft with the compliance. In certain embodiments, the stent includes a knit, tubular mesh capable of expanding radially to accommodate radial expansion of the vein segment supported in it, within said compliance range. In certain embodiments, the stent comprises a braided fiber mesh so configured as to exhibit radial expansion in said compliance range without significant reduction in the axial length of the stent. In certain embodiments, the fiber mesh is made of metal wire, optionally a shape memory alloy. In other embodiments, the fiber mesh is polymeric. In some embodiments, the ablumenal surface of the vein segment is bonded to said stent.

In one embodiment, the invention relates to a method for reducing intimal hyperplasia in an implanted vein segment following replacement of a section of an artery with a implantation of a venous graft comprising a providing venous graft comprising a flexible, resilient, generally tubular external support stent and said vein segment carried within the stent, where the vein segment has an ablumenal surface in contact with and supported by the stent, wherein the venous graft is capable of resilient radial expansion in a manner mimicking the compliance properties of a healthy artery when blood flows through the venous graft under physiological conditions. In certain embodiments, the stent support is capable of resilient radial expansion in a manner providing compliance in the range of 3 to 30%/100 mm Hg, and maybe capable of said resilient radial expansion without significant axial dimensional changes. In accordance with one aspect, the stent can include a generally tubular fiber mesh capable of expanding in diameter through resilient movement of fibers of the mesh to accommodate radial expansion of the vein segment supported in it sufficient to provide the venous graft with the compliance range, optionally a knit, tubular mesh or a braided fiber mesh.

In certain embodiments, the invention relates to a method for reducing intimal hyperplasia in an implanted vein segment by providing a venous graft with a knitted fiber mesh wherein the lumen diameter of said implanted vein segment does not increase significantly over time, i.e., remains substantially isodiameteric. In other embodiments, the method further includes shrinking the stent after disposing the vein segment within the lumen of the stent to smoothen irregularities in the vein segment. In other embodiments, the method further includes selecting a stent for the venous graft by measuring a minimum diameter and a maximum diameter of a vein from which the vein segment will harvested, selecting a maximum amount of downsizing for said vein and a minimum amount downsizing for the vein, calculating a range of diameters of stents that provide the amount of downsizing between the selected maximum amount and the selected minimum amount, and selecting a single stent having a diameter that falls within the calculated range.

BRIEF DESCRIPTION OF THE DRAWINGS

FIG. 5 is a photograph of a tubular support in a first configuration, shown in an axially compressed and radially expanded configuration and supported on a plastic tube;

FIG. 6 is a photograph of the tubular support of FIG. 5 in an axially elongated and radially reduced configuration to conform to a vein outer diameter;

FIG. 7 is a side view of the graft of FIG. 6, showing a length-governing element;

FIG. 8 is a schematic view of braided elements;

FIG. 9 is a perspective view of a braided tubular support;

FIG. 10 is a schematic view of knitted elements;

FIG. 11 is a side view of a section of a knitted tubular support;

FIG. 12 is a view of angular pre-braiding crimped elements;

FIG. 13 is a perspective, schematic view of an angular pre-braiding crimped tubular support;

FIG. 14 is a view of rounded pre-braiding crimped elements;

FIG. 15 is a view of angular pre-knitting crimped elements;

FIG. 16 is a view of rounded pre-knitting crimped elements;

FIG. 39 is a table listing the dimensions shown in FIGS. 37 and 38 of the knitted tubular supports of FIGS. 33-36;

DETAILED DESCRIPTION OF THE INVENTION

Applicants have recognized that significant deficiencies attend to the past methodologies and devices relating to the increased pressures experienced by vein grafts (venous grafts) utilized in arterial positions. The increased pressures lead to excessive dilation of vein grafts in arterial circulation, leading to the development of intimal hyperplasia, which causes occlusion of the vessel.

Intimal hyperplasia is believed to be a primary reason for vein graft failure. In this context it is known that intact endothelium acts in a manner to protect against the proliferation of underlying vascular smooth muscle cells, known as VSMC. The intact endothelium also plays a role in VSMC contractile responses. The VSMC have also been shown to release factors with long term physiological effects on the endothelial cells, including maintenance of a non-proliferative state. By comparison, the pathogenesis of intimal hyperplasia in a vein graft may follow the sequence of dilatation under arterial pressure; overstretching to maximum capacity; disruption of borders of endothelial cells; rupture of internal elastic membranes; migration of smooth muscle cells into the intimal layer and resultant unbalanced proliferation; atrophy of media and further consolidation of stiffness; and graft arteriosclerosis with traumatic media necrosis and atrophy, as well as pathological surface and wall stress and strain. These phenomena may result in a decrease in vein graft patency within six years. Intimal hyperplasia may be observed in such grafts from about 16 months, while anastomotic intimal hyperplasia may occur at about 18 months, and arteriosclerosis may occur from about 45 months.

Figure 1:
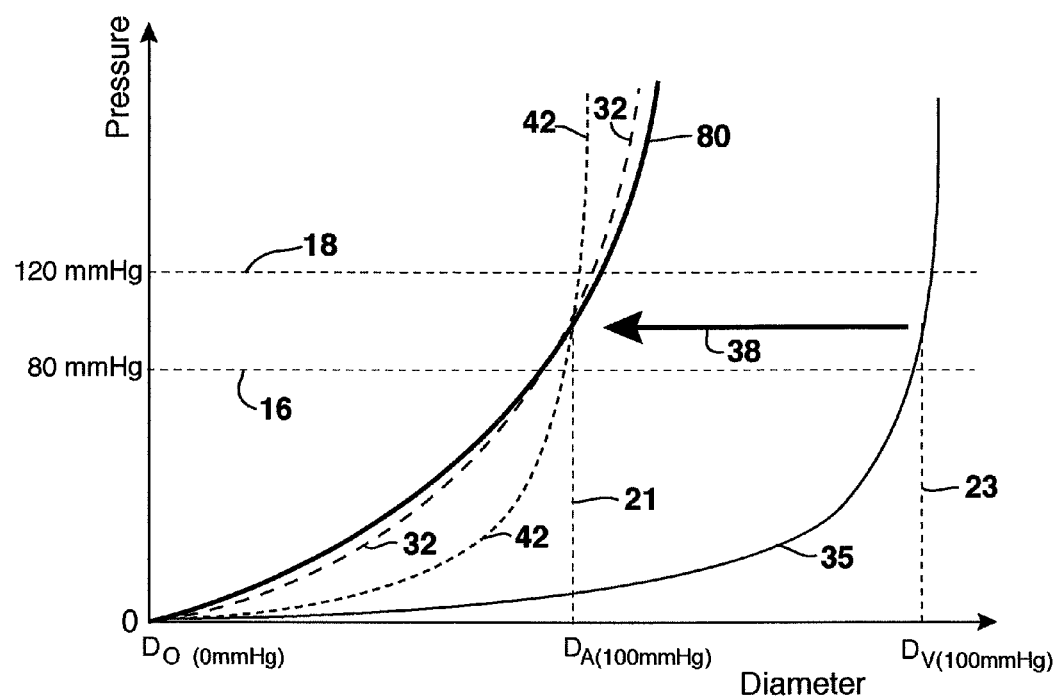
FIG. 1 is a pressure versus diameter graph typifying the characteristics of a native vein, native artery, a non-compliant stented vein, and a compliant stented vein.

Others have attempted to overcome certain of these problems by use of metallic or polymeric external structures designed to arrest the dilation of the vein graft. FIG. 1 graphs blood pressure against vessel diameter, with $D_O$ representing the vessel diameter at zero pressure. As shown in this graph, lines 16, 18 represent the normal diastolic, i.e. low (80 mm Hg) and normal systolic, i.e. high (120 mm Hg) physiological blood pressure range for humans. Line 21 may represent the diameter of an artery ($D_A$) at 100 mmHg, and line 23 may represent the diameter of a vein ($D_V$) at the same pressure of 100 mmHg. An unstented native artery reacts to pressure loading as shown at line 32, and an unstented vein reacts to the same loading as shown at line 35. The use of known stents with vein grafts results in movement of line 35 in the direction shown by arrow 38, resulting in the approximate profile indicated at line 42 showing the response of a pressure loaded vein and non-compliant stent combination. Although this prevents over-dilation, and some advantage accrues, this may lead to further unhealthy sequelae. Also, to the extent that vein-stent combination devices may be shown to limit some of the dilation and intimal hyperplasia in the mid-graft region, they may not be able to prevent intimal hyperplasia at the anastomoses. This can be a significant problem for vein grafts that are transplanted into the arterial circulation vasculature. Prior attempts to resolve these problems fail to recognize the full implications of a vein being used in these situations. Accordingly, factors in the design of a vein-graft that may have a significant impact on its long term patency may have been missed.

One important factor in proper remodeling is that of proper cyclic stretch. Applicants are able to incorporate this concept into vein-stent grafts of the invention. In similar manner, the role of vascular endothelial growth factor (VEGF) in vascular smooth muscle cells may be very important to the design of a preferred arterial vein-stent graft. It is known that low concentrations of VEGF may play a role in preserving and repairing the arterial lumenal endothelial layer. Further, it is suggested that activation of the VEGF receptor KDR is affected by cyclic stretch. Applicants believe that the phenomenon of upregulation of VEGF expression by physiological stretching of vascular smooth muscle cells is one reason for redesigning a vein-stent graft which has improved, controllable cyclic stretch features.

A further consideration is the influence of tensile stress/strain on the structure and organization of smooth muscle cells during development and remodeling, particularly as to the orientation of such cells. In a larger topographical sense, this may also relate to the role of blood flow in the formation of focal intimal hyperplasia in known vein grafts, including inducement of eddy blood flow at locations of graft-host diameter mismatch.

These considerations and deficiencies can be addressed with the various structures and methodologies of the present invention in which a vein graft is provided that exhibits compliance properties mimicking those of healthy arteries. Radial expansion and contraction of the graft is permitted in a manner that mimics the radial expansion and contraction of an artery to at least closely approach the desired result in which the vein graft, its connections to adjacent arterial ends or stumps, and the adjacent arterial portions tend to expand and contract in a similar manner, to thereby substantially avoid anastomotic compliance mismatches. This is accomplished through the use of a flexible, resilient, generally tubular external support that engages the ablumenal surface of a vein segment carried within the support, the support being so fabricated as to functionally provide the graft with the compliance properties of an artery.

Compliance Properties

As noted earlier, compliance is the ratio of the diameter change of a vessel in the radial direction to a given change in vessel pressure, and the values for compliance referred to below result from dynamic, in vitro testing. Compliance values are reported here as percentage changes in the internal diameter of a vessel per a 100 mm Hg change in vessel pressure, as measured in the range of normal blood pressures, that is, from about 80 mm Hg to about 120 mm Hg. In the laboratory, it is convenient to measure compliance through the use of an elongated balloon structure over which a candidate tubular support is positioned. Distilled water at about 37° C. is pumped into the balloon to cause it to inflate, and the pressure within the balloon is cycled between 0 mm Hg and 140 mm Hg at a frequency of about 72 cycles per minute to mimic a normal pulsatile blood flow. The change in internal volume is measured between 0 mm Hg and 140 mm Hg to provide pressure/volume data. From this data is subtracted the pressure/volume data resulting from repeating the procedure with the balloon alone, and from the resulting pressure/volume data the percentage change in the internal diameter of the tubular support between 80 and 120 mm Hg can be calculated. It is convenient to express this radial compliance value as %/100 mm Hg.

The compliance of an implanted venous graft may be measured in vivo through the use of ultrasound techniques in which the vein graft is visualized in a cross-sectional view and the dimensional change of the vessel with varying blood pressure is recorded for at least one and usually a number of cardiac cycles. The cross-sectional lumenal area of the vein graft is measured for the smallest cross-sectional configuration and the largest cross-sectional configuration for one cardiac cycle. The smallest cross-sectional configuration of the vein graft lumen is associated with diastolic blood pressure whereas the largest cross-sectional configuration is associated with systolic pressure. The cross-sectional lumenal area values for diastolic and systolic blood pressure are used to calculate the lumenal diameter values and the vein graft compliance. Compliance values of a venous graft measured in vivo often are slightly larger that the compliance values measured in the laboratory, and the compliance values referred to herein are laboratory values resulting from the in vitro measurements described above.

Figure 2:
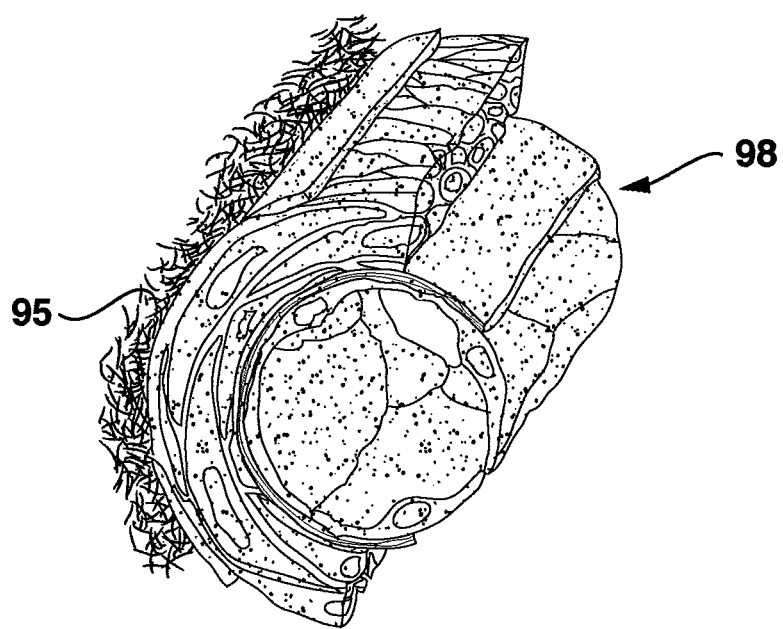
FIG. 2 is a schematic cross-sectional view of an artery.

FIG. 2 is a sectional representation of vascular tissue useful for illustrating the relation of the natural arterial structure with the prosthetic venous graft structure of the invention. The natural adventitial layer 95 of an artery 98 is comprised of two main tissue types that contribute to the mechanical properties of the natural artery, namely elastin and collagen. The mechanical properties of these two soft tissue components are described in Table I below:

TABLE I

Mechanical Properties of Soft Tissue Components

| Soft Tissue | Elastic Modulus (Pa) | Max Strain (%) |
|---|---|---|
| Elastin | $4 \times 10^5$ | 130 |
| Collagen | $1 \times 10^9$ | 2-4 |

Figure 3:
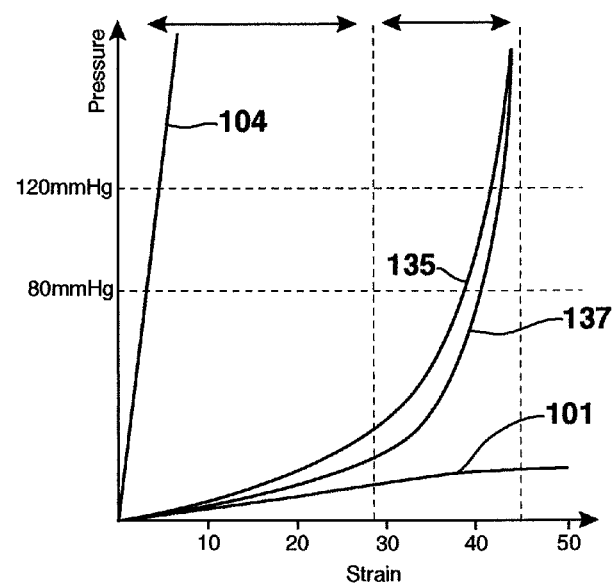
FIG. 3 is a representative pressure versus strain graph.

As shown in the above table, these two soft tissue types have large differences in mechanical properties. Elastin is very elastic, and collagen is very stiff in comparison. These two tissue types are combined in the adventitial layer to produce a non-linear elastic response. As shown in FIG. 3, the combined effect of the characteristics of elastin 101 and collagen 104 (having a greater role at higher strains) results in a non-linear response curve (shown loading at 135 and unloading at 137) within the physiological pressure range of a natural artery between about 80-120 mm Hg. This characteristic of pulsatile expansion and contraction of arteries requires fine mechanical compliance of any prosthetic graft, i.e., a close mimicking by the prosthetic device of the mechanics and timing of the natural artery distending and reshaping under change in blood pressure.

From an engineering standpoint, the following relationships may be helpful from a design standpoint in producing venous stent grafts of the invention.

$$C_d = \frac{\Delta D}{D_{diastolic} \cdot \Delta P} \cdot 100 \cdot 100 \text{mm} Hg \qquad (1)$$

in which $C_d$ is compliance, P is blood pressure, $\Delta P$ is the difference between systolic and diastolic blood pressures, D is vessel diameter, and $\Delta D$ represents the diameter change between systolic and diastolic pressures.

The stiffness of blood vessels is stated as a stiffness index ($\beta$), and is a measure of the changes of curvature and diameter, stated as:

$$\beta = \frac{\ln\frac{P_{systolic}}{P_{diastolic}}}{\frac{\Delta D}{D_{diastolic}}} = D_{diastolic}\frac{\ln P_{systolic} - \ln P_{diastolic}}{\Delta D} \quad (2)$$

A related characteristic of blood vessels is that of elastic modulus (K), which is considered a measure of stiffness, and is stated as:

$$K = \frac{V_{diastolic} \cdot \Delta P}{\Delta V} \propto \frac{D_{diastolic} \cdot \Delta P}{\Delta D} \propto \frac{1}{C} \quad (3)$$

in which C is compliance, $V_{diastolic}$ is the vessel volume per unit length at diastole, and $\Delta V$ is the difference in unit volumes between systole and diastole. In terms of diametric compliance, as an example, $$K = D_{diastolic}\frac{P_{systolic} - P_{diastolic}}{D_{systolic} - D_{diastolic}} = D_{diastolic}\frac{\Delta P}{\Delta D} \quad (4)$$

Figure 4:
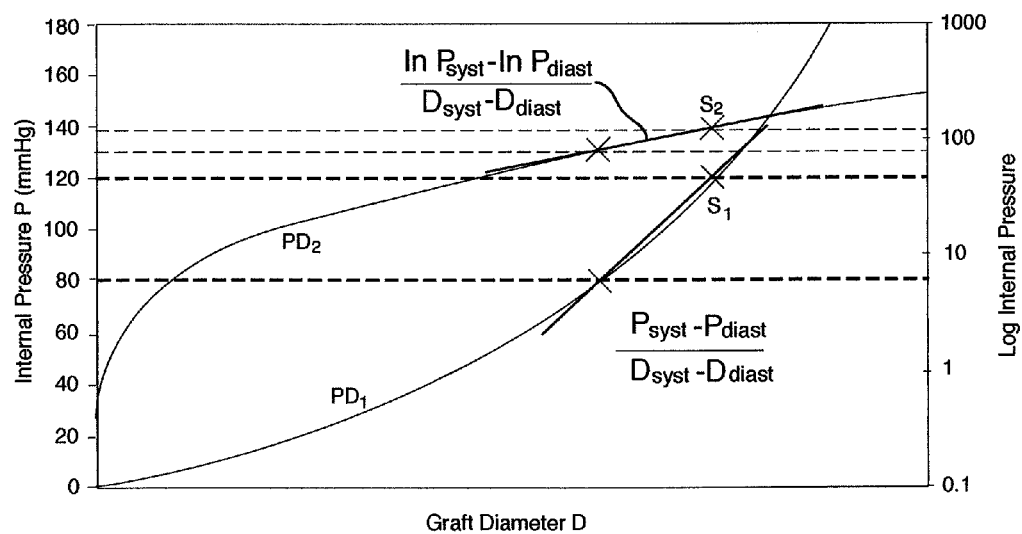
FIG. 4 is a pressure versus graft diameter graph.

FIG. 4 shows that the Elastic Modulus (K), as defined in the above equations, is proportional to the secant $S_1$ of the pressure-diameter curve $PD_1$, plotted on a linear scale (left y-axis in FIG. 4), between diastolic and systolic pressure. The slope, $(P_{syst}-P_{diast})/(D_{syst}-D_{diast})$, of the secant $S_1$ is a good approximation to the slope of the pressure-diameter curve $PD_1$ in that pressure range. From the above equations for the Elastic Modulus (K) it can be appreciated that the Elastic Modulus (K) is not equal to the slope of the secant $S_1$ but is proportional to the slope by a factor $D_{diastolic}$. Compliance ($C_d$) is approximately proportional to the Elastic Modulus (K) hence it is approximately proportional to the inverse of the secant $S_1$ of the pressure-diameter curve $PD_1$ between diastolic and systolic blood pressure.

The stiffness index ($\beta$) is proportional to the secant $S_2$ of the pressure-diameter curve $PD_2$ between diastolic and systolic blood pressure when the pressure-diameter curve is plotted on a logarithmic pressure scale (right y-axis in FIG. 4). The slope of the secant $S_2$ is $(\ln P_{syst} - \ln P_{diast})/(D_{syst}-D_{diast})$ and is a good approximation to the slope of the pressure-diameter curve $PD_2$ in that pressure range. It can be again appreciated, from the above equations for the Stiffness Index ($\beta$) that the Stiffness Index ($\beta$) is not equal to the slope of the secant $S_2$ but is proportional to the slope by a factor $D_{diastolic}$.

Compliance data of natural human vessels is categorized by vessel type and by age of the vessel (i.e., age of patient). For example, a common carotid artery has about a 6.6%/100 mm Hg compliance value. The values for a superficial femoral artery and a femoral artery are 6-10%/100 mm Hg. A value for a saphenous vein, however, is about 4.4%/100 mm Hg, while an aorta ranges generally from about 20-50%/100 mm Hg, depending on the location. Also, the lengths of grafts according to location in the body must be considered, and substantial lengthwise variance in graft lengths is not uncommon. It is also known that the diameter of various arteries change over time, and this may have a significant impact on overall compliance values. Returning to FIG. 1, line 80 represents the pressure-diameter data that certain embodiments of venous grafts of the invention seek to emulate, wherein the compliance properties of a native artery (line 32) is closely mimicked.

Support Materials and Manufacture

The radially resilient support may be manufactured from any biologically acceptable material that possesses the ability to be shaped into a tubular structure having the required compliance. Polymeric fibers may be employed, such as polyurethanes, polyethylene terephthalate, polypropylene, and polytetraflouroethylene, and good results may be obtained through the use of wires of such metals as stainless steel and cobalt-chromium alloys. Polymeric fibers may be elastomeric polymers, e.g. polyurethane elastomers or composite fibers that act in an elastic fashion. Polymeric fibers may be "shrinking" polymers, where the shrinkage may be controllable, e.g., pressure-sensitive polymers. Wires made of shape memory alloys such as Nitinol may be used to advantage. Shape memory elements or filaments may be made of one or more shape memory materials as exemplified in Table II below, it being understood that this is not to be considered an exhaustive list. Also, any metal or metal alloy may be coated with a polymer for improved biocompatibility, recognizing that the polymer may or may not be biodegradable.

TABLE II

| Materials | |
|---|---|
| ALLOYS | POLYMERS |
| Ag—Cd | Two component system based on oligo($\Sigma$-caprolactone)dimethacrylate and N-butyl acrylate |
| Au—Cd | Polyurethanes |
| Cu—Al—Ni | Polynorborenes |
| Cu—Sn | Poly(ether ester)s consisting of poly(ethylene oxide) and poly(ethylene terephthalate) (EOET copolymers) |
| Cu—Zn | Ethylene vinyl acetate copolymers |
| Cu—Zn—Si | Polystyrene polybutadiene copolymer |
| Cu—Zn—Sn | |
| Cu—Zn—Al | |
| In—Ti | |
| Ni—Al | |
| Ni—Ti | |
| Fe—Pt | |
| Mn—Cu | |
| Fe—Mn—Si | |

With respect to shape memory alloys, other design considerations include temperatures, different diameters and radial compliance, shape transformation dimensional changes, and wire thicknesses. Generally, shape memory alloys and shape memory polymers may have transformation temperatures which are below physiological temperatures, i.e., 37° C., to ensure self-righting responses. Preferably, transformation temperatures will also be above room temperature to ensure that the shape memory material reinforcing does not need to be refrigerated for storage purposes. Thus, the ideal shape memory transformation temperatures will likely be between 21° and 37° C. This transition may either be a two-way or a one-way directional transition, with a currently preferred embodiment including a two-way directional transition. The transition temperature range can either be a short, i.e. 0.5° C., or a long transition temperature range, i.e. 10° C., where the shape is proportionally regained over this temperature range.

For example, for a desired temperature transition to be 100% complete at 25° C. but with it starting at 20° C., then this would yield a temperature range of 5° C. The changes in radial diameter due to the shape memory material experiencing transformation dimensional changes is preferably in a range of from 5% to 30%.

An embodiment of a tubular support utilizing a shape memory alloy is illustrated in FIGS. 5 and 6. FIG. 5 shows an arterial reinforcement tubular support 77 formed of one or more shape memory material elements 165. These elements are braided, but may also be knitted or woven, into a generally tubular structure designed for placement around a portion of a vein to produce an arterial graft. In this example, a shape memory alloy is employed because of its so-called "superelastic" properties rather than its ability to undergo temperature-induced phase changes, although some phase change from austenite to stress-induced martensite may occur. In FIG. 5, the braided tube is positioned on a hollow plastic straw as representing a vein segment, and has been compressed axially to produce an increase in diameter. By extending the braided tube axially, as shown in FIG. 6, the tube becomes reduced in diameter to provide support to the vein segment.

The shape memory braided material shown in FIGS. 5 and 6, if used also for its phase transformation properties, may be supplied in a first configuration (which may be in the martensite phase) which can be easily manipulated to receive a vein segment 86 within the structure, and a second configuration (shown in FIG. 6, which may be in the higher temperature austenite phase) which has a "remembered" narrower diameter configuration to provide support to the vein segment. The contact of inner surfaces 170 of the structure with abluminal surfaces 175 of the vein segment 86 is shown also in FIG. 7. The resilience of shape memory materials can be controlled by altering compositions, tempering procedures, wire diameters, etc., so that a tubular support fashioned from this material may mimic (when combined with the minimal mechanical values of a vein segment) the compliance values of a host artery in order to optimize the venous graft-artery interaction. This aspect of compliance mimicking has components of expansion, recoil, timing, and tissue remodeling. In this example, the vein-stent compliance values are chosen to closely mimic those of a healthy native artery. Whereas the shape memory wires are shown as braided in FIGS. 5, 6 and 7, they may also be knit, and in fact the knit configuration appears to offer certain advantages.

Radially resilient tubular supports may be knit from metal wire, such as stainless steel and cobalt-chromium alloys. Metal wires ranging in diameter from about 25 to 150 micrometers are appropriate for knit supports with diameters in the range of 35 to 50 micrometers being particularly useful, although larger or smaller diameters may be employed as desired. For braided tubular supports, metal wires ranging in diameter from about 37 to about 170 micrometers are appropriate, although larger or smaller diameters may be employed.

Figure 21:
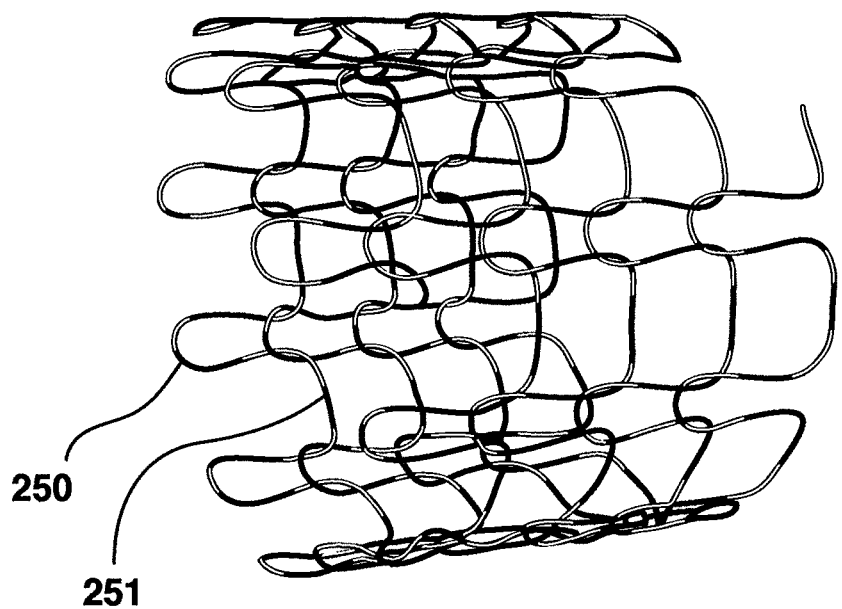
FIG. 21 is a perspective view of a section of a knit tubular support.

Knitting procedures may be performed by known methods using, for example, a LX96 knitting machine manufactured by the Lamb Knitting Machine Corporation. Favorable radial compliance and tubular dimensional properties may result from knitting the tubular structure in a manner providing loops that alternate in the circumferential direction between larger and smaller loops, as shown in FIG. 21. In this Figure, smaller loops 250 are shown alternating circumferentially with larger loops 251. Such alternating loop sizes typically present themselves visually as longitudinal stripes extending axially along the tubular support, as the adjacent loops of each size align in the longitudinal axis. Each closed end of the loop may be either rounded or generally square-shaped or variations in between, and, the sides of the loop may turn outward, be parallel, or turn inward. The latter design has shown some advantage in acting like a spring and assisting in the stability of the overall dimensions of the tubular structure, and maintaining its compliance characteristics.

Other geometries for the loops in the knitted structure are contemplated. Additional embodiments are illustrated in FIGS. 33-36. The number of loops per circumference is determined by the number of needles used during the knitting process. The number of loops per longitudinal unit length and the similarity or dissimilarity of circumferentially neighboring loops is controlled by various parameters of the knitting process. From experimental data obtained with various Nitinol knit tubular structures, it is suggested that the mechanical and structural properties of the knit tubular structure are controlled to a certain degree by the geometrical features of the knit mentioned above. These geometrical features include, but are not limited to the similarity/dissimilarity of circumferentially neighboring loops and number of loops per longitudinal unit length.

Figure 33:
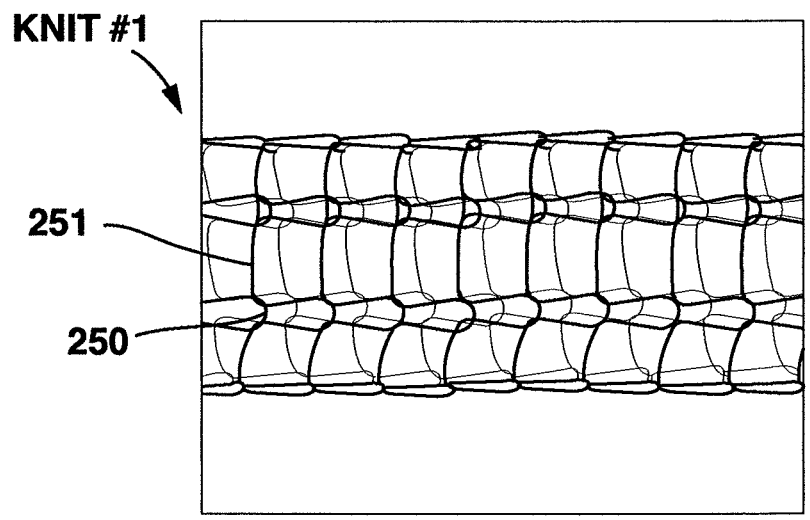
FIG. 33 is a side view of a section of another embodiment of a knitted tubular support.
Figure 34:
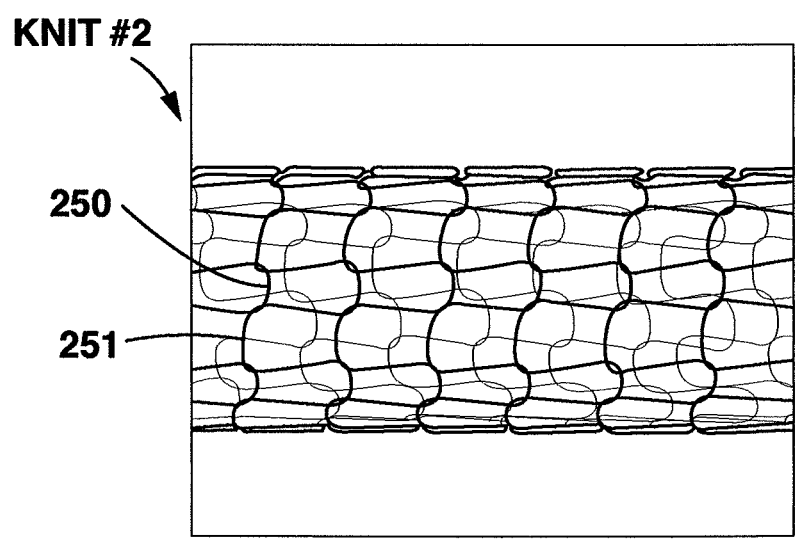
FIG. 34 is a side view of a section of another embodiment of a knitted tubular support.
Figure 35:
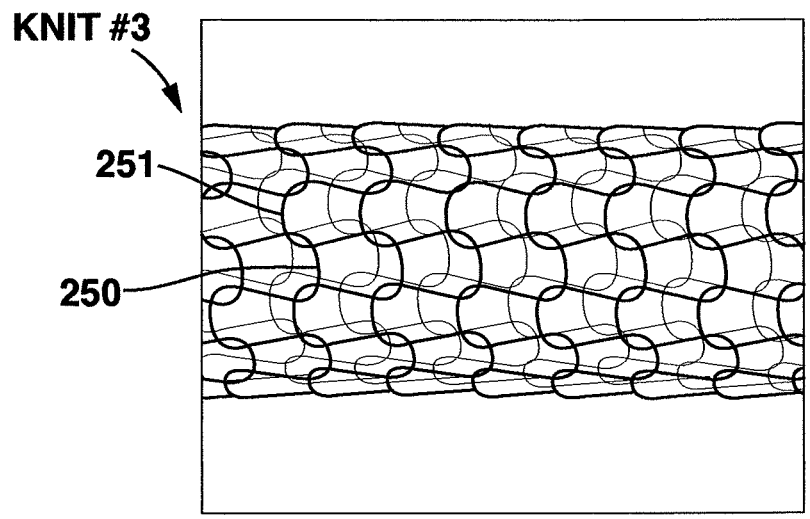
FIG. 35 is a side view of a section of another embodiment of a knitted tubular support.
Figure 36:
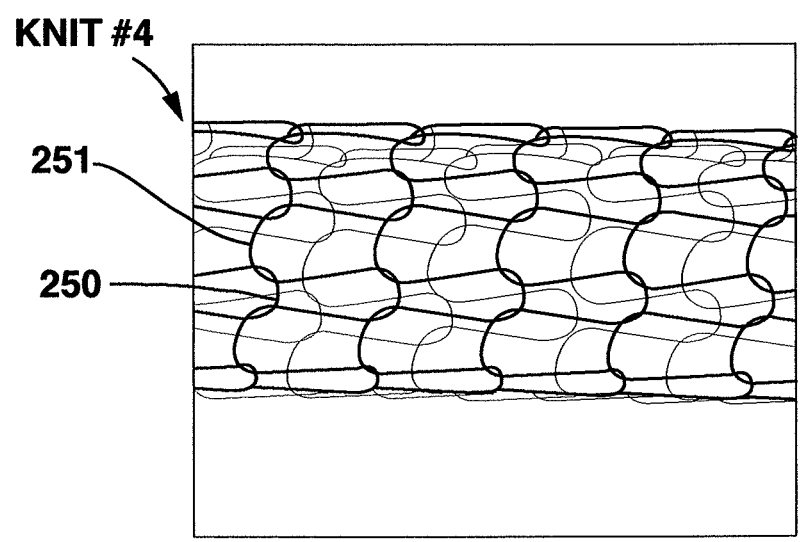
FIG. 36 is a side view of a section of another embodiment of a knitted tubular support.

Tubular knit structures with different degree of dissimilarity of circumferentially neighboring loops are shown in FIGS. 33-35. FIG. 33 shows high degree of dissimilarity (highly uneven neighboring loops), FIG. 34 shows an intermediate degree of dissimilarity (intermediate uneven neighboring loops), and FIG. 35 shows a low/zero degree of dissimilarity (even neighboring loops). FIG. 36 shows a knit structure with larger loop length in longitudinal direction of the knit compared to the structures shown in FIGS. 33 to 35. A larger longitudinal loop length results in a lower number of loops per longitudinal unit length, e.g. per inch in longitudinal direction.

Figure 37:
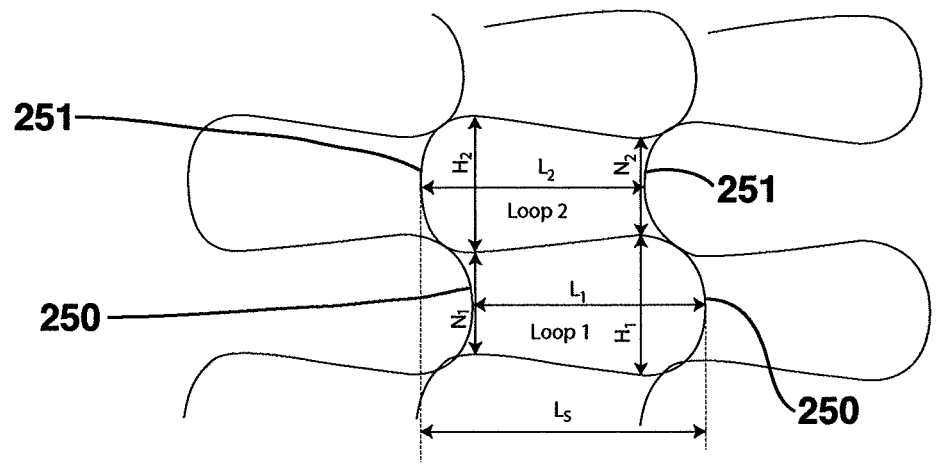
FIG. 37 is a schematic view of a section of a knitted tubular support showing various dimensions of the support.
Figure 38:
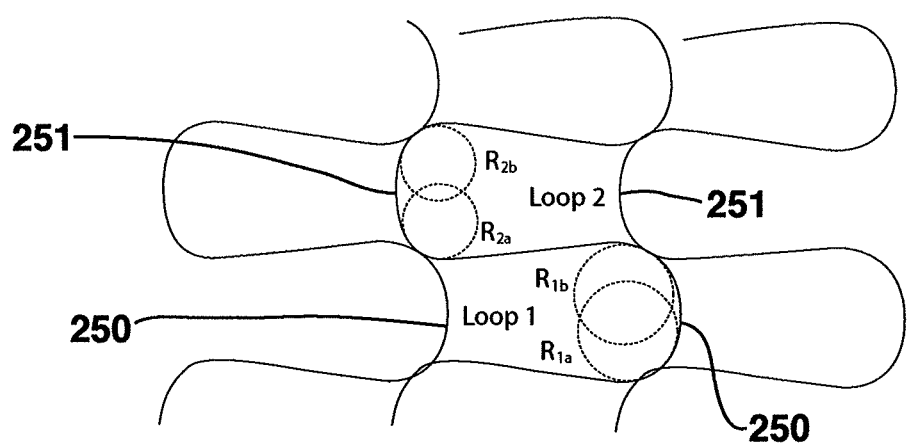
FIG. 38 is another schematic view of the knitted tubular support of FIG. 37 showing other dimensions of the support.

FIGS. 37 and 38 illustrate the dimensional parameters used to specify the geometry of a neighboring pair of loops, both with respect to the dissimilarity of neighboring loops and the longitudinal loops length. The dimensional parameters are measured digitally in macroscopic photographs of the knit structures, such as shown in FIGS. 33 to 36. Since the tubular structure has a circular cross section, linear measurements in the photographs in transverse/circumferential direction of the knit deviate from the actual circumferential dimension. The deviation depends on, and varies with, the transverse distance from the mid axis of the knit. Dimensional parameters subject to this deviation are all except those in longitudinal direction, i.e. $L_1$, $L_2$ and $L_S$. The deviation of the transverse/circumferential parameters $H_1$, $N_1$, $H_2$, $N_2$ are numerically corrected after completion of the measurements. The deviation correction includes the outer diameter of the knit, transverse distance between the knit mid axis and the start and end point, respectively of each measurement. The table in FIG. 39 gives measured and corrected dimensional parameters for Knits #1 to #4 (shown in FIGS. 33 to 36) as an example.

The dimensional parameters measured on macroscopic photographs of manufactured prototypes can be employed to specify particular loop geometries and to perform dimensional 'quality' control of prototypes of the same loop design manufactured in different batches. This may require the dimensional parameters to be measured in macroscopic photographs of prototypes of the newly manufactured batch. These measurements would then be compared with the measurements of the original prototype. Dimensional loop geometry measurements on existing tubular knit prototypes may also serve as basis for knits with modified loop geometries, e.g. with a different degree of dissimilarity of neighboring loops or different longitudinal loop length.

Figure 17:
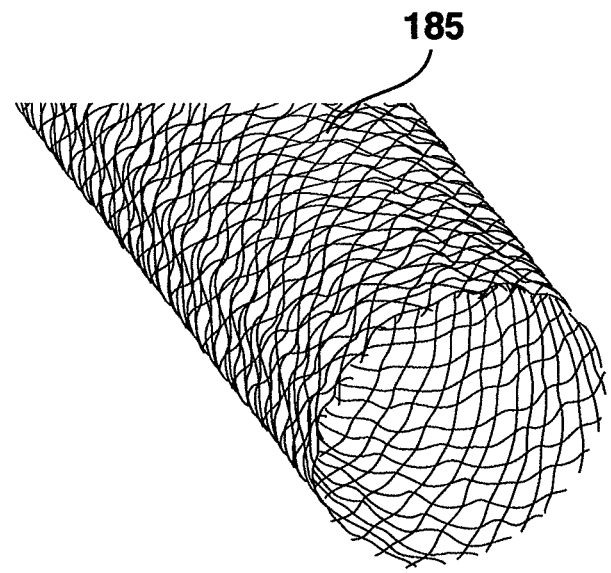
FIG. 17 is a broken-away, perspective view of a post-braiding crimped tubular support.

Regardless of how the tubular support is manufactured, the knitted or braided tubular support may then be subjected to crimping to provide crimps extending, for example, about the circumference of the tubular support (that is, in the manner shown in FIG. 17). One way of doing this is through the use of an axially fluted mandrel that is inserted into the tube and is pressed outwardly against a wall of the tube to force the wall against a complementary shaped outer female mold to bend the knitted or braided wires and to form a circumferential crimp, the crimp resulting from each flute or raised ridge of the mandrel extending axially of the support.

A compliant venous graft using various metals or polymers for the tubular support may be provided in several ways. Embodiments may be advantageously provided in knitted form. FIGS. 8 and 9 show material 165 in a braided configuration, and FIGS. 10 and 11 show material 165 in a knitted configuration. Mechanical characteristics of the tubular support may be enabled by the type of shaping and relational structures formed on the elements making up the knit or braided structures. It is contemplated that a technique involving crimping of the material 165 to achieve angular crimps (shown in FIGS. 12 and 13), formed prior to the braid or knit construction, and rounded crimps (shown in FIG. 14) may provide acceptable results. Crimping techniques that may be appropriate with pre-knit configurations are shown in FIG. 15 (angular crimps) and FIG. 16 (rounded crimps). Another technique for achieving certain performance characteristics of braided or knitted shape memory materials 165 is to perform crimping after braiding or knitting, i.e. post-braiding or post-knitting. FIG. 17 shows one embodiment of material 165 formed in a braided configuration and having a post-braided crimping operation applied to form a crowned pattern to achieve desired crimp characteristics.

Crimp angle and pitch density may be important variables in certain embodiments of the current design of the tubular supports. It is understood, however, that certain advantages of this invention may still be achieved without use of crimping. Ranges of crimp angle are preferably from about 10° to 85° to the line of lay of the reinforcing wire or braid. The crimp size may vary from 0.01 to 5 mm in length. It is desired that the braid or helical wires have a pitch angle that may vary from about 5-85° to the axial length of the vein graft.

Applicants have identified certain crimping techniques that relate to crimping either before or after braiding or knitting. For example, in post-braid crimping the material braids are produced according to existing techniques, after which macroscopic longitudinal crimping is imparted to the tubular mesh using a post-braid crimping tool. However, according to the material and specific configuration of the stent, if the post-braid crimping of braided tubes does not achieve sufficient compliance then alternate methods are possible. One example is to effect pre-braid crimping, thereby setting the memory of a shape memory material in a crimped configuration and subsequently straightening the material before braiding. The crimp is thus induced upon exposure to physiological temperatures.

Figure 40:
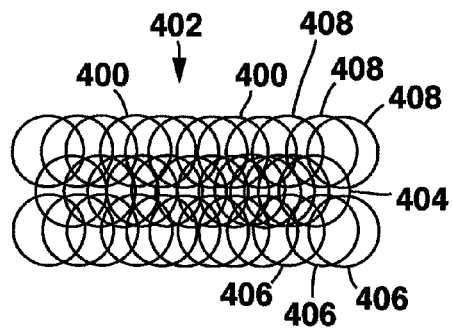
FIG. 40 is a schematic view of another embodiment of a tubular support.
Figure 41:
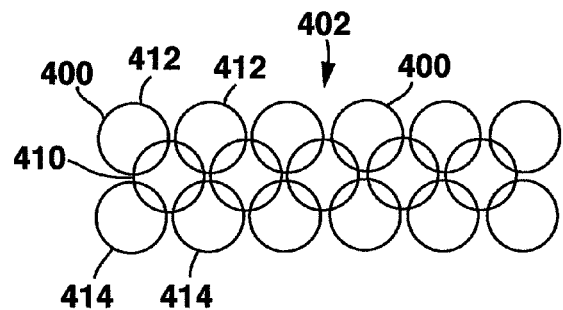
FIG. 41 is a schematic view of another embodiment of the tubular support of FIG. 40.

In other embodiments, rather than having a knit or braided structure, the graft may include a plurality of rings 400 that are connected together to form a tubular structure, as shown in FIGS. 40-43. The rings 400 may be made from any suitable material, such as the metals, alloys, and polymers discussed above. As shown in FIGS. 40 and 41, the rings 400 may be interlinked together so as to form a continuous chain 402. FIG. 40 shows only a portion of the structure in an unrolled state, and illustrates a configuration in which a central ring 404 connects three rings 406 on one side thereof with three rings 408 on the other side thereof. Such a connection may be used throughout the tubular structure. FIG. 41 also shown only a portion of the structure in an unrolled state, and illustrates a configuration in which a central ring 410 connects two rings 412 on one side thereof with two rings 414 on the other side thereof.

Figure 42:
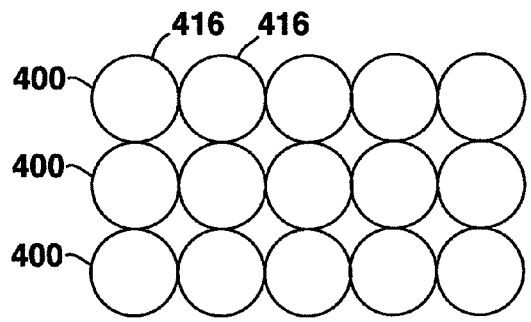
FIG. 42 is a schematic view of another embodiment of a tubular support.
Figure 43:
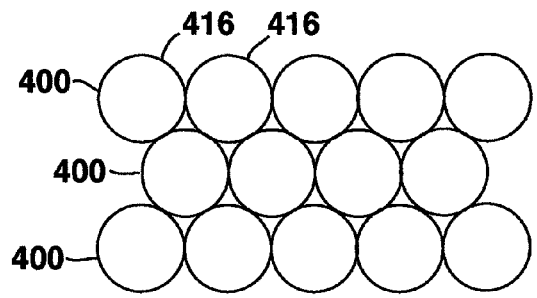
FIG. 43 is a schematic view of another embodiment of the tubular support of FIG. 42.

In another embodiment, rather than being interconnected in a chain-link fashion, the rings 400 may be connected at their outer surfaces 416, as shown in FIGS. 42 and 43. The rings 400 may be welded together, where the rings are made of a metal or alloy material, or may be connected with any suitable adhesive, especially in embodiments that include rings made from a polymer material. In the embodiment illustrated in FIG. 42, the rings 400 are connected so that no single ring contacts more than four other rings, i.e., the rings are connected at surfaces that are disposed 90° from each other. In the embodiment illustrated in FIG. 43, the rings 400 are connected so that no single ring contacts more than six other rings. This configuration provides a more tightly packed structure, as illustrated in FIG. 43.

Of course, any suitable number of rings may interconnected or connected, so long as the resulting structure provides the compliance and performance properties of the grafts and stents discussed herein. Properties of the resulting stent may be altered by varying the pattern of the rings, the internal diameter of each ring, the thickness of each ring, etc. Compliance of the resulting stent may be achieved by the deformation of the rings into oval shapes upon an application of force. It is also contemplated that the rings within a single stent may have different properties, e.g, different diameters, thicknesses, shapes, and materials, and that the rings may be combined with the knitted patterns discussed above. The illustrated embodiments are not intended to be limiting in any way.

In certain embodiments, it is appropriate to provide for "jump" grafts, or "skip" grafts to communicate a stented graft with another vessel. To accommodate such grafts, an opening is made in the resilient, external tubular support of a compliant graft of the invention so that a portion of the vessel wall itself is exposed through the opening to enable a jump graft to be attached at that location. It is desirable to provide for such openings in the support wall prior to assembly of the compliant graft. When the tubular support is made of a shape memory alloy, such as Nitinol, an opening in the mesh may be made by supporting the mesh on an appropriately shaped mandrel and gently moving the fibers forming the mesh away from what is to be the center of the opening. A pin or other support is placed in the opening to keep it open, the pin being held and supported by the mandrel. The tubular support, constrained in this shape, is subjected to a heat treatment, e.g., in the 500° C. range, for a short period of time and then cooled. The resulting tubular support, in its austenite phase, exhibits the usual super elasticity associated with Nitinol and other shape memory alloys, and the opening thus provided in the wall of the tubular support remains open and accessible for formation of a jump graft. By selection of an appropriately shaped and sized tubular support with a pre-formed access opening, a surgeon may produce a graft prosthesis having an opening in the wall of the tubular support positioned where desired for formation of a jump graft.

The external tubular support adjusts the mechanical and geometrical properties of the vein graft to match or mimic healthy arterial properties and therefore adapt to the arterial pressure of the host artery. Accordingly, this results in substantial matching of the lumen of the vein graft and the host artery, the substantial matching of compliance of the vein graft and the host artery, and substantial matching of the radius to wall thickness ratio (r/wt) of the vein graft to the host artery. As noted above, optimization of the vein-stent compliance should ensure that the vein-stent graft mimics the behavior of arteries regarding the non-linear stiffening with increasing diameter due to elevated blood pressure, "locking" at a maximum pressure, and then demonstrating dynamic recoil in a timely manner.

Figure 18:
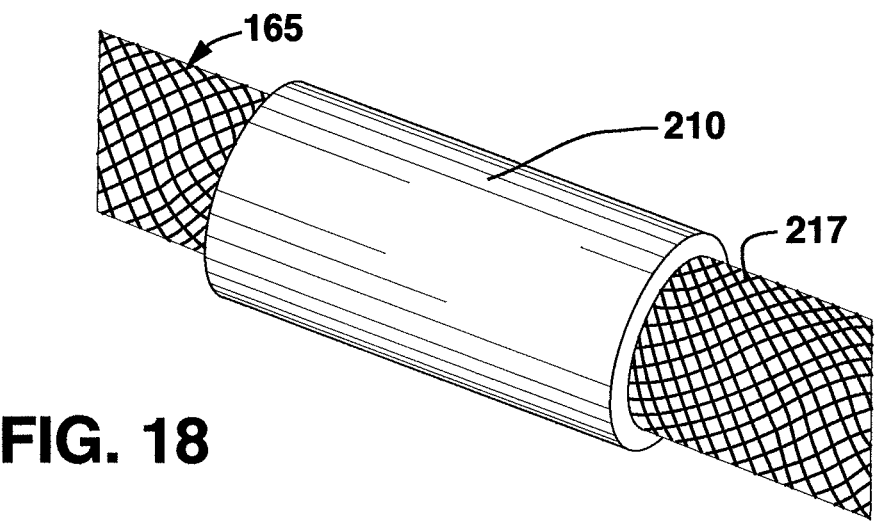
FIG. 18 is a broken-away, perspective view of a venous graft showing a portion with anti-fraying element.

When venous grafts utilizing knit or braided tubular supports are cut at angles suitable for end-to-end anastomoses, either at generally right angles or in scallop-like shape, the ends of the supports may experience fraying (see, for example, FIG. 17). Certain methods and structure are helpful to eliminate such fraying. In one embodiment, adjustable rings 210 of bioabsorbable or biodegradable material are placed generally circumferentially around a portion of the material 165, and in contact with external surfaces 217, as shown in FIG. 18. The number of rings may be varied as needed. The location of the rings may be adjusted to the position of anastomoses where vein and tubular support need to be cut. The cut or suture may be carried out through the ring, and the ring may be absorbed or degraded over a predetermined time, as desired.

Another embodiment of a structure to prevent fraying of a knit or braided tubular support when it is cut is the use of polymer coating for the fiber mesh. This feature may also provide the benefit of preventing gluing of joints and contact zones of elements of the stent. However, use of the radially compliant tubular support as a reinforcing structure may advantageously involve bonding of the ablumenal surface of a vein segment to confronting internal surfaces of the support. This attachment or connection may be accomplished through the use of a glue or other material having adhesive or connecting characteristics. In one embodiment, a fibrin glue or other material having adhesive or connective characteristics may be sprayed on designated portions of the vein (as exemplified at 283 in FIG. 20) and/or the tubular support. The fibrin glue may be an autologous fibrin glue or autologous platelet gel, as described in U.S. Pat. Nos. 6,444,228 and 6,596,180, which are both incorporated herein by reference in their entireties.

The adhesives, whether synthetic or natural, may be applied by spraying, brushing, sponging or dripping the material onto the stent/graft construct, or applied by the applicator. To prevent fraying of a knitted or braided structure, the stent may be pre-coated, by dipping, spraying, brushing, etc., with an elastomeric material that binds the individual wires together in such a manner that it prevents fraying at ends/cut edges while maintaining compliance. The material can be of synthetic (polyurethane, silicone, polyvinyl alcohol) or natural origin (fibrin gels, collagen gels, albumin etc). As an extension of this embodiment, the material used to prevent fraying may further effect adhesion of the stent to the vein/graft by incorporation of reactive groups capable of reacting with the graft/vein ablumenal surface. It is also contemplated that selective spot welding of wire and material patches may be used to prevent fraying of a knitted or braided structure.

In embodiments pertaining to adhesion and antifraying, the gels/glues/adhesives that are used may further contain bioactive agents that are released (either by diffusion from a non-degradable adhesive or by release from a degradable one) to effect a desirable biological response. For example, growth factors may be incorporated to stimulate and increase the vascularization (formation of additional vasa vosora) that in turn result in improved outcomes. In an embodiment, steroids may be released to minimize the foreign body reaction to the stent/adhesive material(s).

Another embodiment includes placement of a material on designated portions of the lumenal surfaces of the tubular support so as to provide the characteristics of contact adhesion and/or bonding when these portions contact the vein. However, the glue or other material must not inhibit the function of the tubular support. It is desirable that the contact of the tubular support with the ablumenal vein segment surface be reasonably uniform along the length of the support, and that regions of much higher force of the support against the ablumenal wall of the vein be avoided.

Performing the anastomoses of small-diameter unsupported vein grafts in the coronary position is complicated by the tendency of the free end of the vein to collapse on itself, thereby obscuring the lumen and making it difficult for the surgeon to identify a suitable position for the placement of sutures. The application of an external tubular support (referred to sometimes herein as a stent) on a vein graft potentially further complicates the suturing, as the collapsed vein is situated inside (and at least partially obscured by) the non-collapsed stent material. By attachment of the ablumenal surface of the vein to the lumenal surface of the stent, however, the stent offers support to the vein to prevent it from collapsing, and this is particularly the case when stents formed from shape memory alloys are employed. As noted above, adjustable rings 210 and various adhesives may be employed to bond the confronting surfaces of the vessel and the supporting tubular structure together.

Figure 24:
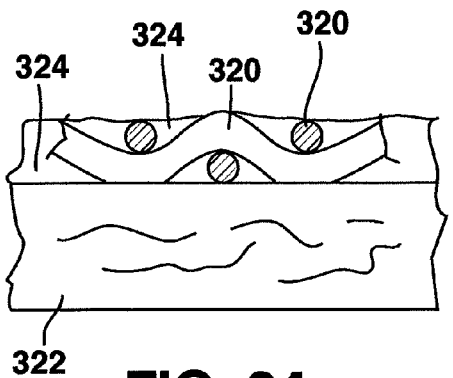
FIG. 24 is a schematic cross-section of an attachment of a vessel to a tubular support.
Figure 25:
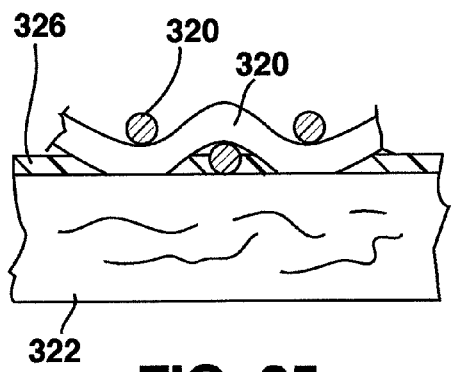
FIG. 25 is a schematic cross-section of another attachment of a vessel to a tubular support.

Attachment of the vessel surface to the tubular support stent can be achieved in various ways. In one embodiment, a covering gel is employed that attaches to the vessel wall and surrounds and entraps the stent wires, thereby attaching the stent to the vessel, this embodiment being schematically depicted in FIG. 24, the tubular support fibers being shown at 320, the vessel wall at 322 and the gel at 324. Examples of such gels are synthetic gels (such as modified polyethylene glycol, polyvinyl alcohol, acrylic gels, etc) and biological gels (such as fibrin, gelatin, and albumin glues). In another embodiment shown schematically in FIG. 25, an adhesive glue 326 such as a cyanoacrylate attaches the stent to the vessel ablumenal wall, the glue adhering to both the vessel and the stent.

Figure 26:
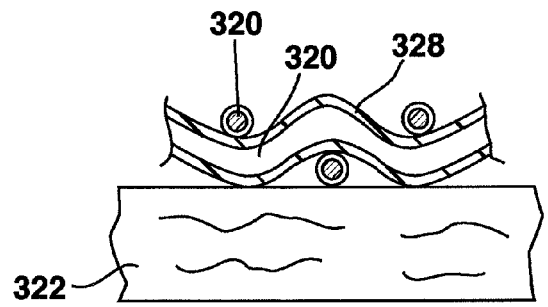
FIG. 26 is a schematic cross-section of yet another attachment of a vessel to a tubular support.

In another embodiment, shown schematically in FIG. 26, individual fibers 320 of the stent are coated with an adhesive material 328 containing groups reactive to the vessel tissue. This material may be either directly applied on the metal wires (FIG. 26) or on a polymeric coating with which the wires are pre-coated. This material coating, applied optionally over a polymer coating on the wires, may also be employed in other embodiments, for example, those shown in FIGS. 24, 25, 27 and 28.

Figure 27:
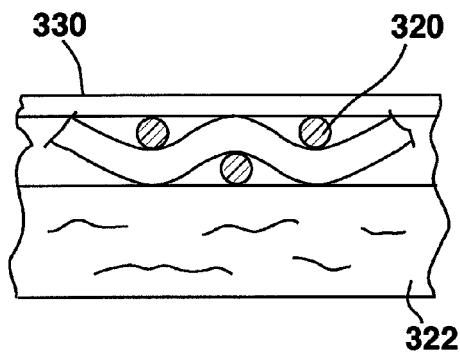
FIG. 27 is a schematic cross-section of the attachment of a vessel to a tubular support utilizing a sleeve.
Figure 28:
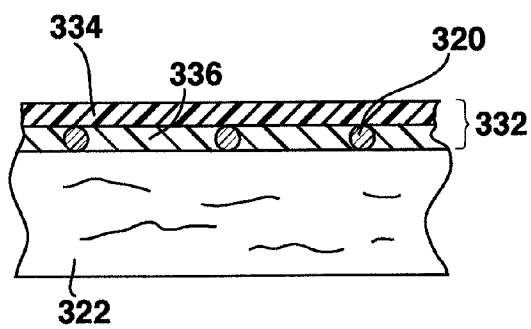
FIG. 28 is a schematic cross-section of the attachment of a vessel to a tubular support utilizing an adhesive tape.

In a preferred embodiment, a sleeve is placed over the assembled stented vessel. As schematically depicted in FIG. 27, the sleeve 330 may primarily offer mechanical support for the stent to prevent fraying of cut edges, in the manner discussed above in connection with FIG. 18, while having minimal if any effect on the mechanical properties of the assembly, such as compliance. Referring to FIG. 28, a sleeve may comprise an adhesive tape 332 having an elastic backing material 334 bearing an adhesive material 336 having a consistency enabling it to penetrate between fibers of the tubular mesh and adhesively contact the ablumenal surface of the vessel. The adhesive may have the consistency of a gel. The elastic material may be a fabric, and may be formed from a variety of materials that are inherently elastic (e.g. polyurethane elastomers) or materials that are not elastic by themselves, but may act in an elastic fashion due to the fact that they are coated with or entrapped in an elastic gel-like material that constitutes the adhesive portion of the tape. Crimped fibers made from polyesters (PET) or degradable materials such polylactic acid (PLA) or polyglycolic acid (PGA) or copolymers thereof may also be used for the elastic material.

The adhesive material 336 should be of sufficient cohesive strength and adhesive strength to the vessel wall by virtue of mechanical interlocking and/or covalent chemical binding to attach the stent to the vessel during normal handling during implantation. As the vessel tissue contains both nucleophilic (amino, thiol and hydroxyl groups) and electrophilic (carboxyl) groups, the adhesive may employ a number of chemical groups capable of reacting with the vessel wall. Aldehydes, acyl chlorides, activated esters, isocyanates or carboxylic acids (plus activators such as carbodiimides) are examples of compounds capable of reacting with nucleophilic groups on the tissue, and alcohols and amines may be employed to react with the electrophilic carboxylic acid groups on the tissue (in the presence of an activator, e.g. a carbodiimide).

In general, the adhesive may be composed of synthetic polymers, in their swollen or unswollen states. Gel-like characteristics may be imparted by the adhesive material itself, or by swelling the material with a solvent or a plasticizing agent, such as water. Gels offer the advantages of having viscoelastic properties that may simulate the mechanics of vessels to some extent, and of being capable of deforming to facilitate contact and binding of the gel to the tissue through the gaps in the stents. In addition, gels may contribute to the strength of the bond between the vessel wall and the stent by mechanical interlocking. Adhesives may be non-degradable cross-linked materials such as polyethylene glycols, polyimines, polyacrylates (e.g., polyacrylic acid, polyacrylamides, poly(hydroxyethyl methacrylate), and co-polyacrylates. Degradable and/or resorbable adhesives may include multifunctional polyethylene glycols containing degradable end groups and/or crosslinked with degradable crosslinkers, and non-crosslinked or lightly crosslinked polyvinyl alcohol.

As noted above, the adhesive material desirably is functionalized with groups capable of reacting with the vessel tissue. For example, an adhesive may comprise crosslinked polyacrylic acid gels functionalized with aldehyde groups (e.g., via a diamine bridge) capable of reaction with tissue amines. As another example, a polyvinyl alcohol, the degree of hydrolysis, molecular mass and tacticity (and thus crystallinity) have been adjusted to render the adhesive slowly dissolvable in vivo can be appropriately functionalized with groups reactive toward tissue groups.

Figure 29:
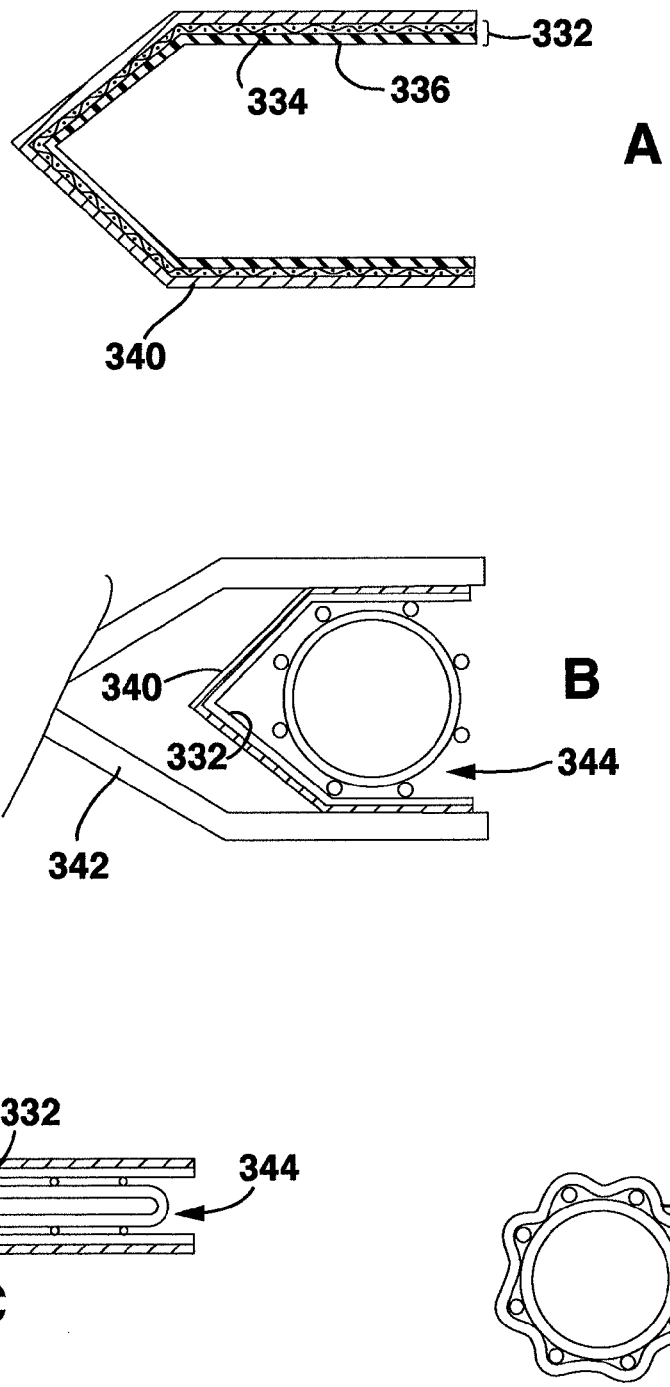
FIG. 29A is a cross section of a clip bearing an adhesive tape segment.
FIGS. 29B through D are schematic views showing stages in the application of an adhesive tape segment to a vessel graft.

Although the adhesive tape 332 may be applied as desired to the stented vessel, a preferred method involving particular stented vessels having a supportive tubular structure derived from a shape memory material utilizes a pre-assembled clip comprising a disposable elastic metal clip and a segment of the adhesive tape, as schematically depicted in FIGS. 29 A through D. Referring to FIG. 29A, the metal clip 340 is shaped to provide an opening for reception of the stented vessel, and may, for example, be generally "C" shaped. The clip contains within it a section of the adhesive tape 332, the adhesive surface 336 facing the interior of the clip and the elastic backing adjacent the inside surface of the clip. As desired, the assembled clip may be positioned within the jaws of a pliers-like applicator 342 (FIG. 29B). In use, a section 344 of a stented vessel is inserted into the opening of the clip as shown in FIG. 29B. The jaws of the applicator 342 are closed on each other, the stented vessel becoming temporarily flattened as shown in FIG. 29C and the adhesive penetrating between fibers of the stent to adhesively contact the ablumenal surface of the vessel. The jaws of the applicator are opened, enabling the section of the stented vessel to resume its substantially circular cross-sectional configuration. The metal clip is removed, and excess tape is removed from the edges to provide the stented tube structure schematically shown in FIG. 29D.

An alternative method involves the employment of a tape dispenser that contains a continuous roll of the tape, sections of the tape being severed from the roll and applied to the stented vessel by hand.

Figure 30:
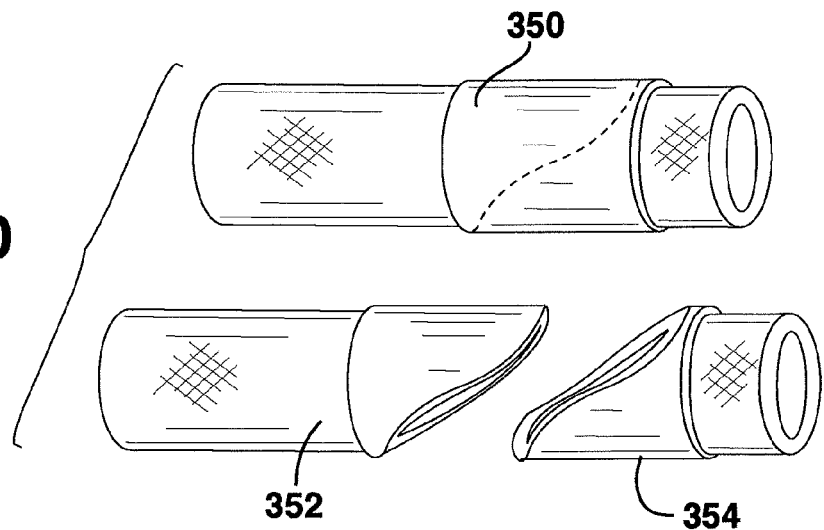
FIG. 30 is a schematic view showing severance on a bias of the vessel graft also shown in FIG. 29D.
Figure 31:
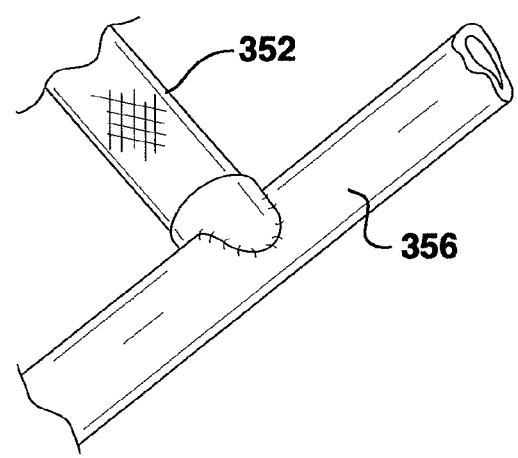
FIG. 31 is a schematic view of the attachment to an artery of a segment shown in FIG. 30.

The application of the tape to the stented vessel can be performed at a position required by the surgeon according to the implant position. FIG. 30 shows how a taped section 350 of a stented vessel may be cut to provide a biased opening that may be sutured to, for example, a coronary artery. The taped section is cut so that the resulting open end is configured to conform generally to the ablumenal surface of an artery or other vessel to which the stented vessel is to be attached. FIG. 30 shows a cut being made generally along the dashed lines to provide segments 352, 354. FIG. 31 shows how the bias-cut taped end of the segment 352 may be sutured to a length of artery 356, and it will be understood that the artery has a surgically prepared, axially extending slit (not shown) providing an opening through its wall about which the segment 352 is sutured to communicate the graft with the artery.

By appropriately cutting the taped portion, the end of the segment can be shaped to conform as needed to the external contour of various vessels to which it is to be attached. For example, a graft may be shaped to make an appropriately angled (e.g., 45 degrees) juncture with a coronary artery, the artery and the stented graft segment lying generally in the same plane. In another example, the stented graft may cross over a vessel to which it is to be attached. In this "cross-overjump" configuration, slit-like openings are provided in the taped section of the graft segment and the vessel, and the taped section and the vessel are sutured together about their confronting openings and to establish fluid communication through the openings. The slit-like openings may be made such that they are approximately parallel as they confront each other. In yet another example, the stented graft and a vessel may be positioned substantially parallel and in contact with each other. In this "longitudinal jump" configuration, slit-like, desirably axially extending openings are made in the taped section of the stented graft and in the vessel, and suturing is performed as above.

Figure 19:
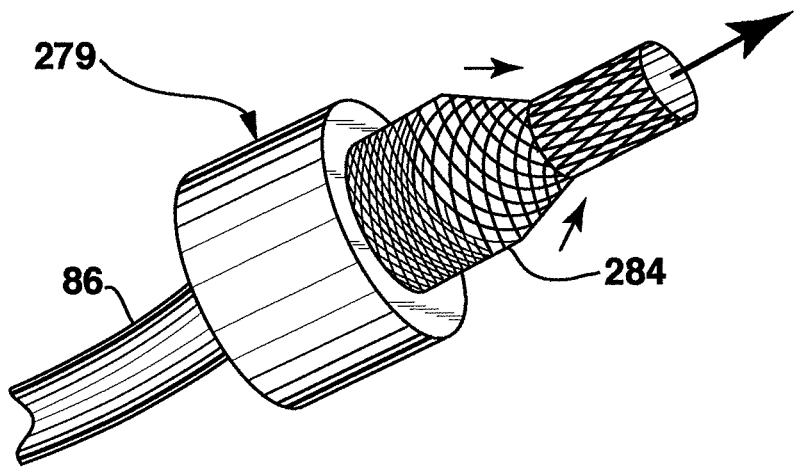
FIG. 19 is a broken-away, perspective view of one embodiment utilizing an applicator for assembling a venous graft.

Applicants have further recognized the need for a device to facilitate assembly of the radially compliant tubular support and a vein segment. It is desirable that such an applicator should not obscure the stent lumen, and that it should allow for easy insertion of the vein. It is further recognized that a design whereby diameter is increased by length compression, as in a braided configuration, would allow easy slipping of the tubular support over a vein. FIG. 19 illustrates this concept in combination with an applicator 279 to apply the braided support 284 to a vein 86. This longitudinal braid contraction phenomena (shown earlier in FIGS. 5 and 6), and which must be carefully managed at the time of joining the vein to the stent, is likely quite useful to achieving the goals of an applicator 279, as noted above. This applicator may also facilitate placement of anti-fraying rings 210. In one embodiment, the method of using the applicator comprises the steps of: providing the means of longitudinally contracting a stent; holding the stent in the contracted position with increased stent diameter resulting; inserting a vein into the stent lumen; and distending the stent longitudinally while the vein is inserted simultaneously until the stent is slipped over the desired portion of the vein. Further design considerations must ensure that the stent will not be fixed to the vein in a longitudinally over-distended or contracted state, so as to ensure that the predetermined mechanical stent properties remain viable.

Figure 20:
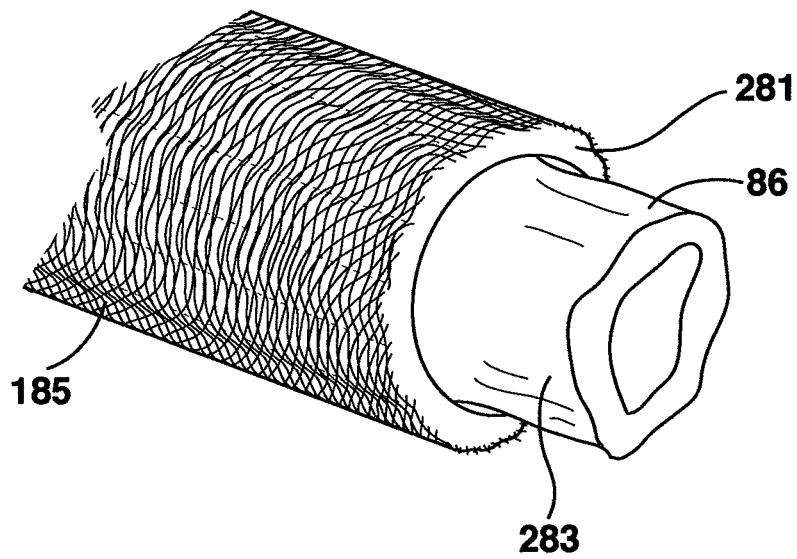
FIG. 20 is a broken-away, perspective view of the use of a modified applicator for assembling a venous graft.

FIG. 20 shows an embodiment in which a tubular support 185 is received along the outer surface of an applicator 281 having an internal passage, and, while passing the vein segment 86 from within the applicator passage, the tubular support is drawn onto the ablumenal surface of the vein segment. The applicator here may be a thin walled tube resembling a soda straw.

Figure 22A:
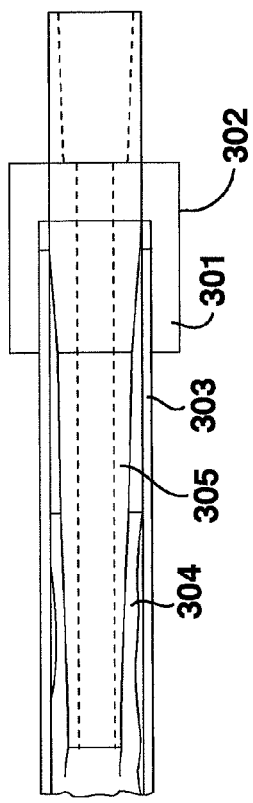
FIG. 22A is a schematic cross-sectional view of an assembly device.

FIGS. 22A and B show the end of a syringe 300 having a mechanism 302 for engaging and immobilizing the end of a blood vessel and the surrounding tubular support. The mechanism may be any mechanism adapted to connect to the ends of open tubes, and one such mechanism may include an outer tubular portion 301 within which is received an end portion 304 of a blood vessel, the mechanism including an axially movable internal tapered mandrel 305 that is inserted in the vessel. Axial movement of the mandrel (to the left in FIG. 22) pinches and captures the end of the blood vessel between the mandrel and an introducer sheath carrying a tubular support, the sheath and tubular support together being shown in FIG. 22A as 303.

Figure 22B:
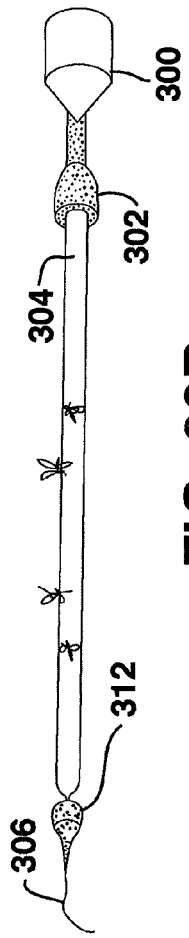
FIG. 22B is a schematic, prospective view of a step in the assembly of a vessel graft.
Figure 23:
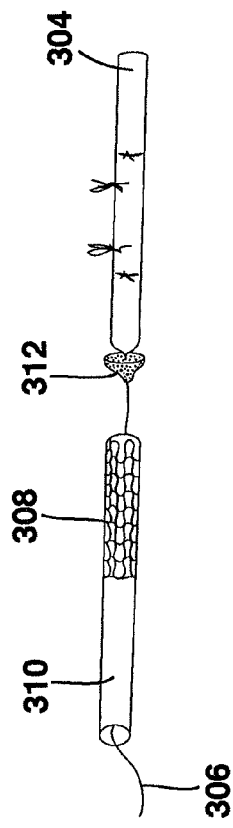
FIG. 23 is a schematic, prospective view of another step in the assembly of a vessel graft.

Referring to FIGS. 22B and 23, in one assembly method, the distal end 304 of the vessel is supported by the mechanism 302 with the proximal end of the vessel being attached to a cord 306. The tubular support 308 (FIG. 23) is carried exteriorly of and is supported by an introducer tube 310. A plug 312 sized to engage the interior wall of the introducer tube is attached to the proximal end of the vessel. The introducer tube 310, bearing on its outer surface the tubular support 308, is drawn over the cord 306, the plug and the vessel segment, the cord being maintained under tension to facilitate sliding the introducer tube over the vessel. The end of the tubular support is gripped by the mechanism 302 (FIG. 22A). Thereafter, the introducer tube is withdrawn proximally away from the mechanism 302. By frictionally engaging the interior surface of the introducer tube, the plug 312 exerts a gentle longitudinal tension on the proximal end of the vessel, causing the vessel to shrink somewhat in diameter. As the introducer tube is withdrawn, the tubular support 308 comes into contact with the ablumenal surface of the vessel. Once the introducer tube has been completely withdrawn, the gentle longitudinal tension on the vessel is relaxed and the vessel itself seeks to return to its original larger diameter to thereby more closely contact the tubular support.

The plug may be made of any appropriate material that frictionally engages the interior wall of the introducer tube as it is withdrawn, and a soft urethane rubber plug, for example, may be employed.

Although assembly of the stented graft has been described as occurring away from the vein or artery to which it will eventually become attached, in practice, such assembly can be affected by attaching one end of the harvested vessel segment to the artery or vein with a cord attached to its other end. The mesh tubular support is then urged gently over the ablumenal surface of the vessel while maintaining gentle tension on the cord until the support is positioned where desired.

It is desired that the support be applied to a vein at a predetermined length which is associated with a particular desired compliance. A length-defining support feature or system should ensure a predetermined support length. This is particularly true with respect to braided supports, and perhaps less important with knit supports in which radial resilience is less dependent upon the amount to which the support is extended axially.

In a braided support, and to a much lesser extend in a knit support, compliance and related mechanical properties are linked to the support length through the pitch angle. Imparting a change in length results in a change in pitch angle and compliance. However, the compliance of the support is a mandatory characteristic which is optimized, as noted above, to mimic the compliance of a normal healthy host artery. When applying a support to a vein segment, it is important to accurately accommodate the predetermined tubular support length, even after longitudinal contraction of the support for the attachment of the support to the vein.

With braided, and to a much lesser extent knit supports, axial support length may be controlled, for example, through the use of an axially extending, relatively inextensible element, (as for example the thread 78 in FIG. 7), that restrains the tubular support from unwanted axial extension. The thread may be woven through the support mesh and may be fastened, as by welding, to the various wires that the thread encounters along the length of the support so that as the support is stretched axially, the extent of axial elongation is controlled by the thread as the thread is drawn taut. Moreover, this feature may enable a length of the tubular support to be divided into portions of appropriate length, with the permitted axial extension of each portion controlled by the section of thread within it. As presently envisioned, a vein segment may be sheathed in a tubular support as discussed in detail above, with the intent of cutting out a smaller segment of the resulting venous graft for use in the surgical replacement of an artery, and the venous graft that is thus used will have vein and tubular support ends that are coextensive.

Various generally tubular external wire mesh supports were fabricated from metal wires by braiding and by knitting, some being crimped and others not, and the diametrical compliance of each was measured using the in vitro diametrical compliance testing outlined above. The measured compliance values were dependent upon many variables, including wire size, tightness of braid or knit, etc. The following values listed in Table III were obtained:

TABLE III

Compliance Values

| Design | | Compliance %/100 mmHg |
|---|---|---|
| A | Braided Non-crimped | 0.9 |
| B | Braided Crimped | 5.6 |
| C | Braided Crimped | 1.8 |
| D | Knitted Non-crimped | 3.4 |
| E | Knitted Crimped | 7.9 |
| F | Knitted Crimped | 8.0 |
| G | Knitted Non-crimped | 10-21 |
| H | Knitted Non-crimped | 9-21 |
| I | Knitted Non-crimped | 16->30 |
| J | Knitted Non-crimped | >30 |
| K | Knitted Non-crimped | 10-16 |
| L | Knitted Non-crimped | 21-29 |
| M | Knitted Non-crimped | 22-28 |
| N | Knitted Non-crimped | >30 |
| O | Knitted Non-crimped | 10-15 |
| P | Knitted Non-crimped | 9-11 |
| Q | Knitted Non-crimped | 13-24 |
| R | Knitted Non-crimped | >30 |

A surgical procedure is proposed for use of the graft disclosed herein. This procedure, which may also be viewed as a simple method for placement of a venous reinforcement structure, includes, in this example, application of the compliant external tubular support during the procedure of vein excision. In many instances, vein excision is considered a standard part of a surgical operation, which is usually done by an assistant at a time when the surgeon is still in the preparatory phase of the operation. When an autologous blood vessel such as a segment of the saphenous vein is harvested for use in accordance with the invention, it may contain side branches that need to be removed before the vein is enclosed within the tubular support. Closure of the opening that remains after removal of a side branch can be accomplished in several ways. Surgically placed sutures or small clips such as Liga clips may be used to ligate small sections of branches. However, when a branch has been removed flush with the ablumenal Surface of the vessel, it is desirable to close the resulting opening in the vessel by suturing to reduce interference with the tubular support. Purse string sutures are appropriate. To avoid undue narrowing of the lumen of the vessel when a purse string suture is pulled tight, the ends of the purse string suture are preferably tightened by pulling them in the longitudinal direction, i.e., axially of the vessel, rather than in a direction transverse to the longitudinal direction of the vein.

In one embodiment, an initial step includes dissection and freeing of a saphenous vein. The saphenous vein is dissected free in a standard way, leaving it in situ while ligating and cutting off its branches as discussed above. The second step involves testing for potential wall leaks of the vein. In order to test the isolated saphenous vein for potential leaks, it is normally cannulated distally and cold heparinised blood is injected while the proximal end is occluded. This inflation of the vein (using old techniques) with a syringe creates pressures of up to 350 mm of Hg and is often a main reason for traumatic damage of the vein wall. Therefore, a pressure limiting mechanism may be positioned between the vein cannula and the syringe. The external tubular support cannot be applied yet because leaks in the vein wall need to be freely accessible for repair. Therefore, no over-distention protection is placed around the vein yet, necessitating the limitation of the inflation pressure to a level suitable for detecting any leaks of concern but less than a level deemed to cause unacceptable damage, such as, for example, in one embodiment, 15 mm of Hg, the pre-maximal dilatation pressure for veins. The tissue remodeling functions of applicants' invention become more critical in view of the importance of leak testing and the reality of possible damage to the intimal layer in the vein during even the most carefully performed leak testing.

The next step involves assembling the harvested vein segment and an external tubular support of this invention. In this step, the tubular support (typified here as a knit support) is mounted on a tube or straw-like applicator within which is positioned the vein segment. See FIG. 20. The tube or straw-like applicator may be pre-treated with a lumenal slip coating to minimize friction between the vein and the applicator as the applicator is positioned over the vein segment, thereby minimizing stretch injury to the vein. The applicator is then removed axially, leaving the support and vein in contact to form the venous graft. Over-extension of the tubular support is prevented using a length-limiting central thread or other means, as described above. As required, the vein segment is then inflated under arterial blood pressures of 120 mm of Hg, causing it to contact the tubular support inner lumenal surfaces. In certain embodiments, an adhesive securing the tubular support to the vein will ensure that the vein does not collapse during the surgical procedure when no internal pressure is applied. Again, it should be recognized (without limitation) that this is one of several ways to accomplish the above objectives.

The following sequence may occur at this or another time during the procedure. One of the external anti-fraying rings or cuffs is slid to the end of the vein, and a typical double-S-cutting line is used to prepare the end for the first anastomoses. The thin cuff prevents fraying of the tubular support and also gives the vein tissue and tubular support a uniformity which makes the surgical process of stitching the vein to the host artery in an end-to-side fashion much easier. Another thin anti-fraying ring is then slid down from the applicator to a position where either a side-to-side anastomoses for a sequential graft is being performed, or where the vein is being cut at an appropriate graft length. The half of the sliding cuff which remains on the original vein will make the process of the anastomoses to the proximal host artery much easier. In the case of a coronary artery bypass graft, for example, the end of the remaining vein protected by the other half of the cuff is used for the next distal graft anastomoses.

Although the invention has been described primarily in connection with the use of autologous blood vessels to form a stented graft as a replacement for diseased vessels, the invention has other uses as well. External stent structures can be used to allow repeated access to the vascular system for administration of medicines or nourishment or the administration of dialysis procedures. Exterior access grafts may be subject to frequent penetration by hypodermic needles, and it is desirable not only that the vessel walls of the graft retain their capacity to be punctured many times, but also that the wounds thus formed in the vessel wall self-seal to a large extent. In addition, for example, the stent structure on its own may be added to veins to increase competency of venous valves.

Figure 32:
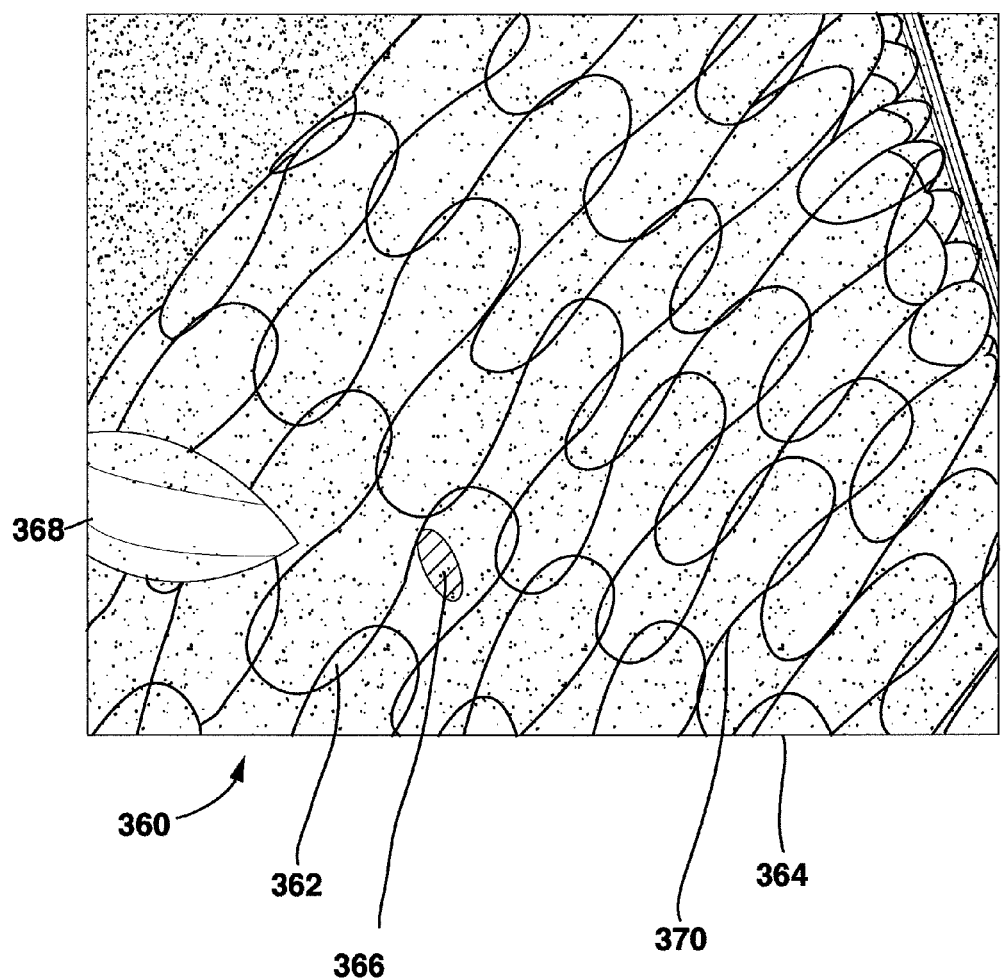
FIG. 32 is a photograph of a portion of a bioprosthetic access vessel graft.

In accordance with the invention, an external stent structure 360 as shown in FIG. 32 may be produced from a blood vessel segment harvested from human or non-human animals, such as segments of bovine or porcine arteries, the vessels having been treated, as by known aldehyde fixing or decellularization. A flexible, resilient tubular support of the type described herein may be placed over the resulting venous or arterial vessel segment to provide a bioprosthetic access graft to enable ready access to the cardiovascular system. For this purpose, one may form a bioprosthetic device utilizing a suitably treated bovine or porcine artery or vein segment by placing the segment within an elastic, resilient tubular support sized to contact and squeeze against the ablumenal surface of the vessel when the vessel is filled with blood, as when it is being used as a shunt between an artery and a vein of a patient. In this manner, once a hypodermic needle has been inserted and withdrawn from the wall of the vessel, the elastic, resilient tubular support tends to exert a squeezing force on the vessel, forcing the edges of the wound to close upon one another.

FIG. 32 is a photograph showing an access graft formed from a decellularized porcine artery segment 362 contained within a knitted, resilient tubular support 364. This figure illustrates a puncture wound 366 formed by a syringe 368. The edges of the wound are brought together by the squeezing action imparted by the knitted support. It may be noted that the knitted support, or braided support if desired, may be made with loops or openings 370 that are sized to receive a hypodermic needle of the desired diameter. For hypodermic needles commonly used for dialysis procedures, for example, needle sizes, and hence the size of openings between fibers of the tubular support, may be in the range of about 1.8 and 2.1 mm.

As structures have become increasingly complex, not only in design but also in the range of material use, pure analytical methods have begun to fail in describing the behavior of such structures. Due to the scientific challenge of closely matching a vascular graft of the type described herein to a host, analytical methods are rendered somewhat obsolete. Development of a prosthetic vascular graft which mimics the mechanical requirements and dynamic compliance of a normal healthy artery is made possible, however, with certain old tools, particularly cut and try methods in which incremental changes are made to the material or structure of the tubular support to modify its compliance properties, and the resulting properties are used to guide further changes. Empirical data or constitutive equations and mathematical analyses may be used for certain features. Alternatively, the use of numerical modeling with such tools as, for example, Finite Element Models and Methods, relying on continuum mechanics, along with certain other tools makes this level of customization feasible.

Results of pre-clinical studies with various designs and sizes of a stent for a baboon vein, as discussed in further detail below, have shown that the inner diameter of the stent relative to the outer diameter of the vein is a factor for the adequate performance of the stent and graft. Hereinafter, diameter of the stent refers to the inner diameter of the stent, and the diameter of the vein refers to the outer diameter of the vein.

The results have shown that under-sizing of the stent (i.e. the stent inner diameter is smaller than the vein outer diameter) provides maximum benefit of the stent for the graft performance, whereas over-sizing of the stent (i.e. the stent inner diameter is larger than the vein outer diameter) provides a graft performance and biological response that is relatively poor, and possibly even worse, than in non-stented vein grafts.

Taking this into account, as well as the fact that the outer diameter of a saphenous vein varies along the length of the vein, it has been found that the inner diameter of the stent: 1) should match the smallest outer diameter of a particular vein at any location along the harvested length, and 2) may be smaller, but should not be larger, than the smallest vein outer diameter. In addition, segments of a saphenous vein with an outer diameter larger than the minimum diameter of that vein may be "downsized" by the stent chosen according to method discussed herein. The terms "downsized" and "downsizing" as used herein refer to situations in which the stent is used to change the outer diameter of the vein to a smaller diameter. It has also been found that downsizing is desirable up to a certain, maximum allowed, degree, i.e., percentage of the maximum vein outer diameter.

The stent inner diameter to match a particular saphenous vein should be selected according to the minimum and maximum of the vein along the harvested length. Additional criteria may also be used to select a stent of an appropriate size for the selected vein.

The maximum degree of downsizing of veins by stents according to embodiments of the present invention during certain pre-clinical studies was approximately 40%. The degree, or percentage, of downsizing may be expressed as being equal to (outer diameter vein−inner diameter stent)/(outer diameter vein)*100.

Based on the analysis of the outer diameter of 50 human saphenous veins and allowing a maximum degree of downsizing of 40%, the following scenario may be one example for the selection of a particular stent inner diameter to match a particular human saphenous vein. For example, given four preselected stent sizes of 3.0 mm, 3.4 mm, 3.8 mm, and 4.2 mm, the following selection process may be used to match a particular human saphenous vein.

A first selection criteria may be set for a minimum outer vein diameter not being smaller than the stent inner diameter. Therefore, the 3.0 mm stent should be used for veins with a minimum outer diameter of between 3.0 mm and 3.3 mm; the 3.4 mm stent should be used for veins with a minimum outer diameter of between 3.4 mm and 3.7 mm; the 3.8 mm stent should be used for veins with a minimum outer diameter of between 3.8 mm and 4.1 mm; and the 4.2 mm stent should be used for veins with a minimum outer diameter of 4.2 mm and larger.

A second selection criteria may be set for a maximum degree of downsizing not to exceed 40%, which causes the maximum outer vein diameter for a particular stent inner diameter to be limited by the stent inner diameter that causes the maximum degree of downsizing of 40%. In view of the second criteria, the 3.0 mm stent should be used for veins with a maximum outer diameter of 5.0 mm and smaller; the 3.4 mm stent should be used for veins with a maximum outer diameter of 5.7 mm and smaller; the 3.8 mm stent should be used for veins with a maximum outer diameter of 6.3 mm and smaller; and the 4.2 mm stent should be used for veins with a maximum outer diameter of 7.0 mm and smaller.

Combining the first and second selection criteria results in the following categorization listed in Table IV:

TABLE IV

Stent Size Selection Criteria

| Stent ID [mm] | Min Vein OD [mm] | Max Vein OD [mm] |
| --- | --- | --- |
| 3.0 | 3.1-3.3 | 5.0 and smaller |
| 3.4 | 3.4-3.7 | 5.7 and smaller |
| 3.8 | 3.8-4.1 | 6.3 and smaller |
| 4.2 | 4.2 and larger | 7.0 and smaller |

There may be veins which do not fall in any of the size categories for various reasons. For example, the minimum outer vein diameter may be smaller than 3.0 mm, or the difference between minimum and maximum outer vein diameter may exceed the diameter range for a particular stent size, e.g. a vein with minimum outer diameter of 3.2 mm and maximum outer vein diameter of 5.9 mm. For these veins, it should be determined whether the following conditions are present: 1) either the minimum or the maximum outer diameter is limited to a very short segment of the vein, and the minimum or maximum diameter differs considerably from the outer diameter of the adjacent vein segments, or 2) the location of such a local decrease or increase of the outer vein diameter along the harvested vein segment allows this short segment to be removed while the resulting two vein segments can be used for the graft construction. If these conditions apply, the segment with the minimum or maximum outer vein diameter should be removed. The stent inner diameter would then be selected for each of the two resulting vein segments according to the above sizing criteria (see Table IV).

For veins having a minimum outer diameter smaller than 3.0 mm, and which do not allow the removal of the segment with this minimum diameter, a low degree of over-sizing may be permitted to allow the use of the 3.0 mm stent. The degree, or percentage, of over-sizing may be expressed as being equal to (outer diameter vein−inner diameter stent)/(outer diameter vein)*100, which results in a negative number. For example, if the minimum outer diameter of the vein is 2.8 mm, the degree of over-sizing of the 3.0 mm stent would be limited to (negative) 7.1%.

Another study was completed to assess the dimensional variability of human saphenous veins and to use the data for the mathematical optimization of practical aspects to guide the clinical implementation of external stenting and diameter "smoothing" or "smoothening". "Smoothing" or "smoothening" as used herein refers to altering the outer diameter of a section of the vein that is different (i.e., either larger or smaller) than an adjacent section with a stent so that the outer diameter of the vein is substantially the same along its length.

In this study, in 100 consecutive patients undergoing aorto-coronary bypass grafting, the outer diameter (OD) of 118 saphenous veins was recorded in 2 cm incremental segments during post-harvest in situ leakage-test distention using a Vernier caliper. Patient demographics (sex, race, age) and risk factors (weight, nutritional state, hypertension, diabetes and smoking) were also recorded.

The data collected was analyzed for hypothetical vessel smoothening. As a first step, the data was mathematically categorized. More specifically, for each vein, the minimum and maximum values of the outer diameter ($OD_{min}$ and $OD_{max}$, respectively) were identified in the data set that was recorded along the entire length of the vein. Using a stent to downsize the vein, the degree of downsizing ($DS_{Sm}$) required for complete smoothening of the outer diameter of the vein was determined for each individual vein using $$DS_{Sm} = \left(\frac{OD_{max} - OD_{min}}{OD_{max}}\right) \cdot 100. \quad (5)$$

From results of pre-clinical research, the limits for over-sizing ($p_o$) and under-sizing ($p_u$) of the stent relative to the vein to obtain diameter smoothening were chosen to be $p_o$=100% (no over-sizing) and $p_u$=50% of the outer diameter of the vein. With these parameters, the admissible range for the stent diameter for each individual vein ($\Delta_i$) can mathematically be expressed as $$\Delta_i = \left[\max_j \frac{p_u}{100} OD_i(x_j), \min_j \frac{p_o}{100} OD_i(x_j)\right] = [OD_i^-, OD_i^+] \quad (6a)$$

or $$\Delta_i = \left[\max_j 0.5\, OD_i(x_j),\right.$$
$$\left.\min_j OD_i(x_j)\right] = [0.5\, OD_{max,i}, OD_{min,i}] = [OD_i^-, OD_i^+]. \quad (6b)$$

The upper bound for the stent diameter ($OD_i^+$) and lower bound for the stent diameter ($OD_i^-$) for each individual vein was obtained using $$OD_i^+ = OD_{min,i} \quad (7)$$

and $$OD_i^- = 0.5\, OD_{max,i}, \quad (8)$$

Veins which did not satisfy the solution condition of $$OD_i^- \leq OD_i^+, \quad (8)$$

because the minimum diameter of the vein was smaller than one-half of the maximum diameter of the vein, were excluded from the data set and further analysis.

The individual stent diameter solution ranges $\Delta_i$=[$OD_i^-$, $OD_i^+$] with i=1, 2, . . . , 118, representing each of the 118 veins, were ranked according to the individual upper and lower bound. In the case that maximum lower bound $$\left(\max_i\, OD_i^-\right)$$

and the minimum upper bound $$\left(\min_i\, OD_i^+\right)$$

of the individual stent diameter ranges satisfied condition (10)

$$\max_i OD_i^- \leq \min_i OD_i^+, \quad (10)$$

the admissible range for the stent diameter accommodating the entire set of veins (D) was readily available as $$D \in \left[\max_i OD_i^-, \min_i OD_i^+\right]. \quad (11)$$

In the case that the condition (10) was not satisfied for the entire data set $\Delta_i$ with i=1, 2, . . . , 118, the data set was divided in n subsets, i.e., $\Delta_{i1,i2,\ldots,in}$ with $i_1$=1, 2, . . . , m, $i_2$=m+1, m+2, . . . , m+k and $i_n$=m+k+1, . . . , 118 such that condition (10) was satisfied for each subset. The admissible range of the stent diameter for each subset ($D_k$) was derived from the maximum lower bound and minimum upper bound of the stent diameter of each subset:

$$D_k \in \left[\max_i\, OD_i^-, \min_i OD_i^+\right]_k \quad (12)$$

$$k = 1, 2, \ldots, n$$

It was desired to accommodate the entire set of veins with a minimum number of different stent diameters (for commercial purposes), and choose the least amount of downsizing for an individual vein. In order to optimize for the number of different stent diameter ranges, represented by $D_k$, and the required downsizing of an individual vein, or average downsizing for a subset of veins, overlap of the stent diameter range between two vein subsets was allowed.

Figure 44:
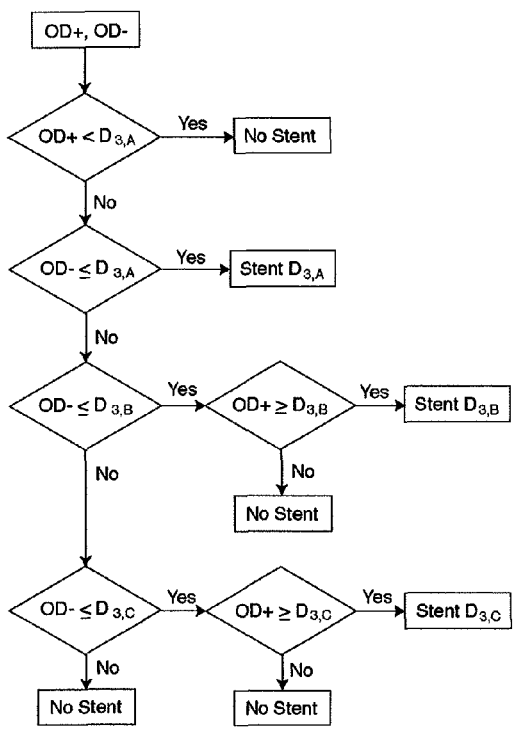
FIG. 44 is a flow chart of a method to select a stent for smoothening a human saphenous vein.
Figure 45:
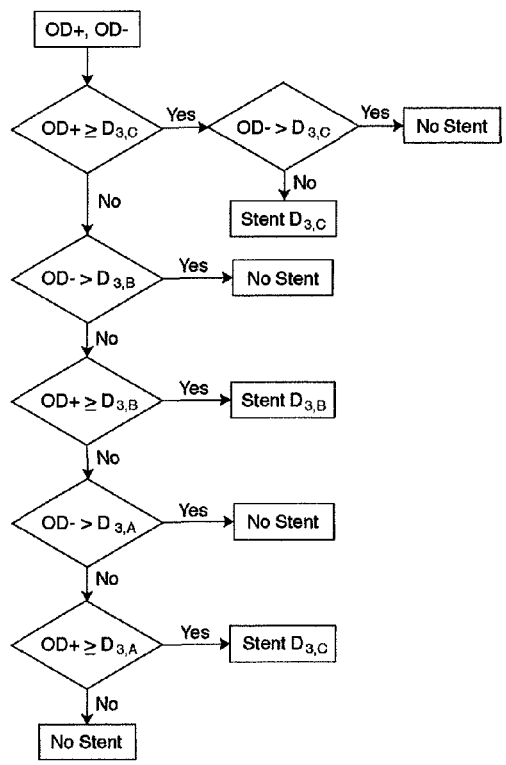
FIG. 45 is a flow chart of another method to select a stent for smoothening a human saphenous vein.

With the aim of a minimized number of stent diameters to accommodate the entire group of veins, two solution approaches were investigated. The first solution approach included three stent diameters ($D_{3,A}$, $D_{3,B}$, and $D_{3,C}$) and the second solution approach included two stent diameters ($D_{2,A}$ and $D_{2,B}$). For both solution approaches, the assignment of individual veins to one of the stent diameters was performed with two alternative algorithms, such that a particular vein received either the smallest stent diameter for the respective admissible stent diameter range of the vein, which resulted in a larger degree of downsizing, or the largest stent diameter possible for the respective admissible stent diameter range of the vein, which resulted in a smaller degree of downsizing. The two different classification algorithms employed for the assignment of veins to one stent diameter are illustrated in FIGS. 44 and 45 for the first solution approach featuring three stent diameters ($D_{3,A}$, $D_{3,B}$, and $D_{3,C}$), with $D_{3,A}<D_{3,B}<D_{3,C}$. Algorithm 1 (illustrated in FIG. 44) assigns the smallest possible stent diameter to the vein, while algorithm 2 (illustrated in FIG. 45) assigns the largest possible stent diameter to the vein. For example, a vein with a lower bound of the admissible stent diameter of $OD^- \leq D_{3,A}$ and the upper bound of the admissible stent diameter of $OD^+ \geq D_{3,B}$ would be assigned to the smaller stent diameter ($D_{3,A}$) with algorithm 1, and to the larger stent diameter ($D_{3,A}$) with algorithm 2.

For both solution approaches and classification algorithms, the distribution of veins among the proposed stent sizes was evaluated with respect to the number of veins and the average degree of downsizing in each stent size group, as well as the grand mean degree of downsizing obtained in the entire group of veins. The downsizing of veins through stenting was also compared to the smoothing downsize degree, which expresses the minimum amount of downsizing to achieve complete smoothening of the vein diameter. Smoothening of a vein (i.e. altering the outside diameter of the vein to a substantially constant diameter) is ensured in the case where the stenting downsize degree is equal to or larger than the smoothening downsize degree. Depending on the formulation of the sizing condition, e.g., oversizing of the stent not being permitted as proposed, the stenting downsize degree will always satisfy this criteria for a stent assigned by employing the proposed approach. In the case that oversizing of the stent is permitted, the smoothening of the vein through application of a stent would need to be assessed in further detail.

The average length of the 118 harvested veins was 28.4±9.5 cm with a minimum and maximum length of 10 cm and 52 cm, respectively. The minimum and maximum outer diameter over all 118 veins was 2.1 mm and 6.5 mm with an average minimum outer diameter of 3.50±0.61 mm and average maximum outer diameter of 4.77±0.75 mm.

For the 118 harvested veins, the average downsizing required for complete smoothening of the vein diameter according to equation (5) above was 26.0±11.1%, with a minimum of 0% and a maximum of 57.2%. The distribution of veins in incremental classes according to the smoothening downsize degree ($DS_{Sm}$), i.e., $0\% \leq DS_{Sm} < 10\%$, $10\% \leq DS_{Sm} < 20\%$, etc., and the proportion of the total number of veins is summarized in Table V below.

TABLE V

Distribution of Harvested Veins According to Classified Smoothening Downsize Degree ($DS_{Sm}$)

| Downsizing [%] | No of veins | Proportion [%] |
|---|---|---|
| $0 \leq DS_{Sm} < 10$ | 6 | 5.1 |
| $10 \leq DS_{Sm} < 20$ | 30 | 25.4 |
| $20 \leq DS_{Sm} < 30$ | 45 | 38.1 |
| $30 \leq DS_{Sm} < 40$ | 19 | 16.1 |
| $40 \leq DS_{Sm} < 50$ | 17 | 14.4 |
| $DS_{Sm} \geq 50$ | 1 | 0.8 |

The largest proportion of veins, 38.1%, needed moderate downsizing between 20% and 30% to achieve diameter smoothening, whereas only one vein exceeded a downsize requirement of 50%. The number of veins appears to be distributed normally among the downsizing classes, with a slight skew towards the lower downsizing degrees. With the proposed limits of oversizing and downsizing of a vein, i.e., no oversizing and maximum 50% downsizing, and the related upper and lower bounds of the stent diameter formulated in equations (7) and (8) above, 117 of the 118 veins, or 99.2%, satisfied the condition formulated in equation (9) above of $OD_i^- \leq OD_i^+$. More specifically, for 115 veins, the lower bound of the individual admissible stent diameter range was less than the upper bound of the individual admissible stent diameter range ($OD_i^- < OD_i^+$), and for 2 veins, there was a single value for the individual admissible stent diameter, as $OD_i^- = OD_i^+$.

Figure 46:
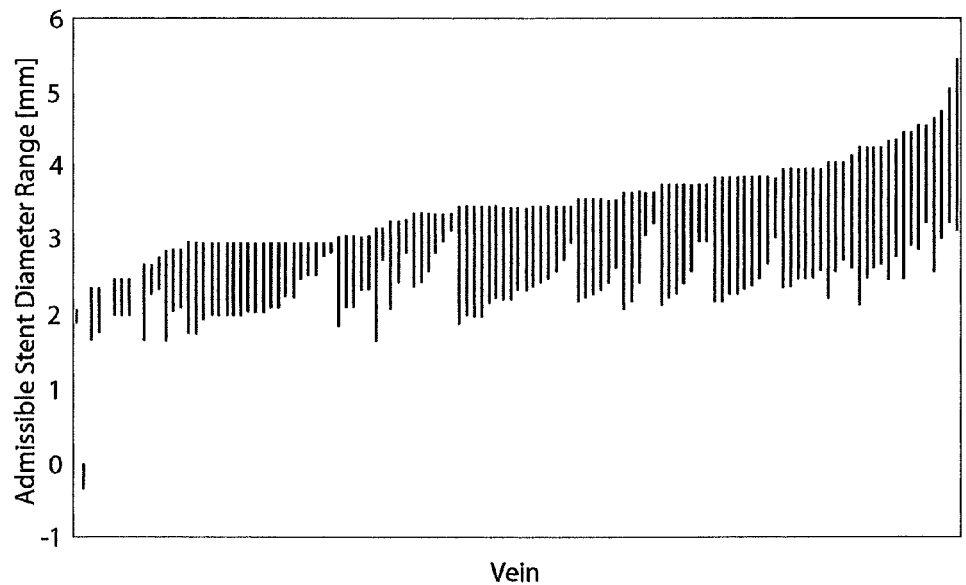
FIG. 46 is a graph showing individual admissible stent diameter ranges for a set of veins from an experimental study.

For one vein, the lower stent diameter bound exceeded the upper bound. This vein did not satisfy equation (9) above, and was excluded from the further analysis. This vein required more than 50%, specifically 57.2%, downsizing for diameter smoothening, which was outside of the initial permissible percentage of undersizing the stent ($p_u$). The individual admissible stent diameter ranges ($\Delta_i$) for the entire set of 118 veins based on the conditions of no oversizing and downsizing up to maximum of 50% are illustrated in FIG. 46. The negative stent diameter range shown in FIG. 46 indicates the one vein that did not qualify, due to the lower stent diameter bound ($OD_i^-$) exceeding the upper stent diameter bound ($OD_i^+$), and was disregarded from further analysis. In FIG. 46, the stent diameter ranges are ranked according to the upper stent diameter bound (primary ranking parameter) and the lower stent diameter bound (secondary ranking parameter).

The lower bound for the stent diameter ($OD_i^-$) ranged between 1.65 mm and 3.25 mm with a mean of 2.39±0.38 mm. The upper bound for the stent diameter ($OD_i^+$) ranged between 2.10 mm and 5.50 mm with a mean value of 3.50±0.61 mm.

With a maximum value of the lower bound of the stent diameter (max $OD_i^-$) of 3.25 mm and the minimum upper bound of the stent diameter $$\left( \min_i OD_i^+ \right)$$

of 2.10 mm, the condition for solution of the admissible stent diameter range, i.e.

$$\max_i OD_i^- \leq \min_i OD_i^+,$$

was not satisfied. Consequently, a single stent diameter, or stent diameter range, accommodating all 117 veins could not be identified with the proposed downsizing and oversizing conditions.

To accommodate the individual stent diameter ranges presented in FIG. 46, stent diameters of $D_{3,A}=3.0$ mm, $D_{3,B}=3.5$ mm and $D_{3,C}=4.0$ mm were proposed for the 3-stent-solution, whereas diameters of $D_{2,A}=2.9$ mm and $D_{2,B}=3.3$ mm were proposed for the 2-stent-solution. For either solution approach, the classification of individual veins according to the stent diameters suggested was performed in two alternative fashions seeking for the smallest stent size and largest stent size for each vein. As discussed above, the underlying classification algorithms are illustrated in FIGS. 44 and 45 for the 3-stent solution approach.

The solution approach featuring three stent diameters $D_{3,A}=3.0$ mm, $D_{3,B}=3.5$ mm and $D_{3,C}=4.0$ mm resulted in 14 veins not being accommodated in any of the three stent sizes, independent of the classification algorithm used. Thirteen veins exhibited an upper stent diameter bound of less then 3.0 mm, and therefore required a stent diameter smaller than 3.0 mm to satisfy the proposed downsizing and oversizing conditions. One vein had a stent diameter range between 3.15 mm and 3.4 mm, so none of the pre-selected stent diameters could accommodate that vein. The classification of the remaining 102 veins with algorithm 1 (minimizing the stent diameter and maximizing the downsize degree) assigned 95 veins to the stent diameter of 3.0 mm, 7 veins to the stent diameter of 3.5 mm, and no vein was assigned to the 4.0 mm stent diameter. The classification of the 102 veins with algorithm 2 (maximizing the stent diameter and minimizing the downsize degree) resulted in the following distribution of the veins: 35 veins for 3.0 mm stent diameter, 43 veins for 3.5 mm stent, and 24 veins for 4.0 mm stent diameter. The vein classification and resulting downsizing in the different diameter groups of the 3-stent-diameter approach is summarized in Table VI below.

TABLE VI

Distribution of veins and resulting downsizing for 3-stent-diameter solution approach

| Classification Option | Parameter | Excluded veins | Stent Diameter [mm] | | | |
|---|---|---|---|---|---|---|
| | | | 3.0 | 3.5 | 4.0 | All |
| Minimum Stent Diameter Maximum Downsizing (Algorithm 1) | N | 15 | 95 | 7 | 0 | 102 |
| | Mean $DS_{St}$ [%] | — | 35.8 ± 8.6 | 44.5 ± 1.6 | — | 36.4 ± 8.6 |
| | Min $DS_{St}$ [%] | — | 9.1 | 42.6 | — | 9.1 |
| | Max $DS_{St}$ [%] | — | 50.0 | 46.2 | — | 50.0 |
| | Mean $DS_{Sm}$ [%] | — | 24.0 ± 9.8 | 29.2 ± 11.2 | — | 24.3 ± 10.0 |
| | $DS_{St}/DS_{Sm}$ | — | 1.68 ± 0.71 | 1.79 ± 0.87 | — | 1.69 ± 0.72 |
| Maximum Stent Diameter Minimum Downsizing (Algorithm 2) | N | 15 | 35 | 43 | 24 | 102 |
| | Mean $DS_{St}$ [%] | — | 32.3 ± 10.4 | 26.7 ± 9.0 | 24.2 ± 8.1 | 28.1 ± 9.8 |
| | Min $DS_{St}$ [%] | — | 9.1 | 7.9 | 7.0 | 7.0 |
| | Max $DS_{St}$ [%] | — | 50.0 | 46.2 | 38.5 | 50.0 |
| | Mean $DS_{Sm}$ [%] | — | 30.1 ± 9.8 | 23.3 ± 9.2 | 17.8 ± 6.4 | 24.3 ± 10.0 |
| | $DS_{St}/DS_{Sm}$ | — | 1.12 ± 0.34 | 1.19 ± 0.23 | 1.41 ± 0.48 | 1.22 ± 0.35 |

$DS_{St}$ = stenting downsizing degree
$DS_{Sm}$ = smoothing downsize degree

The smoothening downsize degree ($DS_{Sm}$) refers to the downsizing required to completely smoothen a vein, i.e., alter the maximum vein OD to the minimum vein OD. The stenting downsizing degree ($DS_{St}$) refers to the downsizing a vein experiences, i.e., amount the OD of a vein changes, by having a stent on the outside of the vein.

The classification towards least stenting downsizing degree resulted in a more even distribution of the veins among the three stent diameters proposed, whereas for maximum downsizing, the majority of veins (91.1%) were assigned to the smallest stent diameter, while the largest stent diameter was left unpopulated.

The classification of the 117 veins employing the two-stent solution approach with stent diameters of $D_{2,A}$=2.9 mm and $D_{2,B}$=3.3 mm excluded 11 veins due to a upper stent diameter bound of less then 2.9 mm, again independently of the algorithm used. From the remaining 106 veins, 93 and 13 veins were assigned to the 2.9 mm and 3.3 mm stent, respectively, when the minimum stent diameter associated with the maximum downsize degree was targeted for each vein (classification algorithm 1) Aiming at the least stenting downsizing degree by assigning the largest possible stent to each vein, the 2.9 mm stent was assigned to 30 veins and the 3.3 mm stent to 76 veins. The mean stenting downsize degree for the two options of maximum and minimum downsizing was 36.7±8.2% and 31.2±9.7%, respectively, for the 2.9 mm stent and 46.6±1.8% and 33.7±8.4%, respectively, for the 3.3 mm stent. The entire data set is summarized in Table VII below.

TABLE VII

Distribution of veins and resulting downsizing for 2-stent-diameter solution approach.

| Classification Option | Parameter | Excluded Veins | Stent Diameter [mm] | | |
|---|---|---|---|---|---|
| | | | 2.9 | 3.3 | All |
| Minimum Stent Diameter Maximum Downsizing (Algorithm 1) | N | 11 | 93 | 13 | 106 |
| | Mean $DS_{St}$ [%] | — | 36.7 ± 8.2 | 46.6 ± 1.8 | 38.0 ± 8.4 |
| | Min $DS_{St}$ [%] | — | 12.1 | 44.1 | 12.1 |
| | Max $DS_{St}$ [%] | — | 36.7 ± 8.2 | 46.6 ± 1.8 | 38.0 ± 8.4 |
| | Mean $DS_{Sm}$ [%] | — | 23.3 ± 9.5 | 33.3 ± 10.5 | 24.5 ± 10.1 |
| | $DS_{St}/DS_{Sm}$ | — | 1.79 ± 0.78 | 1.61 ± 0.77 | 1.77 ± 0.78 |
| Maximum Stent Diameter Minimum Downsizing (Algorithm 2) | N | 11 | 30 | 76 | 106 |
| | Mean $DS_{St}$ [%] | — | 31.2 ± 9.7 | 33.7 ± 8.4 | 33.0 ± 8.8 |
| | Min $DS_{St}$ [%] | — | 12.1 | 13.2 | 12.1 |
| | Max $DS_{St}$ [%] | — | 49.1 | 49.2 | 49.2 |
| | Mean $DS_{Sm}$ [%] | — | 28.4 ± 10.2 | 23.0 ± 9.7 | 24.5 ± 10.1 |
| | $DS_{St}/DS_{Sm}$ | — | 1.12 ± 0.34 | 1.19 ± 0.23 | 1.41 ± 0.48 |

$DS_{St}$ = stenting downsizing degree
$DS_{Sm}$ = smoothing downsize degree

To further assess and rank the various proposed solution approaches (3 stent versus 2 stent diameters, and maximum downsizing versus minimum downsizing), the downsizing of the veins through the assigned stent diameter was compared to the smoothening downsize degree. The ratio of stenting downsize degree to smoothening downsize degree, $DS_{St}/DS_{Sm}$, was required to be equal or larger than 1 to achieve complete diameter smoothening. Considering the grand mean of the ratio $DS_{St}/DS_{Sm}$ for all veins which received a stent, the smallest degree of downsizing was obtained with the 3-stent solution approach in combination with the classification algorithm 2 opting for least downsizing ($DS_{St}/DS_{Sm}$=1.22±0.35), followed by the 2-stent approach with the same classification algorithm ($DS_{St}/DS_{Sm}$=1.41±0.48), and the 3-stent and 2-stent approach with the alternative classification algorithm ($DS_{St}/DS_{Sm}$=1.69±0.72 and 1.77±0.78, respectively).

For the condition that oversizing of the stent is not permitted, the solution approaches proposed ensured that the upper bound of the admissible stent diameter for each vein did not become smaller than minimum vein diameter for any one vein, and hence resulted in complete smoothening. This was confirmed for both solution approaches and classification algorithms in that the minimum of the ratio of stenting downsize degree to smoothening downsize degree, $DS_{St}/DS_{Sm}$, was equal to 1. The values of the $DS_{St}/DS_{Sm}$ ratio for different stent diameter groups, along with the group mean values of the smoothening downsize degree, are given in Table VI for the 3-stent solution and Table VII for the 2-stent solution. The 3-stent solution with least downsize classification resulted in the closest match between stenting downsize degree and smoothening downsize degree for each stent diameter whereas the 2-stent solution 1 with maximum downsize classification returned the largest differences between stenting downsize degree and smoothening downsize degree (following the same order than for the grand means of the $DS_{St}/DS_{Sm}$ ratio).

Figure 47:
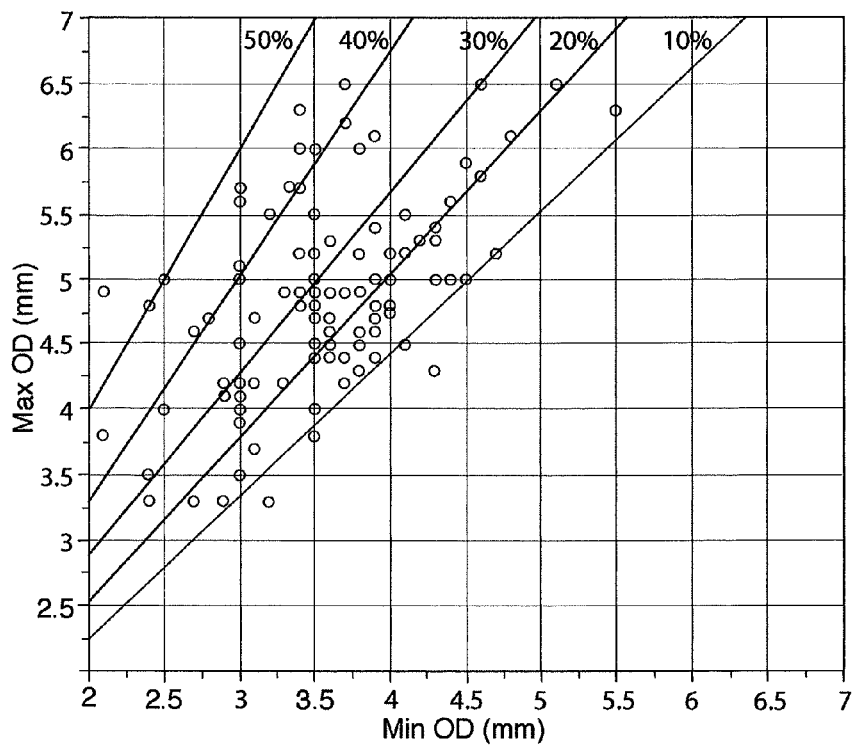
FIG. 47 is a graph showing maximum to minimum outer diameter relationships of saphenous veins distended during leak testing during clinical vein harvest for coronary artery bypass surgery.
Figure 48:
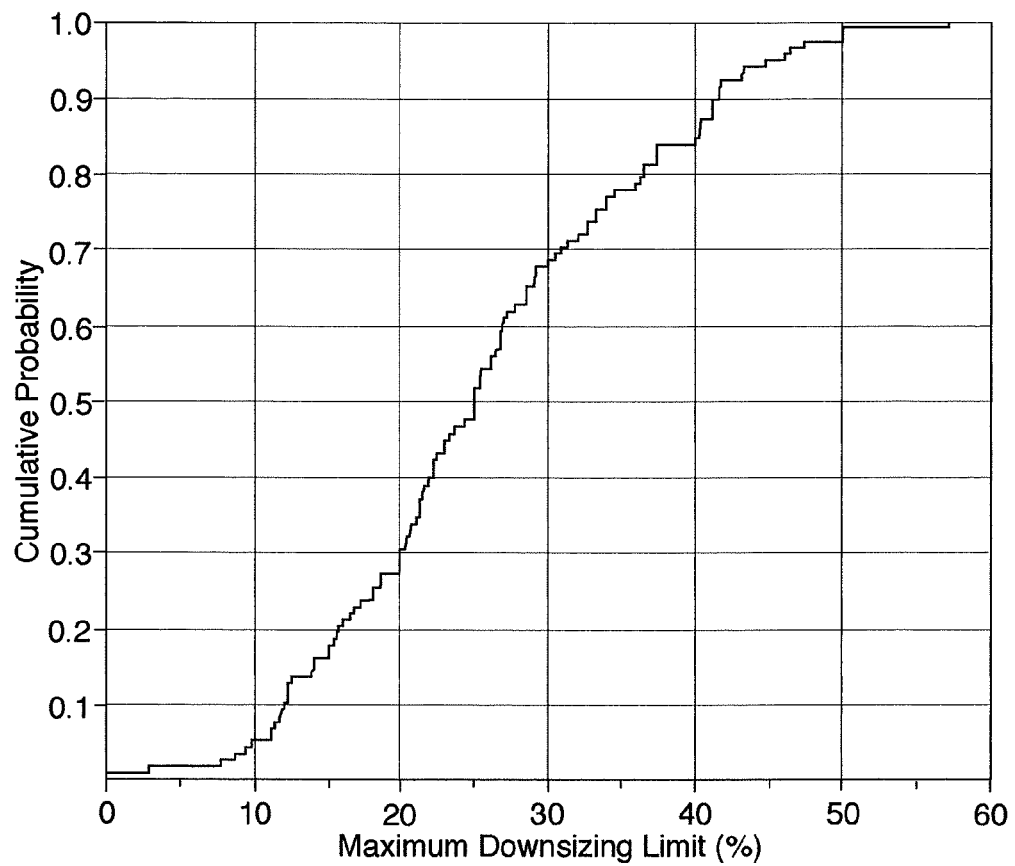
FIG. 48 is hypothetical cumulative distribution plot showing increasing probability of successful results from the theoretical study.

Hypothetical application of external stents equivalent in size to the corresponding minimum outer diameter of each vein resulted in a mean maximum downsizing of 26.0±1.0% (range 0 to 57.1%). Whereas this solution is an unpractical one, since 86 differently sized stents would be required to accommodate the 118 veins accepting a tolerance of 0.1 mm, the fact that 117 veins were maximally downsized by 50% or less suggests a phenomenon intrinsic to the lengths of human saphenous vein harvested, namely that the maximum outer diameter rarely exceeds the minimum outer diameter by more than 50%. FIG. 47 shows the relationship between the $OD_{min}$ and $OD_{max}$ for each vein. Also shown in FIG. 47 are lines representing an amount of downsizing ranging from 10% to 50%. By increasing the amount of downsizing, an increased number of veins may be accommodated, thereby confirming again the intrinsic constraint of the relationship between these two parameters. The relationship between the maximum downsizing limit and the proportion of veins thereby accommodated is shown in FIG. 48. The falloff of veins is dramatic with an increased setting of the downsizing limit, and indicates that a downsizing limit of not less than 50% should be used. Therefore, without limiting the number of available stent sizes and by calculating the proportion of veins with an upper tolerance interval not exceeding 50%, simply applying a stent with a fully distended inner diameter equal to the $OD_{min}$ of the vein, both the 'zero-oversizing' and '50% maximum downsizing' rules were seen to be met in 99% of veins with 95% confidence.

Hypothetical application of an external stent with an internal diameter equivalent to the overall minimum outer diameter observed in all veins, namely 2.1 mm, may avoid the requirement for an excessive number of stent solutions and also any upsizing which would occur at a point where the vessel outer diameter would be smaller than the inner diameter of the applied stent. However, excessive downsizing may result, which may not be desirable.

In order to optimize the number and sizing of stents, the technique of recursive partitioning was applied to the vein data. This method deployed by JMP, a statistical software package (version 6.0.3, Cary, N.C.), recursively partitions, in this case veins, based on a hypothetical relationship between the minimum OD and maximum OD/minimum OD ratio for each vein, thereby creating a tree of optimal OD minima cut-points for prediction of maxima/minima ratios within the cohort of veins being studied. It does this by an iterative process where all possible cut-points (and thus groupings) are examined. The process is manually advanced until a desired fit (e.g. a plateau in the R2 values) is seen to be reached with the minimum number of partitions. The result of these partitions suggested stent sizes of 3.5 mm, 2.7 mm, 3.9 mm and 3.3 mm in that order. Hypothetical application of these stent sizes to simulate single, double, triple and quadruple solutions revealed acceptable downsizing (<50%) but with a moderate degree of oversizing in the case of the deployment of a single 3.5 mm stent. However, distribution of both the 3.5 mm and 2.7 mm stents based on the $OD_{min}$ for each vein confirmed success in 100% of veins with no oversizing and not more than 50% downsizing. The addition of the third 3.9 mm and fourth 3.3 mm stents into the solution did not appear to affect the extent of downsizing at all despite a fairly even distribution of the cohort of veins across the four stent sizes.

Of course, the above identified stent sizes are provided as examples only. For example, an alternative selection of stent sizes may include diameters of 3.6 mm, 2.8 mm, 4.0 mm, and 3.4 mm, etc. The above-identified stent sizes are not intended to be limiting in any way.

For ease of use by surgeons, the selection criteria for stent size may be utilized in a selection tool such as a "dial disc" or a look-up table where, in the simplest case, the surgeon has to select the minimum and maximum vein outer diameters on two independent scales and the "dial disc" returns the appropriate stent size, or a recommendation for an adjustment procedure should the vein diameters do not fall within one stent size group.

In a more sophisticated version of the "dial disc", the surgeon would be required to enter or select the minimum and maximum vein diameters and one or two additional selection criteria, such as desired maximum downsizing, in order to obtain a recommendation for the suitable stent size.

It is also contemplated that such a selection tool may be in the form of a computer program in which the surgeon enters the minimum and maximum vein diameters, and, optionally, the desired maximum downsizing, and the program calculates and displays the most suitable stent size based on the values inputted.

For example, the surgeon (or his/her designee) may enter the required data into a computer (e.g. a PC, PDA, etc.) via a user input (e.g., a keyboard or mouse selecting entries on a graphical user interface). The software program resides on a computer readable medium (e.g., a hard drive, RAM, or an insertable/removable memory like a CD, DVD, or floppy disk). The software program comprises computer executable code for performing the calculating method (which may be in accordance with any embodiment described herein or any variant thereof), and displays the results to the surgeon and/or his designee. The program may reside on a local computer at which the surgeon or his/her designee works. Likewise, the software program may be network based, such that the program executes at a remote location, with the inputs and results being transmitted to and from the local computer at which the surgeon or his/her designee works. The display may be accomplished via a graphical user interface (e.g., a display screen), or by printing out the results. Thus, the scope of the invention includes the software program comprising computer executable instructions for performing such methods.

OVERVIEW OF EXAMPLES

For the repair of diseased vessels using autologous tissue, the saphenous vein graft is the surgeon's main option following the use of arterial tissue e.g., internal mammary artery (IMA) and radial artery. Unfortunately, performance of saphenous vein grafts is substantially less than arterial tissue, given the thin-walled vein architecture and tendency to undergo excessive remodeling following exposure to arterial pressure. This excessive remodeling is thought to be mainly due to tissue damage and ensuing unchecked cellular responses as the venous tissue experiences dimensions, pressures, and pulses not seen in its native venous environment. Ultimately, such a response can lead to graft stenosis and occlusion.

It has been shown that an external stent placed over the saphenous vein at implantation prevents excessive vein dilatation upon exposure to arterial blood flow. A markedly reduced remodeling response has also been seen in these externally stented veins. In the previous studies, the external saphenous vein stents had minimal or no natural radial compliance incorporated into the stent design. It was hypothesized that a saphenous vein surrounded by a stent engineered to have more natural radial compliance i.e., one close to that of native arterial tissue, will undergo an even more favorable remodeling response. The latter will be reflected by histological evidence of a more arterial-like architecture following exposure the arterial environment. Ultimately, the goal was for this favorable remodeling to translate to an improved saphenous vein graft patency compared to non-externally-stented controls.

As shown in the Examples below, external mechanical reinforcement of vein grafts with size-matching stents prevented intimal hyperplastic response and maintained the lumenal dimension of the grafts ensuring consistent flow condition in the grafts over time and compared to the host arteries. Example 1 shows that using a non-compliant braided wire stents to support grafted femoral vein segments results in 100% patency at 6 weeks and 75% patency at 12 weeks, while unsupported femoral vein grafts had 100% patency, but only 50% patents at 12 weeks.

As shown in the Examples below, downsizing of vein grafts with external stents having a smaller diameter than the grafted vein segment, considerably limited the intimal and adventitial hyperplastic response, and prevented endothelial damage, compared to vein grafts with oversized external stent support (see Example 2). Thus, downsizing of vein grafts with external stents was found to be superior to oversized external support, and as good as external mechanical support matching the size of the vein in venous circulation (see, Examples 1 and 2).

As shown in the Examples below, a saphenous vein graft supported by an external stent with natural radial compliance resulted in remodeling into a histological architecture consistent with arterial tissue. Braided and knitted stents with low or high radial compliance were used to show the effect of radial compliance on remodeling and graft patency, and were further used for comparing and contrasting the healing response of the stents produced by different manufacturing methods (See Example 4). With increasing time after implantation, braided stents showed an increase in lumen diameter, while knitted stents did not show an increase in lumen diameter, indicating that the knitted stents provided greater size stability for the vein graft over time. (See Example 4).

In previous studies, external saphenous vein stents were tested only in the peripheral vasculature. However, a main intended application is the coronary vasculature. As shown in the Examples below, a canine model confirmed the hypothesis that a canine femoral vein surrounded by a stent engineered to have a natural radial compliance (i.e., one close to that of native arterial tissue) will undergo a favorable remodeling response when implanted in the coronary vasculature, and more arterial-like architecture would be found in the vein grafts upon explantation (see Examples 3.A. and 3.B. In a baboon model, the feasibility of using a saphenous vein surrounded by knitted compliant stent for grafting in an aorto-coronary (CABG) position was demonstrated, where stented saphenous vein CABG grafts had a high patency rate, and showed a favorable remodeling response (see Example 5).

As noted above, the external saphenous vein stents in earlier studies had minimal or no radial compliance incorporated into the stent design. In later phases, two types of stent designs were studied along with a crimping feature intended to provide increased radial (circumferential) compliance (see Example 4).

Example 1

Effect of External Reinforcement of Vein Grafts on the Remodeling of the Veins Transposed into Arterial Circulation Briefly, a baboon bilateral femoral artery vein graft model was used in a two-factor study to assess the effects of stented and non-stented vein grafts, and implant duration (6 weeks and 12 weeks) in a total of eight (8) baboons.

Protocols

The non-compliant stented vein grafts used in this study were segments of superficial femoral vein stented with Nitinol (NiTi)-wire tubular braid stents with an OD of 5 mm, assumed to be non-compliant in a radial direction such that no change in diameter due to changing blood pressure would be permitted. The majority of stents used for implantations were 36 carrier (wire) Nitinol stents with 0.025 mm wire thickness, with an expected compliance of between about 1.6 to 2.3%/100 mmHg. One implantation for the 6 week implant duration included one pilot implantation with a stent having 72 carriers (wires) and 0.050 mm wire thickness.

Adult Chacma baboons (5 female, 3 male, "senescent Chacma Baboon model") were anesthetized and intubated. The femoral artery and vein were exposed through a longitudinal incision of approximately 15 cm. After administration of heparin (250 U/kg), the superficial femoral vein (SFV) was clamped distal to the origin of the deep femoral vein and as far distally as possible before disappearing in the adductor channel. In some baboons, prior to clamping, the in situ vein diameter was estimated by approximation using the jaws of a vernier caliper. The adjacent superficial femoral artery (SFA) was equally clamped after the origin of the deep femoral artery and distally at the same level as the SFV. After excision of a comparable segment of the SFA, the reversed SFV was anastomosed to the distal segment of the artery in an end-to-end fashion, using a continuous running suture of 7-0 Prolene. In the control group, the proximal end-to-end anastomosis was completed in a similar fashion. In the experimental group, a piece of Nitinol stent of the same length as the vein segment was cut off and the vein was gently pulled through the stent after the distal end-to-end anastomosis had been completed. The proximal end-to-end anastomosis was completed, similarly using a running suture of 7/0 Prolene. In the experimental group, the Nitinol stent was secured to the arterial adventitia on either end over the anastomosis, using a superficial single suture of 7/0 Prolene. After removal of the arterial clamps and restoration of the blood flow, outside diameters of the mid-section of the control vein grafts were measured using a vernier caliper.

Macrophotographs of the implanted graphs were taken and, after ensuring adequate haemostasis, the incisions were closed in two layers (2/0 Vicryl sutures for subcutaneous layer and 2/0 Nylon sutures for skin).

Explantation:

At 6 or 12 weeks after implantation, the vein grafts were evaluated for patency and explanted. After sedation, intubation, and general anaesthesia, the skin was incised on both sides from inguinal towards caudal direction according to the length of the implanted graft. The superficial femoral artery was prepared at both ends proximal and distal of the graft (±1.5 cm from the anastomosis) and ligatures were placed but not yet tied. Subsequently the animal was fully heparinized (250 IU/kg) and sacrificed by a bolus injection of a KCl (40 mmol) and cessation of spontaneous cardiac activity was verified on the ECG monitor before ventilation was stopped. The femoral arteries were cannulated proximally and distally to the graft within the above-mentioned ligatures. The prostheses were each rinsed in situ with 100 ml PBS and fixed with 100 ml 10% FA under pressure. Finally the grafts were excised en-bloc with approximately one centimeter of surrounding tissue. The proximal side was marked with a liga-clip before the explanted grafts were placed in a container filled with PBS/FA for further preparation.

Sample Processing:

The first macroscopic pictures of the explanted sample were taken after excess tissue was trimmed from the vein graft. Subsequently, the grafts were carefully opened longitudinally from each end towards the mid-graft region (in order to positively identify the middle of the graft). Once identified, and before the longitudinal incision was completed, an 8 mm section (denoted section 3) was removed as an intact graft ring. For the 6-week implant duration study, this sample was sub-sectioned into a 3 mm ring-section for later SEM analysis, and a 5 mm section for light microscopy. For the 12-week implant duration study, a 1 cm ring section was taken for light microscopy whereas later SEM analyses used the adjacent graft segments. Additional higher magnification images of the ring-section (section 3) were taken by conventional macrophotography and by using a stereo microscope, and images and data were captured on a Filemaker database.

For macroscopical image analysis, the ring-section was placed onto a ruler and straight vertical pictures were taken and imported into the Q-Win Image analysis Unit. The following parameters were calculated: cross sectional area; theoretical mean lumenal diameter (calculated from perimeter measurements; but due to the irregularity of the perimeter as a result of IH, this theoretically calculated diameter always represents an overestimation of the true mean diameter); and minimum/maximum lumenal diameter (directly measured; because of the overestimate obtained by calculating the mean diameter from the perimeter, it is possible that the measured maximum diameter is smaller than the calculated mean diameter.)

For light microscopy, vein grafts were fixed in 10% formalin (in PBS, pH 7.4) for 24 hours, then transferred into 70% ethanol before further processing as described below.

Embedded non-stented vein grafts ("controls") were prepared by processing through increasing concentrations of alcohol (70% to 100%), and cleared using 2,2,4 trimethyl-pentane (3 changes) and subsequently infiltrated and embedded in paraffin wax. Sectioning was done on a MICROM H360 heavy duty microtome (3 micron sections). Slides were stained for Haematoxylon and Eosin, Victoria Blue and immunocytochemically for CD 31 and Actin.

Embedded stented vein grafts were prepared as follows. Light microscopy was entirely done on the basis of resin embedding. For the 6-week implant duration study, half of the ring-sections for light microscopy were resin embedded whereas the other half underwent the manual removal of the stent wires under a stereo microscope by a fine-pointed forceps prior to being wax embedded like the (non-stented) controls. Samples for resin embedding were hand-processed through 100% alcohol at 4° C., infiltrated with 2 changes of Technovit 8100 infiltration solution on a sample roller (overnight 4° C.), and subsequently embedded in T8100 (under vacuum, 0° C., 3 hours) and sectioned on an Isomet Precision Saw 2000 (Buehler), resulting in thick (100 micron) sections. The sections were then ground down using a Metaserv 2000 grinder using 2 different grades of sand paper in order to obtain reasonably thin sections. These slides were then stained either Haematoxylin and Eosin ("HE") as well as a Masson's trichrome stain Resin was not removed and slides were mounted using an aqueous mounting medium. Wax sections were routinely stained HE, Azan, Movat and Victoria Blue.

Image Analysis

A Leitz DM RB microscope with an attached Leica DC200 digital camera was used to visualize and capture color micrographs of the vein grafts. Macropictures were directly imported to a computer equipped for image analysis. Image analysis was performed using Leica Q-Win 500 software. Briefly, after capturing images of Azan/Movat stained sections, 10-25 measuring fields of each sample capturing the entire specimen were used for the analysis, depending on the size of the particular vein graft. Interactive measurements were used to highlight the area of interest by detection-filtering of the color images (achieved by threshholding). The parameters measured were: lumenal cross sectional area and calculated mean lumenal diameter; lumenal minimum and maximum diameter; cross sectional area of intima (intimal hyperplasia, IH) tissue; thickness of IH tissue layer (minimum, maximum, mean); cross sectional area of medial tissue; thickness of media (minimum, maximum, mean); proportion of media tissue consisting of SMCs; cross sectional area of adventitial (advential hyperplasia, AH) tissue; thickness of AH tissue layer (minimum, maximum, mean)

The following histology sections were used: complete ring section of mid graft section of each graft; longitudinal sections of proximal and distal anastomotic region of each graft; sections stained with Movat stains, Azan stains, Victoria Blue stains, and HE stains.

Fields were counted as described below. Layers were defined according to the following criteria: (1) Intimal Hyperplasia (IH) Tissue: the combined use of both the presence of often clearly visible stretches of internal elastic membrane and the presence of light-blue ground substance within the IH tissue on modified Movat stains made it relatively easy to delineate manually the boundaries of the IH tissue. (2) Media: On the modified Movat stains, the smooth muscle cells appear dark brown, while collagen is red. A smooth line was manually drawn alongside the outside perimeter of the media to delineate it from the adventitia. (3) Adventitial Hyperplasia: This layer was easily delineated as the area between the line described above and the area where the stent had been (evidenced by the gaps in the tissue where the stent wires had been removed.)

Mid-graft sections: (1) The lumenal cross sectional area was measured from a 0.5× image taken from a mid-graft ring section with a macro lens. Manual calibration was used to accommodate the 0.5× objective in the image analysis program. (2) Intimal Hyperplasia and Media assessment were obtained from the image analysis of composite pictures taken from the entire circumference of the graft at 10× magnification (in average 10-25 fields—depending on the size of the graft). (3) Adventitial Hyperplasia was assessed from the image analysis of composite pictures taken from the entire circumference of the graft at 5× magnification.

Anastomotic sections: (1) Anastomotic Intimal Hyperplasia assessment was obtained from the image analysis of composite pictures taken from the entire length of the section at 1.6× magnification. (2) Media was assessed from the image analysis of composite pictures taken from the entire length of the section at 10× magnification. (3) Adventitial Hyperplasia was assessed from the image analysis of composite pictures taken from the entire length of the section at 5× magnification.

Statistical Analysis of Midgraft Data and Anastomotic Data:

The microscopical image analysis for midgraft sections was consistent for all grafts such that data was always related to full cross sections, i.e. the entire circumference of midgraft ring sections. Longitudinal anastomotic sections may, however, have varied in length available for analysis for different grafts. In order to ensure consistency in the analysis of the anastomotic sections, anastomotic data for a length of 4 mm from the anastomoses towards the midgraft region was included in the statistical analysis. Any data obtained from longitudinal sections beyond 4 mm distance from the anastomoses was discarded from the statistical analysis, however, has been retained in the study records.

All data of cross-sectional area (e.g. IH area, AU area, media area) are sums of individual measurements of microscopical composite images. All data of thicknesses (e.g. IH thickness, AH thickness, media thickness) and ratios (e.g. proportion of smooth muscle cells in media layer) are mean values of individual measurements of microscopical composite images. The microscopic image analysis includes the entire cross-sectional circumference of graft wall for annular midgraft sections but only 4 mm graft wall for longitudinal anastomotic sections. Hence cumulative data based on cross-sectional area measurements is deemed as not suitable for comparison of midgraft sections and anastomotic sections. Any comparison between midgraft sections and anastomotic sections need to be based on thickness data and ratio data.

Graft Patency

In both study groups, all 6 week implants were patent (open). After 12 weeks, 50% of the non-stented vein grafts ("controls") were patent and 75% of the stented vein grafts were patent, i.e., 25% of the stented vein grafts were occluded.

At 6 weeks, macroscopic assessment of lumenal dimensions showed that, in all baboons, there was a distinct difference between control grafts and Nitinol-stented grafts. While stented vein grafts had a delicate thin vein wall with an even lumen, controls (non-stented) showed marked wall thickening and irregular narrowing of the lumen. However, the inner diameter did not significantly differ between the two groups. Equally, the cross sectional area was not significantly different. In view of the markedly thickened wall and the dilated outside diameter of control grafts at implantation, intimal thickening partly compensated for the initial dilation after 6 weeks.

At 12 weeks, macroscopic assessment of lumenal dimensions showed that there were only two patent control (non-stented) vein grafts, both of which appeared grossly dilated. This dilatation led to an increase of 163% in cross sectional area. In contrast, the stented vein grafts underwent a mild decrease of 21% in the lumenal cross-sectional area. The wall thickness seemed less pronounced after 12 weeks than after 6 weeks.

Data from Midgraft Region and Anastomotic Regions

Measurements of Midgraft region: The lumenal cross-sectional area was 16.9±5.2 mm2 (42 days) and 44.3±3.8 mm2 (84 days) in the non-stented group and 19.6±2.3 mm2 (42 days) and 16.3±1.3 mm2 (84 days) in the stented group. Intimal hyperplasia (IH): The mean IH thickness was 110.5±6.8 μm (42 days) and 67.3±15.0 μm (84 days) in non-stented vein grafts and 5.1±5.1~Lm (42 days) and 12.2±12.2 μm (84 days) in stented vein grafts. Cross-sectional IH area was 1.6±0.2 mm2 (42 days) and 1.7±0.4 mm2 (84 days) in the non-stented vein grafts and 0.1±0.1 mm2 (42 days) and 0.2±0.2 mm2 (84 days) in stented vein grafts. The difference of IH area between the non-stented group and the stented group was statistically significant at 42 days (p=0.001) and at 84 days (p=0.02). Media: The mean thickness of the media layer was 197.6±11.3 μm (42 days) and 85.1±7.2 μm (84 days) in non-stented vein grafts and 102.6±13.8 μm (42 days) and 44.4±6.2 μm (84 days) in stented vein grafts. The cross-sectional media area was 2.9±0.1 mm2 (42 days) and 2.2±0.1 mm2 (84 days) in the non-stented group compared to 1.5±0.2 mm2 (42 days) and 0.6±0.1 mm2 (84 days) in the stented group. The difference in cross sectional media area between the two groups was statistically significant at 42 days (p=0.002) and at 84 days (p=0.004). Adventitial hyperplasia (AH): The mean thickness of adventitial hyperplasia was 313.1±21.6 μm (42 days) and 137.0±5.8 μm (84 days) in non-stented vein grafts and 343.5±79.4 μm (42 days) and 177.4±49.5 μm (84 days) in stented vein grafts. The cross-sectional AH area was 4.5±0.5 mm2 (42 days) and 3.1±0.1 mm2 (84 days) in the non-stented group compared to 4.9±1.1 mm2 (42 days) and 2.3±0.6 mm2 (84 days) in the stented group. The difference of AH area between of non-stented grafts and stented grafts was statistically not significant at 42 days (p=0.8) and at 84 days (p=0.4).

Proximal anastomosis: Mean pannus thickness was 192.6±55.5 μm (42 days) and 393.6±279.1 μm (84 days) in non-stented vein grafts and 122.0 μm (42 days) and 260.34±151.9 μm (84 days) in stented vein grafts. Mean media thickness was 183.6±14.3 μm (42 days) and 118.9±52.4 μm (84 days) in the non-stented group compared to 170.2 μm (42 days) and 273.6±153.2 μm (84 days) in the stented group. Mean AH thickness was 433.1±36.2 μm (42 days) and 256.4±63.0 μm (84 days) in the non-stented group compared to 594.8 μm (42 days) and 597.8±159.6 μm (84 days) in the stented group.

Distal anastomosis: Mean pannus thickness was 309.7±74.3 μm (42 days) and 64.5±50.8 μm (84 days) in non-stented vein grafts and 401.6 μm (42 days) and 49.8±19.2 μm (84 days) in stented vein grafts. Mean media thickness was 224.9±23.7 μm (42 days) and 80.8±5.2 μm (84 days) in the non-stented group compared to 159.7 μm (42 days) and 63.8±13.7 μm (84 days) in the stented group. Mean AH thickness was 383.5±23.4 μm (42 days) and 250.7±28.2 μm (84 days) in the non-stented group compared to 318.5 μm (42 days) and 245.2±10.7 μm (84 days) in the stented group.

Summary

In non-stented grafts, exposure to arterial pressure led to a nearly 70% increase in lumenal diameter, intimal hyperplasia was pronounced after 6 weeks and over-corrected the 70% distension to below the in-situ dimensions, and between weeks 6 and 12, the dominant event was excessive dilation (±170%), with stagnant intimal hyperplasia. Since maximal adventitial distension was the starting point, vein graft dilation must be a result of failed remodeling. Successful remodeling would have re-established the flow-velocity of the artery, to which the vein was anastomosed, by narrowing the lumen. The loosely arranged and non-oriented media became mildly compacted and moderately aligned.

In stented vein grafts (using non-compliant stents), there was practically no intimal hyperplasia either after 6 weeks or after 12 weeks. The 5 mm stent used in the study matched the in-situ size of the vein in this model (with very mild downsizing). The lumenal dimensions of stented grafts remained fairly constant over 12 weeks. The mild reduction in lumenal cross-sectional area after 12 weeks was rather due to adventitial tissue development than intimal hyperplasia. The loosely arranged media of the vein re-modeled within 6 weeksdays to form a compact, circularly aligned media. The non-compliant stent protection appeared to be responsible for the semi-atrophic development of a thin media and the lack of growth between 6 weeks and 12 weeks. The exposure of non-stented grafts to arterial pressure led to nearly 70% increase in lumenal diameter. Intimal hyperplasia was pronounced after 6 weeks days and over-corrected the 70 distension to below the in-situ vein dimensions. Between 6 and 12 weeks, the dominant event was excessive dilation (±170%), with stagnant intimal hyperplasia. The loosely arranged and non-oriented media became mildly compacted and moderately aligned. Since maximal adventitial distension was the starting point, it is proposed that vein graft dilation was a result of failed remodeling. Successful remodeling would have re-established the flow-velocity of the artery, to which the vein was anastomosed, by narrowing the lumen.

Example 2

Stent Size: Effect of Down-Sizing and Oversizing of External Reinforcement of Vein Grants on Remodeling of Veins Transposed Into Circulation A baboon bilateral femoral artery vein graft model was used in a two-factor study to assess the effect of stent size in stented femoral vein grafts at two implant durations. A "senescent Chacma Baboon" model, with the superficial femoral vein used as end-to-end interposition graft in the superficial femoral artery, using protocols similar to those described in Example 1, above, was used to implement a study design wherein one experimental group of four (4) baboons was implanted with vein grafts externally stented with non-compliant Nitinol braided stents of 6.6 mm internal diameter (Group 1, "6.6 mm stented vein grafts"), and one experimental group of four (4) baboons was implanted with vein grafts externally stented with non-compliant Nitinol braided stents of 3.3 mm internal diameter (Group 2, "3.3 mm stented vein grafts"), for each of two time points (6 weeks and 12 weeks). The 3.3 mm stented vein grafts and 6.6 mm stented vein grafts were implanted bilaterally in any one of 8 animals. The stented veins were down-sized to 73% of the unrestricted outer diameter in venous circulation in the 3.3 mm group while the stents were over-sized by 40% of the unrestricted outer vein diameter in the 6.6 mm group.

Protocols

Stents were made from a Nitinol (NiTi)-wire tubular braid material, assumed to be non-compliant in the radial direction and thus, not permitting any change in diameter due to changing blood pressure. The stents were manufactured according to the specifications required for the study. Since the principal stent parameter in this study was the size (=diameter) of the stent, manufacture was aimed at achieving stents of different size but the same, or at least sufficiently similar, mechanical properties, especially compliance. The stents of different diameter developed for this study exhibit the same pitch (distance) between adjacent Nitinol wires, i.e. the same number of wires per unit length, and the same pitch angle to obtain similar stent properties. To achieve consistency in pitch distance and pitch angle but different stent diameters, the number of carriers (wires) in the braid was varied for each stent. The 3.34 mm stents have 24 carriers, and the 6.68 mm stents have 48 carriers. The wire thickness of 0.05 mm (0.002") was determined according to manufacturing requirements (Medtronic AVE, Danvers Mass.). The pitch distance and pitch angle was chosen in accordance with the 36-carrier stents with 0.025 mm as used in Example 1 above. Hence, it is assumed that the compliance of the 3.34 mm stents and 6.68 mm stents used in this study are in the same range or lower than that of the 36-carrier stents used in the study described in Example 1 above.

Surgical protocols, explantation, sample processing, and vein graft assessments were essentially as described in Example 1, above. The 3.3 mm stented vein grafts and 6.6 mm stented vein grafts were implanted bilaterally in any one of 8 animals following preoperative randomization. The mean outer diameter of the superficial femoral veins were 4.5±0.5 mm and 4.6±0.1 mm in the 3.3 mm stented group and 4.6±0 6 mm and 4.8±0.1 mm the 6.6 mm stented group; indicating the degree of down-sizing of the vein in the 3.3 mm group and of over-sizing of the stent in the 6.6 mm group. The mean length of the vein grafts was 50.8±4.5 mm and 44.0±3.6 mm (3.3 mm stent group), and 51.0±5 4 mm and 43.8±4.1 mm (6.6 mm stent group). The lumenal cross-sectional a It should be noted that the diameter of the stent at implantation was measured at the graft diameter after cross-clamp release (see protocols in Example 1, above), while stent diameter at explantation was measured by means of microscopic image analysis of histological slides of cross sectional midgraft sections.

Graft Patency

There was no change in patency between vein graft size or over time. Graft patents was 75% (¾) in all experimental groups, independent of vein graft size (3.3 mm vs. 6.6 mm) or implant duration (6 weeks (42 days) vs. 12 weeks (84 days).

Data from Midgraft Region and Anastomotic Regions

Midgraft region: The lumenal cross-sectional area was 9.0±0.3 mm2 (42 days) and 7.4±0.3 mm2 (84 days) in the 3.3 mm group and 22.2±5.0 mm2 (42 days) and 23.6±1.5 mm2 (84 days) in the 6.6 mm group. Intimal hyperplasia (IH): The mean IH thickness was 1.6±1.6 nm (42 days) and 11.3±5.7 nm (84 days) in the 3.3 mm vein grafts and 112.6±62.6 nm (42 days) and 158.5±34.0 nm (84 days) in the 6.6 mm vein grafts. Cross-sectional IH area was 0.02±0.02 mm2 (42 days) and 0.11±0.06 mm2 (84 days) in the 3.3 mm vein grafts and 2.0±1.0 mm2 (42 days) and 2.9±0.9 mm2 (84 days) in the 6.6 mm vein grafts. The difference of IH area between the 3.3 mm group and the 6.6 mm group was statistically not significant at 42 days (p=0.11) but significant at 84 days (p=0.04). Media: The mean thickness of the media layer was 40.1±10.5 μm (42 days) and 22.8±3.5 μm (84 days) in the 3.3 mm vein grafts and 197.9±65.2 μm (42 days) and 156.8±39.7 μm (84 days) in the 6.6 mm vein grafts. The cross-sectional media area was 0.5±0.1 mm2 (42 days) and 0.22±0.03 mm2 (84 days) in the 3.3 mm group compared to 3.6±0.9 mm2 (42 days) and 2.9±0.9 mm2 (84 days) in the 6.6 mm group. The difference in cross-sectional media area between the two groups was statistically significant at 42 days (p=0.025) and not significant at 84 days (p=0.063). Adventitial hyperplasia (AH): The mean thickness of adventitial hyperplasia, defined as elastic tissue development between stent and adventitia, was 198.3±49.0 μm (42 days) and 125.1±9.9 μm (84 days) in the 3.3 mm vein grafts and 414.0±142.6 μm (42 days) and 545.4±100.6 μm (84 days) in the 6.6 mm vein grafts. The cross-sectional AH area was 2.0±0.5 mm2 (42 days) and 1.1±0.2 mm2 (84 days) in the 3.3 mm group compared to 8.0±3.0 mm2 (42 days) and 8.6±1.2 mm2 (84 days) in the 6.6 mm group. The difference of AH area between of 3.3 mm grafts and 6.6 mm grafts was statistically not significant at 42 days (p=0.12) but significant at 84 days (p=0.003).

Proximal anastomosis: Mean pannus thickness was 29.2±24.4 μm (42 days) and 47.1±25.8 μm (84 days) in the 3.3 mm vein grafts and 357.2±219.3 μm (42 days) and 105.5±44.7 μm (84 days) in the 6.6 mm vein grafts. Mean media thickness was 44.5±22.9 µm (42 days) and 78.8±16.4 µm (84 days) in the 3.3 mm group compared to 118.4±11.1 µm (42 days) and 134.4±35.4 µm (84 days) in the 6.6 mm group. Mean AH thickness was 157.3±44.5 µm (42 days) and 225.5±57.2 µm (84 days) in the 3.3 mm group compared to 657.3±132.1 µm (42 days) and 503.9±117.8 µm (84 days) in the 6.6 mm group.

Distal anastomosis: Mean pannus thickness was 45.8±33.9 µm (42 days) and 120.2±62.3 µm (84 days) in the 3.3 mm vein grafts and 222.9±76.3 µm (42 days) and 199.1±30.2 µm (84 days) in the 6.6 mm vein grafts. Mean media thickness was 75.5±5.7 µm (42 days) and 156.7±78.9 µm (84 days) in the 3.3 mm group compared to 191.2±30.0 µm (42 days) and 132.4±32.6 µm (84 days) in the 6.6 mm group. Mean AH thickness was 228.4±82.9 µm (42 days) and 355.5±139.3 µm (84 days) in the 3.3 mm group compared to 660.1±96.1 µm (42 days) and 505.5±190.8 µm (84 days) in the 6.6 mm group.

Summary

Comparison of vein grafts in the 3.3 mm stent group versus the 6.6 mm stent group showed no difference in graft patency. Macroscopically, the intima was very delicate in 3.3 mm stent group but thick and white in 6.6 mm stent group. Endothelial damage was exclusively confined to 6.6 mm stent group. Circular micro-folds of the intima were found mostly in 3.3 mm stent eSVS group.

Results from this study can be compared with results from the study described in Example 1 above, to assess additional factors. Intimal hyperplasia (IH) was more pronounced in oversized 6.6 mm stent group of the present study than in non-stented control group of Example 1. Intimal hyperplasia continued to increase (cross sectional area wise) beyond 6 weeks in the stented vein grafts of the present study, in contrast to non-stented controls vein grafts of Example 1. Downsizing of vein grafts with 3.3 mm stents was shown in the present study to be as good as using stents matching the ideal vein sizing, i.e., the 5 mm stents used in Example 1, above.

In the down-sized stented grafts, i.e., the 3.3 mm stent group, no intimal hyperplasia (IH) was measured at 6 weeks, and very limited intimal hyperplasia was measured at 12 weeks. Very thin and delicate media was seen. Atrophy happened rapidly during first 6 weeks with no further "thinning" of the media thereafter. No adventitial hyperplasia (elastic tissue development between stent and adventitia) was measured. The inner surfaces of the veins had confluent endothelium.

In the over-sized stented grafts, i.e., the 6.6 mm stent group, intimal hyperplasia (IH) was distinct (⅓) to mild (⅔) at 6 weeks, and mild (¼) to moderate (¼) to distinct (¼) to massive (¼) at 12 weeks. Clear elastic demarcation between intimal hyperplasia layer and media was seen both at 6 and 12 weeks. Media layer was more pronounced than in non-stented vein grafts ("control" group) of Example 1, above. The inner surves of the veins had semi-confluent to completely denuded endothelium.

Thus, downsizing of vein grafts with external mechanical support by means of braided Nitinol stents (here, 3.3 mm stents) considerably limited the intimal and adventitial hyperplastic response, and prevented endothelial damage, compared to vein grafts with oversized external stent support (here, 6.6 mm stents). Intimal and adventitial hyperplastic response in downsized vein grafts was of a lower degree than in vein grafts with size-matching external support and non-stented vein grafts shown in Example 1, above. Intimal hyperplasia (IH) in vein grafts with oversized external support exceeded the intimal hyperplasia in non-stented vein grafts shown in Example 1, with the development of IH tissue in grafts with oversized support progressing beyond 42 days implantation, while it stagnated after 42 days in non-stented vein grafts. Downsizing of vein grafts with external stents was found to be superior to oversized external support, and as good as external mechanical support matching the size of the vein in venous circulation.

Example 3A

Determination of In Vivo Compliance of External Saphenous Vein Stented Grafts Via Ultrasound Measurements in Canine Femoral Graft Model System A two-factor study varied graft design and implant duration, i.e., implanting a non-stented vein graft (also called "vein alone") or a stented vein graft with, for different implant durations. Ultrasound examination was used to show that a saphenous vein graft supported by a radially-compliant external stent results in an in vivo graft which continues to show radial compliance throughout the healing phase. Briefly, four (4) canines were implanted, each with one non-stented vein graft and one stented vein graft. Ultrasound measurements were made at 2, 4, 8, and 12 weeks after implantation to track graft patency and to estimate in vivo compliance values. At 12 weeks after implantation, grafts were explanted and prepared for histological evaluation.

Protocols:

Four (4) adult female canines were implanted with autologous vein grafts as described below. Each animal was implanted with one non-stented vein graft and one stented vein graft. The implanted vein grafts were removed from the femoral venous position of each animal and transposed to the corresponding lateral arterial position. The position of the non-stented and stented vein grafts were alternated between left and right femoral positions, from one study animal to the next.

The tubular members, or stents, used in the study were knitted nitinol (NiTi) wire, even knit design, open mesh tubes with 3.3-mm ID. A "#2 model" stent was made from a 0.05 mm OD nitinol wire. A "#6 model" stent was made from a 0.0375 mm OD nitinol wire product.

All current standard operating procedures (SOP) for the study site (Physiological Research Laboratories (PRL), Medtronic, Inc., Minneapolis, Minn.) were followed, compliance with comply with the Animal Welfare Act of 1966 (P.L. 89-544), and all amendments, and registrations and accreditations with agencies and organizations involved in laboratory animal welfare, and in adherence to laboratory animal welfare principles stated in *The Guide for the Care and Use of Laboratory Animals* U.S. Department of Health and Human Services, Institute of Laboratory Animal Resources, Commission on Life Sciences, National Research Council, National Academy Press (Revised 1996, ISBN 0-309-05377-3; NIH publication no. 86-23).

Vein Graft Procedures

With the animal in supine position, an incision was made in each groin and the superficial femoral vessels between the deep femoral artery proximally and branching sites distally were carefully dissected out without touching them, in an effort to prevent spasm. Once sufficiently exposed, the diameter of the segment of vessel to be transplanted was determined by approximating the jaws of a vernier caliper, and these values recorded. A lower magnification photograph showing both in situ vessels was taken, and a higher magnification photograph of each in situ vessel by itself was taken After photography, 250 U/kg of IV heparin was administered and allowed to circulate. A 5 cm segment of the vein between the proximal and distal branching sites was measured and circumferentially marked with methylene blue. Vascular clamps were applied both proximally and distally, and the marked segment was excised. An additional 1 cm of the remaining proximal vein was taken, placed over a 5 mm pipette (to keep vein dilated) and fixed in formalin for control histology. A 5 cm segment was marked on the artery before applying the clamps, to control for possible distortion of the length of vessel excised, due to longitudinal contraction of the artery upon excision. The distance from the deep femoral artery was at least 1 cm to accommodate the anastomosis-protecting extra length of the stent.

Fixed left and right femoral vein segments collected as described above were preserved as "controls" for comparison with the stented grafts. Additionally, a proximal 1 cm portion of each excised femoral artery segment was removed and placed in fixative, to provide arterial tissue controls.

Placement of the Stent

Clamps were applied to the artery proximally and distally, and the marked artery segment was excised. The proximal end-to-end anastomosis of the reversed femoral vein to femoral artery was performed with a running suture of 7/0 Prolene. When this procedure was completed, a 7 cm length of the stent was cut. A single stay suture of 7/0 Prolene was applied to the adventitia of the vein and then fed through the stent, whereafter the stent was gently slid over the vein graft while using the stay suture as a guide. The distal anastomosis was completed with a running suture of 7/0 Prolene. Before tying the suture, the graft was flushed, first from the distal end, then from the proximal end. The clamps were then removed and flow was re-instated. At this time, any anastomotic leaks were addressed. Once hemostasis of the tension-free anastomosis was verified, and flow in the anastomosed vessels was verified by inspection and palpation, the stent was fixed approximately 1 cm proximally and 1 cm distally to the anastomosis with two adventitial stay sutures on either side.

Immediately after implantation, each device was photographed in situ ("implant macro-photographs") to document the left- or right-sided nature of the implant and the degree of anastomotic size matching, while the implant ID#, the animal number, and the date of implantation were noted on the photograph worksheet. The diameter of the grafted vessels was measured at that point and recorded, and the diameter was recorded again approximately ten minutes after removal of the clamps.

Placement of Non-Stented Vein Grafts

Non-stented vein grafts, i.e., vein grafts without the stent, were implanted in each contralateral position, according to the procedure described above, minus application of the stent over the adventitia of the vein. For non-stented vein grafts, each animal served as its own "control" as the grafted vein segment was removed from the femoral venous position of each animal and transposed to the corresponding lateral arterial position of the same animal.

Closure and Post-Implantation Care

The groin incisions were then closed in two layers with absorbable 2/0 Vicryl sutures for subcutaneous closure, and 2/0 Nylon for skin closure. Following implantation, anticoagulants were administered to each animal, and antibiotics were administered as deemed necessary pursuant to ongoing veterinary supervision.

Termination, Explantation, and Preparation of Specimens for Histological and Scanning Electron Microscopy Analysis After the final in vivo ultrasound measurement (under anesthesia) was completed at 12 weeks, animals were terminated. Animals were administered acepromazine, and induce using either a short-acting barbituate or a short-acting hypnotic, and maintained on isoflurane. For femoral venotomy, the animal was placed on its back. The proximal iliac arteries or superficial femoral artery were isolated and perfusion lines were inserted.

In-Situ Perfusion Fixation (IPF)

For IPF, as applied to biomedical implant retrieval, fixative was injected into the vascular system at physiological pressure to preserve the device and associated tissue(s) or organ(s) in the in-vivo or natural configuration. Briefly, IPF on the lower extremity vasculature involves exposure of the proximal superficial femoral artery (SFA). After administration of 500 I.U. heparin per kg following a lethal potassium chloride bolus injection and confirmation of cardiac arrest, the SFA was ligated proximally and distally of the implanted vascular graft. Within the ligations, a perfusion entrance line was tied proximally and a perfusion exit line was placed distally of the implanted graft for release of perfusion fluids to a drain. A clearing buffer solution was delivered by pressure controlled delivery into the SFA, to clear all the blood from the lower extremity. The injection pressure was monitored via a pressure line connected via a three-way-stopcock at the entrance line. In this manner, IPF at approximately 100 mmHg was initiated within 5 minutes of cardiac arrest. Shortly after the exit fluid became clear with clearing buffer solution, the clearing buffer was replaced by buffered formaldehyde fixative solution. The tissues rapidly become very stiff from the cross linking of the tissues by the fixative. The device(s) and/or area(s) of interest are then carefully removed en bloc while avoiding excessive handling and air-drying of the explant specimen. The explant was immediately rinsed in the same buffer and submersed under the same formaldehyde fixative for storage and shipping. A standard histological workup of stented graft explants.

Graft Patency: Determination of Vein Graft Diameters and Compliance in Vivo Using Ultrasound Measurements The original study plan proposed recording ultrasound measurements of the proximal artery, proximal anastomosis, mid-graft, distal anastomosis, and distal artery. Due to concerns that a vascular probe could damage the internal wall of the vessels immediately after the transplant, different ultrasound measurements were taken.

Pre- and post-implantation compliance, size and patency (vessel diameter and occlusion/dilation) of each non-stented vein graft and each stented graft were measured using the vascular probe on a GE ultrasound machine under anesthesia. Ultrasound measurements of $A_{systole}$, $D_{systole}$, $A_{diasystole}$, and $D_{diasystole}$ were made for each non-stented vein graft and each stented vein graft, at pre-implantation, and at 2, 4, 8, and 12 weeks post-implantation, at the following locations: proximal artery (PArt); proximal anastomosis (PAna), midgraft (MG), distal anastomosis (DAna), and Distal Artery (DArt). Ultrasound measurements were an average of at least two determinations using ultrasound vascular planimetry software.

Diameter (D) at each location was calculated from the A (lumen cross-section area) value measured at that location ($A_{location}$) using the formula $A_{location} = \pi D^2/4$. Vein diameters were generally higher in the non-stented vein grafts than the stented vein grafts.

Compliance at each location was calculated as follows: % Compliance=$\{[D_{systole}-D_{diastole}/D_{diasystole}]\}/[P_{systole}-P_{diasystole})/100]\}*100$, where D is diameter, and P is pressure. Compliance data measured in vivo indicated that compliances for both the non-stented vein grafts and stented vein grafts, in the mid-graft region, appeared to fall in the 5-15%/100 mm Hg range. Based on literature values suggesting natural vessel compliance to be in the range of 4-10%/100 mm Hg, with lower values for veins than for arteries, the in vivo compliance values measured for vein grafts were considered to be within the range of compliance values of natural vessels.

These in vivo compliance measurements were compared with known in vitro compliance measurements of 8-21 of the #2 model stents and 21-29 of the #6 model stents used in this study. It was expected that implanting highly radially-compliant stents may invoke more natural healing. Specifically, the known in vitro compliance values, combined with a low level of scarring after grafting, was expected to potentially create a graft with an in vivo compliance levels consistent with a native artery. A more "physiological" level of graft compliance was thought to be a crucial factor in creating an arterial-like reorganization of the venous tissue, which would result in high graft patency.

Evaluation of Explanted Vein Grafts

As described above, animals were euthanized 12 weeks post-implantation (77 days), following the final ultrasound measurement. The grafts were subject to gross examination, explantation, and evaluation by various methods including histological evaluation, e.g., light microscopy of stained fixed sections or scanning electron microscopy (SEM) of fixed sections, or evaluation of faxitron (radiograph) images of grafts. Photographs were taken of intact grafts before excising, explanted grafts, and fixed vessels and vessel sections in certain animals.

Gross examination of explanted non-stented and stented vein grafts showed similar smooth, glistening lumens. In the explanted stented vein grafts, the stent structure was clearly visible through the thin vein wall. Some regions of stent wire disruption could be seen in the lumenal view of the stented vein graft explants.

Fixation and Histological Evaluation

Histological examination showed that the healing response was very similar between the two types of stents, i.e., the #2 model and the #6 model. Little, or no, inflammatory response to the metal stents was observed. The diameters/cross sectional areas were measured, and by graphical analysis of the measurement, it was determined that non-stented vein grafts (controls) had slightly larger diameter/cross sectional area values than the stented vein grafts. The diameters/cross-sectional areas appears similar in each type of graft, regardless of the stent employed, i.e., the #2 model or the #6 model. Endothelization, measured as % endothelial cell coverage, was similar (at or near 100%) in stented and non-stented grafts.

Resin-embedded explant sections were actin-stained for vessel wall measurements and evaluation of structures, e.g., wall thickness and extent of elastin cushioning. Intimal hyperplasia and medial hyperplasia (mean medial thickness) were measured as an indicator of wall thickening, which was considered to correlate with proliferation and/or injury. Low levels of intimal or medial hyperplasia were observed with the metal stents.

Scanning electron micrographs (SEM) of all grafts, stented and non-stented, showed relatively intact endothelium on all explanted vein grafts.

Faxitron (Radiographic) Evaluation

Faxitron (radiographic) images revealed the extent of non-stented vein graft size and dilation, relative to the femoral artery to which it was attached. The stented vein grafts showed a certain degree of dilation in certain locations. Careful inspection of the images showed that the dilation was mainly located in the portion of the stent covering the vein graft. The portion of stent overlapping the proximal and distal artery did not appear to show dilation. Regions of the dilating portion of the stent showed a small amount of wire breakage and/or disruption in the normal knitted pattern. The latter observations appear consistent across each stent design, i.e., the #2 model and the #6 model.

Evaluation of the particular stent designs used in this study, i.e., the #2 model and the #6 model, indicated that these stent designs appear to show some level of in vivo radial 'creep' which is inconsistent with other similar implants. The reason for the observed radial creep was not determined, but it was speculated that loop design and supra-physiological compliances of these designs may be a factor. Other implants utilizing an uneven loop design, e.g., the "K1 design" extensively tested in other studies, did not show radial creep as observed here. The #2 model and the #6 model stent designs had uneven loop design, with 8 loops per circumference, with loops alternating between an large and small size, creating an alternating geometry that may make the stent slightly more rigid, in addition to adding stability to the structure. However, further investigation is necessary to rule out other potential sources of the problem observed here, e.g., poor quality wire lots and insufficient annealing.

Example 3B

Surgical Methodology and Healing Response Characterization of the Stent Device in the Coronary Vasculature in a Canine Model The study had a three-fold purpose to develop surgical methodology, characterize the healing response, and determine if one or both stented grafts perform better than the non-stented control vein graft. More specifically, one goal was to develop and refine the best methodology to apply a stented graft in the aorto-RCA coronary or aorto-LAD position such that it optimally covers and is attached to the proximal and distal anastomotic regions. A second goal was to contrast the healing response of the stented grafts versus the non-stented control vein graft in terms of healing and patency.

This study successfully employed a surgical methodology in a canine model to apply the stent during a coronary artery bypass grafting ("CABG") procedure. It was determined that the femoral vein was more suitable in this canine model than the saphenous vein, due to vessel size and fit within the stent. Briefly, five female dogs underwent a femoral vein graft harvest followed by a beating heart aorto-coronary bypass with four (4) animals receiving a stented vein graft, and two (2) receiving the autologous femoral vein without a stent. Vein grafts were monitored in vivo following implantation. Twelve weeks after vein graft implantation, the vein grafts were removed.

The stents used in the study were K1 model knitted NiTi (Nitinol) wire mesh compliant stents, uneven design, 7 cm or greater length, 3.3 mm ID (Danvers Model K1, Medtronic Vascular, Danvers Mass.). The stents were supplied mounted on 9 Fr removable plastic tubes, where the tubes were provided for facilitating vein graft insertion through the stent lumen. The "control" articles were autologous femoral vein without a stent, and the control treatment is the vein graft without a stent, i.e., the "non-stented vein graft."

Surgical Procedures

The femoral vein was harvested from the right leg of each animal. After completion of the harvest the leg was closed. The distal end of the harvested vein was marked.

The CABG procedure was performed as an off-pump procedure (Beating Heart) utilizing Medtronic Starfish™ and Octopus™ products to stabilize the heart during the operation. The proximal anastomosis of the vein graft to the ascending aorta was performed first, using a partial sidebiting clamp to the aorta. The artery was momentarily clamped while the arteriotomy was performed and inserted into the coronary artery to ensure distal perfusion while the anastomosis was being performed. Once completed, the left anterior descending (LAD) or right coronary artery (RCA) was ligated just proximal to the anastomosis. After completing the proximal anastomosis, a suture was tied to the distal vein tissue and the vein was carefully pulled through the stent lumen. The distal anastomosis was completed, with optional stay sutures added to this anastomotic region to prevent stent dislodgement.

The vein graft control was implanted applying the procedure described above without the stent applied to the grafted vein.

Three animals received a stent over a femoral vein graft (approximately 7 cm length), one animal served as an autologous non-stented femoral control, and one animal received an autologous saphenous vein graft. To examine the ease and need of stay sutures to hold the stent in place over the vein graft, some stents received 2-4 stay-sutures at the anastomosis.

Photographs were taken of implanted stented (test) grafts and control (non-stented) grafts showing: (1) image of entire graft on heart and revealing both anastomoses; (2) a close-up image of the anastomosis to the aortic arch; and (3) a close up image of the anastomosis to the coronary artery. In addition, each procedure was videotaped.

All dogs recovered from surgery. Two of the five dogs fibrillated during the surgery, one immediately upon reperfusion of the heart, and one just prior to closing the thoracotomy. Both dogs were successfully resuscitated using defibrillation and drug administration. One dog received a saphenous vein graft. Here, some difficulty was encountered due to the small size of this vessel. As a result, all subsequent dogs received a femoral vein graft. All animals had minimal swelling/edema in the limbs where the femoral or saphenous vein was harvested. Three dogs remained on procainamide for 3-5 days post-operatively due to arrhythmias noted on their daily ECG's. Release of cross clamps before positioning of the stent prevented optimum positioning of the stent. The need for placement of the stay sutures was unclear at implant, as the blood-filled vein graft appeared to hold the stent in place. The stay sutures were technically difficult to apply.

The implants (grafts) were examined by ultrasound monitors that took place at 2, 4, 8, and 12 weeks after graft implantation.

At 12 weeks after implantation (grafting) and prior to sacrifice, the grafts were examined by in vivo angiography and intravascular ultrasound (IVUS). Following the ultrasound monitor, the heart was perfused via a cardiac perfusion fixation chamber and perfusion-fixed in situ and the grafts removed en bloc. Fixed explants underwent Faxitron imaging (radiography), gross photography, SEM of lumenal surfaces, and histopathology using routine paraffin and plastic resin preparation.

Example 4

External Saphenous Vein Stents: Effect of Radial Compliance on Vein Healing Response Sixteen (16) Chacma baboons were implanted with a total of thirty-two (32) vein grafts in a three-factor study to evaluate the effects and interactions of stent design (braided vs. knitted), radial compliance (low (non-crimped) vs. high (crimped)), and implant duration (6 weeks vs. twelve weeks).

In this study design, radial compliance of a stent of a given design was adjusted by crimping or not crimping the stent, where crimping increased the radial compliance of both stent designs, in accordance with disclosures elsewhere in the application (See, e.g., Table III). That is, a braided stent material (B1 design, Medtronic AVE, Danvers Mass.) having a low radial compliance value was used for the braided stents, where high compliance braided stents resulted from crimping the braided stent material, and low compliance braided stents resulted when the braided stent material was left alone (non-crimped). The same relationship applied for the knitted stents (K1 design, Medtronic AVE, Danvers Mass.). Thus, the stents used for this study included (1) non-crimped braided stents with a 3.3 mm ID having low radial compliance of about 1%/100 mmHg, or "low compliance non-crimped braided stents"; (2) crimped braided stents with a 3.3 mm ID, having high radial compliance of about 6%/100 mmHg, or "high compliance crimped braided stents"; (3) non-crimped knitted stents with a 3.3 mm ID having low radial compliance of about 3-4%/100 mmHg, or "low compliance non-crimped knitted stents"; and (4) crimped knitted stents with a 3.3 mm ID, having high radial compliance of about 9%/100 mmHg, or "high compliance crimped knitted stents." In this study, To ensure the connection between crimping Each animal was implanted was implanted with one high compliance stent and one low compliance of the same design (knitted or braided), and placement of the high and low compliance stents was randomized between right and left femoral artery position. Animals were grouped in "blocks" of four (4) animal per block, such that each block was sufficient to achieve all combinations of stent design (knitted or braided) and radial compliance (high or low), for one implant duration (6 weeks or 12 weeks). Two (2) blocks having an implant duration of 6 weeks and two (2) blocks having an implant duration of 12 weeks achieved full implementation of the experimental design. At 6 weeks or 12 weeks after implantation, grafts were evaluated for patency and explanted for visual and histomorphological analysis and ultrastructure analysis by scanning electron microscopy (SEM).

Baboons were chosen for these studies since the size and anatomy of the cardiovascular system were considered clinically relevant for the purpose of externally stented vein graft testing. The diameter of the femoral vessels approximates the nominal 3-4 mm ID of the test vein stents being developed for human use. This model is also generally acknowledged to show a healing response similar to humans, as demonstrated in previous stented vein grafts studies described herein and elsewhere. Because stent performance is influenced by the degree to which the stent fits over the saphenous vein it surrounds, the weight range of the Chacma baboons was restricted to 18+/−5 kg.

Treatment of study animals was in compliance with the Animal Welfare Act of South Africa and subsequent amendments, and pursuant to accreditation by the Association for Assessment and Accreditation of Laboratory Animal Care, International (AAALAC), and was further in adherence to animal welfare principles stated in The Guide for the Care and Use of Laboratory Animals—National Academy Press (Revised 1996, NIH publication no. 86-23).

The test materials used for stents were: eight (8) low compliance non-crimped braided stents; eight (8) high compliance crimped braided stents; eight (8) low compliance non-crimped knitted stents, and eight (8) high compliance crimped knitted stents As noted above, all stents have a 3.3 mm ID.

Protocols

All stents were cut to the length of 70 mm using surgical scissors, sterilized, and labeled. Prior to surgery, each animal was anesthetized, intubated with a endotracheal tube, and the operative fields were shaved.

With the animal in supine position, an incision was made in each groin and the superficial femoral vessels between the deep femoral artery proximally and branching sites distally were carefully dissected out without touching them in an effort to prevent spasm. Once sufficiently exposed, the diameter of the segment of vessel to be transplanted was measured by approximation using a vernier caliper. A lower magnification photograph showing both in situ vessels and a higher magnification photograph of each in situ vessel was taken. After 250 U/kg of IV heparin was administered and allowed to circulate, a 5 cm segment of the vein between the proximal and distal branching sites was measured and circumferentially marked with methylene blue. Vascular clamps were applied both proximally and distally and the marked segment will be excised. Another 1 cm of the remaining proximal vein was taken, placed over a 5 mm pipette and fixed in formalin for histological analysis of a control sample. In a similar fashion, a 5 cm segment was marked on the artery before applying the clamps, to accommodate possible distortion of excised length due to longitudinal contraction of the artery upon excision, as the distance from the deep femoral artery must be at least 1 cm to accommodate the extra length of the stent that protects the anastomosis.

After clamps were applied to the artery proximally and distally, the marked artery segment was excised and the proximal end-to-end anastomosis of the reversed femoral vein to femoral artery was performed with a running suture of 7/0 Prolene. The stent was cut to 7 cm (if necessary) and a single stay suture of 7/0 Prolene was applied to the adventitia of the vein and then fed through the stent, after which the stent was gently slid over the vein graft using the stay suture as a guide. The distal anastomosis was then completed with a running suture of 7/0 Prolene. Before tying the suture, the graft was flushed, first from the distal end, then from the proximal end. The clamps were removed and flow re-instated. At this time, any anastomotic leaks were addressed. Once hemostasis of the tension-free anastomoses was verified, and flow in the anastomosed vessels was verified by inspection and palpation, the stents were fixed approximately 1 cm proximally and distally to the anastomoses with two adventitial stay sutures on either side. The implant macrophotographs were taken at this point. The diameter of the grafted vessels was measured again approximately ten minutes after removal of the clamps. The groin incisions were closed in two layers with absorbable 2/0 Vicryl sutures for subcutaneous and 2/0 Nylon for skin closure.

Immediately after implantation, each device was photographed in-situ with a high quality digital camera, to document the left- or right-sided nature of the implant, the degree of anastomotic size matching, the implant ID#, the animal number, and the date of implantation.

First, results from the present study were analyzed by analysis of variance (ANOVA) with respect to each factor, and with respect to factor interactions in the full factorial study. Next, ANOVA analysis was carried out on results from the present study, combined with the results from the non-stented "control" group from the study described in Example 1 above, to gain additional perspective on the results and their implications. This approach was considered reasonable since the healing response(s) of each type of stented vein graft ultimately needs to be compared not just to other stented vein grafts within the present study, but also to a "normal" treatment group that received non stented vein grafts. In addition, the animal model, surgical methods, implants position, etc. used in both studies are identical. The main caveats associated with this comparison are (1) the level of one variable is different i.e., time point 2 is three months in study in Example 1, and six months in this study, and (2) the control group of Example 1 was not randomized into this study and was in fact done many months earlier in the program.

Assessment of Graft Patency

At the end of the study, there were 11/16 (69%) knitted vein grafts patent and 15/16 (94%) braided vein grafts patent. It was not clear whether the crimping feature was a factor in graft patency, but it should be noted that the single occluded braided vein graft was crimped, and 3 out of the 5 occluded knitted vein grafts were also crimped. The patency of the control non-stented grafts from the earlier study described in Example 1 was 6/8 (75%). The patency of these short stented vein grafts was expected to be high in the model used in the present study, and this result was observed. Given the small numbers of grafts involved, however, an exact logistic test on the patency data revealed that the differences were not statistically significant (P<0.0201). Therefore, in this study, patency was not considered a primary indicator of graft performance. The histomorphological assessments of the graft explants were therefore viewed as the best overall assessment of performance. Specifically, differences in pathological changes in the stented vein graft wall compared to the control non-stented vein graft, received the greatest attention.

As noted above, multiple measurements were compiled using histomorphological analyses. Given that many of the measurements are redundant with others, and some measurements are a simple mathematical manipulation of another measurement e.g., an area vs. a thickness, this results section reviews only three main measurement categories by ANOVA analysis: Calculated Mean Lumenal Diameter 'Mic'; Calculated Mean Medial Thickness; and Calculated Mean Intimal Hyperplasia. These measurements were chosen since they were considered to give a strong perspective of the patency/blood flow path of the implanted grafts, and a simple, accurate assessment of the degree of pathological thickening that may be occurring in the two upper-most lumenal layers of the vein graft. For statistical analysis of the measurement Mean Intimal Hyperplasia, the data received a log transformation to minimize variation and normalize the data.

ANOVA analysis of the present study was performed for the main study variables of stent design (braid vs. knit), radial compliance (low (non-crimped) vs. high (crimped)), and implant duration (42 days vs. 180 days). The ANOVA results are shown below in Table VIII.

TABLE VIII

Summary of ANOVA Results

| | Main Study Variables | | | |
| Measurement | eSVS Design (D) | Crimping (C) | Time (T) | Significant Interactions* |
| --- | --- | --- | --- | --- |
| Calculated Mean Lumenal Diameter 'Mic' | NS | NS | P < 0.0252 | DT |
| Calculated Mean Medial Thickness | NS | P < 0.0477 | NS | DT, DCT |

TABLE VIII-continued

Summary of ANOVA Results

| Measurement | Main Study Variables | | | Significant Interactions* |
|---|---|---|---|---|
| | eSVS Design (D) | Crimping (C) | Time (T) | |
| Calculated Mean Intimal Hyperplasia | P < 0.0033 | NS | P < 0.0305 | DT |

*P < 0.05 for any listed interactions
NS = not significant

Calculated Mean Lumenal Diameter 'Mic' Results

These results showed that in general over time i.e., implant duration, Calculated Mean Lumenal Diameter 'Mic' significantly increased. The overall mean lumenal diameter increased from 3.4 mm to 3.8 mm over the implant period. This was likely due to a gradual stretch/relaxation in the stent mesh structures. The significant Design-Time (DT) interaction observed here was that the vein grafts with knit design stents showed a relatively stable lumenal diameter over the implant period whereas the vein grafts with braid design stents showed a tendency for the lumenal diameter to increase over the implant period. 'Crimping' i.e., increased radial compliance introduced by crimping the stents, did not significantly influence vein graft lumenal area, as was dramatically illustrated in certain explant images wherein the crimped stents retained their 'star-like' morphology in vivo.

Calculated Mean Medial Thickness

As seen in Table 1, the results in this measurement category indicated that the crimped (high compliance) stents are generally associated with significantly more medial thickness than the non-crimped (low compliance) stents. A significant Design-Time (DT) interaction was also observed for this measurement, which reflects the observation that the braid stent design showed less medial thickness over the study period, while the knit stent design showed more medial thickness. See FIG. 4. The DCT interaction reflects that the data shows, in the absence of crimping, that medial thickness associated with both eSVS designs is the same over time (FIGS. 5 and 6 from JMP and DesignEase, respectively). However, with crimping, medial thickness over time becomes more pronounced on the Knit eSVS and less pronounced in the Braid eSVS (FIGS. 4 and 7 from JMP and DesignEase, respectively).

Calculated Mean Intimal Hyperplasia

As seen in Table VIII, the results in this measurement category indicated both the stent Design and Time influenced the extent of intimal hyperplasia, and that the trends were different in association with each design. Here it is seen that the amount of intimal hyperplasia associated with each stent design is similar at the early timepoint but that the amount is significantly higher in association with the knit stent at the later time point.

Examination of Responses in Comparison to Control Non-Stented Group from the Study in Example 1

The material above describes the healing response observations between each type of stented vein graft. This section now describes these results in comparison to the normal treatment group i.e., non stented vein grafts. For this, the data from the control non-stented group from stent Study 1 has been merged into the data for this study. Once again, it must be noted that the animal model, surgical methods, implants position etc. used in both studies are identical. However, caveats with this comparison are (1) the level of one variable is different i.e., the late time point 2 in stent Study 1 is 3 months rather than the 6 month as in stent Study 3-4, and (2) the control group was obviously not randomized into Study 3-4 and was in fact done many months earlier in the program in a separate block of study animals.

It should also be noted that in this secondary analysis the 'crimping' variable received special consideration and was ultimately excluded. To explain: the crimping feature was added to the overall investigation to see if any significant meaningful improved healing observation(s) could be associated with this feature. As Table 1 indicates, crimping had no impact on calculated mean luminal diameter or extent of intimal hyperplasia, but was seen to significantly (negatively) influence medial thickness. Therefore, crimping is viewed as a feature with no apparent benefit. It was possibly also associated with stent wire breakage, as broken stent wires were suspected in 8 knitted stents, 6 of which were crimped. With crimped stent designs excluded, the overall study takes the form of a simple 3×2 full factorial design looking at stent/graft design (knit(K) vs. braid(B) vs. control(C)) and time (early (T1) vs. late (T2)). Table IX below summarizes the significant ANOVA findings.

TABLE IX

Summary of ANOVA Results with Comparison to Control Grafts

| Measurement | Main Study Variables | | DT Interaction |
|---|---|---|---|
| | stent Design (D) | Time (T) | |
| Calculated Mean Lumenal Diameter 'Mic' | P < 0.0001 | P < 00014 | P < 0.0100 |
| Calculated Mean Medial Thickness | P < 0.0001 | P < 0.0004 | P < 0.0002 |
| Calculated Mean Intimal Hyperplasia | P < 0.0001 | NS | P < 0.0116 |

Comparison of Calculated Mean Lumenal Diameter 'Mic' Results Including Control Non-Stented Grafts With ANOVA analysis (Table IX) showing each main study variable and the interaction to be significant, and other results showing that in general lumen diameter associated with the control and braid groups significantly increased over time and that the lumen diameter of the knit group stayed relatively constant over this period.

Comparison of Calculated Mean Medial Thickness Results Including Control Non-Stented Grafts ANOVA analysis (Table IX) showed each main study variable and the interaction to be significant, and other results showed that in general, medial thickness associated with the control was significantly higher than that observed in the braid and knit groups, particularly at the early time point. The extent of medial thickness associated with the control group also significantly decreased over time compared to the stented groups. Medial thickness in the later groups remained relatively constant over the implant period.

Comparison of Calculated Mean Intimal Hyperplasia Results Including Control Non-Stented Grafts ANOVA analysis (Table 2) showed that the stent design variable and the interaction were significant, and other results showed that intimal hyperplasia was significantly pronounced in the control group compared to the stented groups at both time points. The results also showed that the level of intimal hyperplasia was low and similar in the stented groups and that the level of intimal hyperplasia significantly decreased over time in the control group.

Summary

The results of this stent study, without comparison to the earlier non-stented control group (Example 1), show a number of significant trends. The lumenal diameter of the stented grafts tended to increase over time but this was mainly attributable to the increase in diameter associated with the braid stent group over time. This change in diameter is a concern since, if dilation would continue, the purpose of the stent to maintain the purpose of the stent to prevent stretch injury to the vein and maintain a specified isodiametric blood flow path would be defeated. The use of longitudinal crimping to impart additional control to the blood flow path and the stent radial compliance did not lead to impressive changes in healing responses. Crimping of the stents generally lead to more medial tissue thickness, particularly in the knit stent group. The latter may have been in part due to broken stent wires, wherein wire damage itself may have started as a result of the crimping process (6 out of 8 suspected observations of broken wires occurred in crimped knitted stents). The crimped braided structure appeared to be more immune to such breakage. When the medial thickness data of the crimped knitted stents was removed from the database, braided and knitted stents show similar levels of medial thicknesses (around 50μ). Intimal hyperplasia thickness was low in both the braided and knitted stents but increased to a significant difference in the knitted stent implants by the late time point. The significance of this observation should be considered alongside the remarkably higher levels of intimal hyperplasia observed in control non-stented vein grafts.

The results of the present stent study, with comparison to the earlier non-stented control group (Example 1), also show a number of significant trends. As expected, the lumen diameter of the control non-stented group increased tremendously over time (from around 4.5 to 7.7 mm) compared to the braid stents (3.1 to 4.2 mm) and knit stents (3.6 to 3.5 mm) The apparent stability of the knitted stent graft lumen diameter may be important. The mean medial thickness in the control non-stented grafts was significantly higher than all other groups at the early time point, but fell to slightly above all groups at the later time point. The reason for this is unclear, as intuitively one might expect it to remain high. Additional testing at longer implant duration may help in the understanding of this process (also, recall the T2 control group is 12 weeks rather than 24 weeks for the stented grafts). Intimal hyperplasia was remarkably higher in the non-stented control group compared to stented grafts at both time points, but like medial thickness, it was slightly lower at the later time point. Patency was reasonably high in all graft groups in this study, but the difference in patency between the groups was found to not be statistically significant.

Example 5

External Saphenous Vein Stents: Impact of Stenting by Position (CABG vs. Femoral) and Vein Type (Lesser Saphenous vs. Femoral)

This study was carried out to evaluate the impact of stenting by graft position (aorto-coronary (CABG) vs. femoral) and grafted vein type (lesser saphenous vein vs. femoral vein). To study the impact of graft position, only lesser saphenous veins were used. To study the impact of grafted vein type, only femoral implants were used. The study design included two nested factorial studies: Study #1 ("S#1") had a 2×2×2 factorial design to evaluate stenting (stented vein vs. non-stented vein), autologous vein type (femoral vs. lesser saphenous), and fibrin glue (with and without glue); and study #2 ("S#2") had a 2×2 factorial design to evaluate stenting (stented vein vs. non-stented vein) and implant position (femoral vs. aorto-coronary). The study confirmed that externally stented vein grafts in the coronary position showed reduced intimal hyperplasia, thus improving the patency of coronary artery bypass grafts.

Study Design

In this study, regardless of the factor(s) being evaluated, each animal received (a) a lesser saphenous vein graft in the aorto-coronary (CABG) position; and (b) a lesser saphenous vein and a femoral vein graft in the bilateral femoral positions. Each animal received either stented grafts exclusively or non-stented grafts exclusively, for an implant duration of 180 days.

In the aorto-coronary graft position, grafts with a stent always received fibrin glue. Non-stented grafts in the aorto-coronary position were subdivided in two groups of n=8, where one group received fibrin glue and the other group did not receive fibrin glue. In the femoral graft position, both the stented animal group and the non-stented animal group were subdivided, such that half of each group (n=8) received fibrin glue and the other half of the animals did not receive fibrin glue. Therefore, in S#1, replication (n=) for these nested studies was n=8. In S#2, replication (n=) for these nested studies was between n=8 and n=16. The study design included the option that, should statistical analysis of the results from S#1 show no significant impact of fibrin glue, the replication in S #2 replication would become n=16 by factoring in all the non-fibrin-treated femoral grafts.

The study was designed to be carried out using a sample size based on the expected number of animals and procedures required to produce results suitable for application of statistical methods for determining significance. Briefly, a suggested sample size of 16 animals per group was based on the assumption that 35% of non-stented control grafts and 75% of stented grafts remain patent with a 75% probability of discerning a statistically significant difference at a p value of 0.05.

Chacma Baboon Model

Chacma baboons were chosen because the size and anatomy of the cardiovascular system of the Chacma baboon was expected to be clinically relevant for externally stented vein graft testing. The diameter of the saphenous and femoral vessels approximates the nominal 3-4 mm ID of the test vein stents developed for this and other studies. Further, the Chacma baboon model is generally acknowledged to show a healing response similar to humans, as demonstrated in other preclinical studies. Male baboons having weights between 29.3±63.2 kg were implanted with grafts as described below. The weight range of the Chacma baboons used in these procedures was in accordance with the understanding that the performance of each stent would be influenced by the degree to which the stent fit over the autologous vein it surrounded.

Treatment of study animals was in compliance with the Animal Welfare Act of South Africa and subsequent amendments, and pursuant to accreditation by the Association for Assessment and Accreditation of Laboratory Animal Care, International (AAALAC), and was further in adherence to animal welfare principles stated in The Guide for the Care and Use of Laboratory Animals—National Academy Press (Revised 1996, NIH publication no. 86-23).

Preparation of Stents for Grafting

At the beginning of the study, forty eight (48) knitted compliant K1 model stents having an ID=3.4 mm, length=200 mm, and radial compliance of about 3%/100 mmHg, were provided. The K1 model was knitted, with 8 loops per circumference, from a wire having a thickness of 0.002 inches (=0.05 mm), and had uneven loops. In accordance with the study design, 32 stents were to be grafted into a femoral position, and 16 stents were to be grafted in an aorto-coronary (CABG) position, where each position required a different stent length. The stents required for each animal receiving one or more stented grafts was as follows: one piece of 15 cm length for the CAB G stented grafts; and two pieces of 7 cm length for the bilateral femoral stented grafts.

The stents were cleaned after heat setting in the following two-step process before the stents were ready for implantation: 1) sonication in de-ionized water (50 ml per 60 cm length of stent, for 5 minutes at room temperature); and 2) sonication in isopropanol (50 ml per 60 cm length of stent, for 5 minutes at room temperature). After cleaning, the stents were handled with powder-free latex gloves only.

Prior to implantation, the stents were cut to the lengths specified by the experimental design. Each stent underwent visual inspection and documentation by means of macroscopic photography, capturing images at a magnification of 1.25× along the length of each device in increments of 15 mm from end to end. Thereafter, each stent was individually placed on an delivery (assembly) tube. Assembly tubes were polymeric or stainless steel hypotubing.

Surgical Methodology for Vein Grafting and Stenting

Animals were prepared according to standard procedures as necessary for femoral implantation and for aorto-coronary implantation. The lesser saphenous vein was harvested from one leg of each animal and prepared for graft construction. Briefly, after an incision over the path of the saphenous vein at the back of the calf muscle, the vein was dissected free from surrounding tissue. The vein was then ligated and cannulated proximally. After injection of blood containing heparin and papavarine, the side branches were ligated and divided. The distal end of the vein was then ligated and the vein was be tested for any leakage. In the case that the harvested length of saphenous vein was not sufficient for the construction of the aorto-coronary graft and one femoral graft, the lesser saphenous vein from the other leg of the animal was harvested in the same fashion.

Each animal underwent CABG surgery under full cardiopulmonary bypass. Briefly, the sternum of the animal was opened and cardiopulmonary bypass was established. In parallel, each vein graft was be prepared according to the type of graft called out in the experimental design. In the case of a stented graft, the saphenous vein and stent were assembled by placing the stent on an delivery (or assembly) tube, feeding the vein through the tube, and then carefully removing the tube while holding the vein and stent in place.

For grafts receiving fibrin glue, the glue was applied to the graft at this stage by spraying, while the vein was injected gently with papaverine in blood, in order to gently squeeze or press the vein against the inside of the stent. Pursuant to experimental design, all stented CABG grafts and half of the non-stented control CABG grafts received fibrin glue.

For the implantation of the vein graft, the distal anastomosis to the left anterior descending artery (LAD) was constructed first in an end-to-side fashion. After the distal anastomosis was completed, the proximal anastomosis of the vein graft to the aortic ostium was performed. For stented grafts, both anastomoses were fashioned either with, or without, incorporating the stent into the anastomosis at discretion of surgeon. For incorporation of the stent into the anastomosis, stent and vein were cut flush, and each stent loop was included in the suture stitches. For anastomosis without stent incorporation, the stent was cut 2 mm shorter than the vein, and the stent was not included in the anastomotic stitches. After reinstating physiological circulation, the sternum of the animal was closed.

After the CABG surgery was completed, the femoral grafts were implanted bilaterally. Incisions were made to open the groins, and the superficial femoral vessels were dissected between the deep femoral artery proximally, and branching sites distally. For the femoral position receiving a femoral vein graft, a 5 cm long piece of the femoral vein was harvested. For the femoral position receiving the lesser saphenous vein as a graft, excision of the femoral vein was not performed.

A 5 cm long segment of the femoral artery was excised and the proximal end-to-end anastomosis of the reversed vein was then performed. For stented grafts, the stent was placed over the vein at this stage, utilizing a delivery (assembly) tube in a similar fashion as described above for stented CABG graft preparation. After this step, the distal anastomosis was performed in an end-to-end fashion. For stented grafts, the stent was positioned such that it covered each anastomosis 1 cm proximally and 1 cm distally, and was secured in this position with two adventitial stay sutures on each anastomosis.

For replicates where the femoral grafts received fibrin glue, the glue was applied to the graft by spraying, after both anastomoses of the graft have been completed. Thereafter, the groin incisions were closed.

Implant Photography

For complete documentation, a set of photographs was taken both pre-implantation and immediately after implantation (pre-closure) for vein grafts in the femoral position and for vein grafts in the aorto-coronary position. Pre-closure, each vein graft was photographed in-situ to document the general nature of the implant and the degree of anastomotic size matching.

Termination

At the times indicated, the implanted devices were removed and evaluated. Terminations were scheduled to fall within 3 days of the assigned implant duration. Animals were prepared for femoral vein graft expalantion, and/or aorto-coronary vein graft explantation according to standard procedures.

In situ Perfusion Fixation was used prior to explantation according to procedure described in Example, 1, above, adapted as necessary for femoral vein grafts and aorto-coronary vein grafts. A complete set of histology slides was also prepared.

Graft Excision

Each femoral vein graft (stented and non-stented control) was removed in an en-bloc excision, with attached 1-3 cm native proximal and distal artery tissue according to standard procedures. For each heart with a CABG graft, the heart was excised entirely.

Angiographic Patency Assessment of CABG Grafts

Angiographic patency assessment of all explanted hearts with the aorto-coronary grafts was carried out as described below. Immediately after the explantation of the heart, the ascending aorta was clamped proximally and distally to the proximal anastomoses of the aorto-coronary graft. The proximal vascular clamp was applied just above the native coronary ostia to ensure that contrast media would not escape through the native coronary vessels or through the aortic valve. The distal clamp was applied just beneath the origin of the head and neck vessels on the aortic arch to ensure that the contrast media only flowed along the aorto-coronary graft (if the graft was patent). Thereafter, the position of the graft was marked using small liga clips on soft tissue next to the graft, serving to indicate the position of the graft at the start of the angiography before the injection of any contrast solution.

The explanted heart prepared in the described fashion with the attached aorto-coronary graft was subjected to tissue fixation in 4% formaldehyde solution for not less than 2 hours prior to the angiographic assessment.

An interventional angiography system was used for the CABG patency assessment. The explanted heart was positioned appropriately to ensure unobstructed imaging of grafts. Contrast media was injected via an aortic root cannula inserted at the time of explantation for perfusion fixation of the heart. Non-ionic Iopromide contrast medium (e.g. Ultravist® 300) diluted 50% using 0.9% NaCl solution, was used as contrast solution. Approximately 20 ml of contrast solution was used with each imaging attempt. The views facilitated were mainly a postero-anterior view as well as a right anterior oblique view. While the contrast solution was being injected, the image was captured as a dynamic clip, from which appropriate still pictures were selected at a later stage. Angiographic still images were also captured with the angiography system. After each exposure, including injection of contrast solution, the ascending aorta and graft were flushed with approximately 100 ml 0.9% NaCl solution.

On completion of the angiographic assessment, the aorto-coronary graft was again flushed with approximately 100 ml 0.9% NaCl solution.

In the case of an occluded aorto-coronary graft, it was not possible to establish flow of the contrast solution through the graft. Depending on the position of the occlusion, filling of the graft with contrast solution could sometimes be observed angiographically. The subsequent flushing procedure was adjusted as required for occluded grafts. Angiographic recordings for each heart was transferred to an electronic storage medium (e.g CD-ROM).

Faxitron Radiographic Assessment of Stented Grafts

Tissue-fixed explants of entire hearts with stented coronary vein grafts, and stented femoral vein grafts, were provided in 70% ethanol for Faxitron X-ray assessment of the stented vein grafts using a Faxitron MX-20 DC4. Hearts with non-stented coronary grafts and non-stented femoral grafts did not require Faxitron assessment. After Faxitron imaging and assessment, hearts with untouched stented coronary vein grafts, and stented femoral vein grafts, were studied for further analysis.

General Sectioning, Photography, and Labeling Information

Stented and non-stented aorto-coronary vein grafts were excised from tissue-fixed hearts, and stented and non-stented femoral vein grafts were removed in an en-bloc excision, as described above. All explanted vein grafts were dissected into various sections representing proximal anastomotic region, mid region, and distal anastomotic region of the graft. Sections included cuts perpendicular to the vein graft, generating circular sections suitable for evaluation of diameters/cross sectional areas, intimal hyperplasia, and mean medial hyperplasia. Sections included cuts parallel to the vein graft, generating strips and/or split sections. It should be noted that stent wires in the stented grafts were non-removable. For complete documentation, explant macro photographs of the sections were taken during the dissection. Photographs were captured, processed, and stored in a database.

Preparation and Labeling/Staining Histological Specimens

Resin embedding was performed only for sections of stented vein grafts. Certain sections of stented grafts with NiTi (Nitinol) wires in place were processed and embedded in resin, and sectioned to 6 to 8 µm thick sections. Slides were stained with haemotoxylon & eosin, Masson's Trichrome, Verhoefs Elastin, Azan, and Movat, as required. Wax embedding was only performed for sections of non-stented control vein grafts. The design of the stents in this study did not permit the removal of Nitinol wires from the section, such that wax embedding of the stents was not feasible. Sections embedded in wax were sectioned at 3 µm intervals.

Scanning Electron Microscopy (SEM) and Sample Preparation

After overnight fixation (2% glutaraldehyde in PBS), selected sections were dehydrated through graded ethanol, critical point dried (Balzers CPD), and gold coated (using a Polaron sputter coater). Samples were viewed on either on a JEOL microscope or a LEO microscope. Representative images were taken of the lumenal surfaces at magnifications in the range of 15 10,000× using an Orion electronic capturing system (for JEOL microscope) or LEO-32 image capturing system (for LEO microscope).

Image Analysis, Evaluation, and Scoring

A Leica DM RB microscope with an attached Leitz DC200 digital camera was used to visualize and capture macro- and histology color images of the vein grafts. Image analysis were performed using Leica's Qwin 500 software. Minimum and maximum lumenal diameters were measured on photographs of selected sections, using a commercial image analysis software (e.g., Leica Qwin).

For wax-embedded sections, images of Movat stained slides were captured at a magnification of 0.5×. For resin-embedded sections, images of haematoxylin & eosin stained slides were captured at a magnification of 0.5×. Measurements on selected cross-sectional slides were based on 5× and 10× magnification, and were performed on composite images, whereby the entire circumference of the graft was reconstructed. On average, a composite image consisted of 10-25 single frames. Measurements on anastomotic sections utilized 1.6× mag images for the analysis of Pannus/AIH. Measurements were made on a grid of 1 mm increments, starting from the anastomosis. All measurements were undertaken by interactive highlighting of the area of interest and detection-filtering of the color images (achieved by 'thresholding'). All data was recorded in a database.

The following parameters were measured:

From macroscopic images, lumenal parameters including (a) cross sectional area, (b) mean diameter calculated from internal circumference, and (c) minimum and maximum diameters measured through center of gravity of the patent lumen.

From histological sections, (1) lumenal parameters (measured from 0.5× magnification images), including (a) cross sectional area, (b) mean diameter calculated from internal circumference, and (c) minimum and maximum diameters measured through center of gravity; and (2) intimal hyperplasia (measured from 10× magnification composites), including (a) cross sectional area, and (b) thickness (maximum, minimum, and mean); and (3) media (measured from 10× magnification composites), including (a) cross sectional area, (b) thickness (maximum, minimum, and mean), and (c) differential percentage of smooth muscle cells.

From histological sections, (1) anastomotic intimal hyperplasia/pannus (measured from 1.6× magnification images), including (a) cross sectional area, and (b) thickness (mean); and (2) media (measured from 10× magnification composites), including (a) cross sectional area, (b) thickness (maximum, minimum, and mean), and (c) differential percentage of smooth muscle cells.

Statistical Analysis

Individual data figures represented a mean as determined using computer planimetry. One-way analysis of variance (ANOVA) was performed on the numerical data using commercial software to be specified at the time. Because of the potential for unique variability in response between individual animals, and the restriction of performing the surgical implants in groups of four animals, blocking was used in the analysis on these factors. The analysis compared and contrasted the various measurements relative to the vein graft type and position along the stent. Significance levels of 0.05 or less were accepted as being statistically significant.

Graft Patency

Explant patency for a total of 16 baboons with stented grafts and 13 baboons with non-stented grafts is summarized in Table VIII below Patency was established by a combination of methods including palpation assessment through the skin before incision (femoral grafts only), perfusion during in-situ perfusion fixation, angiographic assessment on explanted hearts (CABG grafts only), and patency assessment during graft dissection for histological analysis after explanation.

TABLE

Effect of Graft Position, Vein Source, Stenting, and Glue on Graft Patency

| Graft Position | Vein Source | Stenting | Gluing | Total No. Grafts | No. Grafts Patent | Patency Rate (%) |
|---|---|---|---|---|---|---|
| CABG-LAD | Saph | Non-stented | No glue | 5 | 4 | 80 |
| Femoral | Saph | Non-stented | No glue | 5 | 4 | 80 |
| Femoral | Femoral | Non-stented | No glue | 5 | 4 | 80 |
| CABG-LAD | Saph | Non-stented | Glue | 8 | 7 | 88 |
| Femoral | Saph | Non-stented | Glue | 8 | 6 | 75 |
| Femoral | Femoral | Non-stented | Glue | 8 | 4 | 50 |
| CABG-LAD | Saph | Stented | Glue | 16 | 14 | 88 |
| Femoral | Saph | Stented | No glue | 8 | 3 | 38 |
| Femoral | Femoral | Stented | No glue | 8 | 3 | 38 |
| Femoral | Saph | Stented | Glue | 8 | 6 | 75 |
| Femoral | Femoral | Stented | Glue | 8 | 7 | 88 |

Histology and Image Analysis to Determine Effects on Vein Structure

Macrophotography images of dissected explants showed that non-stented CABG (e.g., saphenous vein without a stent) had a small lumen. In contrast, stented CABG showed larger lumens and thin walls.

Cross-sectional images of non-stented CABG showed some remnant vessels passing through fibrotic tissues in the vein walls. Cross-sectional images of stented CABG showed large lumens with little wall thickening. Holes caused by removal of stent wires prior to section preparation were also visible.

When various parameters were measured in explanted CABG containing saphenous vein, it was found that the non-stented CABG with saphenous vein and without glue (fibrin) had the greatest intimal hyperplasia (IH) thickness, the CABG with saphenous vein and with glue had the next largest IH thickness, and the stented CABG with saphenous vein and glue had the smallest IH thickness, i.e., the least wall thickening. In explanted CABG, media thickness and adventitia thickness showed the same pattern. Mean lumenal area and lumenal diameter showed a pattern similar to that expected from inspection of the cross-sectional images, i.e., non-stented CABG with saphenous vein and no glue had the smallest lumen, while the stented CABG with glue had a larger lumen. All CABG had levels of endothelial cell coverage between 80 to 100%.

In explanted femoral grafts, non-stented femoral and saphenous veins had the highest mean IH thickness and mean media thickness, while stented femoral grafts had thinner IH and media (lower thickness). Mean adventitia thickness did not vary as much among femoral grafts that were stented or non-stented, or containing femoral or saphenous veins. Patterns of mean lumenal area and lumenal diameter were difficult to interpret.

While the embodiments of the invention described herein are presently preferred, various modifications and improvements can be made without departing from the spirit and scope of the invention. The scope of the invention is indicated by the appended claims, and all changes that fall within the meaning and range of equivalents are intended to be embraced therein.

What is claimed is:

1. A method for selecting a tubular support for placement at an ablumenal surface of a vessel of a vessel graft apparatus, said method comprising:
    measuring a maximum outer diameter and a minimum outer diameter of the vessel;
    providing a set of a plurality of substantially tubular supports, each of said supports of the set having a distinct size; and
    selecting one of said plurality of said supports in the set, wherein the selected support has a size that is appropriate to diametrically downsize the vessel when the support is mounted at the ablumenal surface.

2. A method as in claim 1 wherein the selected support has a size that is appropriate to diametrically downsize the vessel by between 1-40%.

3. A method as in claim 1 wherein the selected support has an inner diameter that is smaller than the minimum outer diameter of the vessel.

* * * * *